(12) United States Patent
Hall et al.

(10) Patent No.: US 11,926,833 B2
(45) Date of Patent: Mar. 12, 2024

(54) COMPOSITIONS AND METHODS FOR ENHANCING BIOMASS PRODUCTIVITY IN PLANTS

(71) Applicant: Living Carbon PBC, Hayward, CA (US)

(72) Inventors: Madeline Hall, Hayward, CA (US); Li-Wei Chiu, Hayward, CA (US); Rebecca Dewhirst, Hayward, CA (US); Jacob Hoyle, Hayward, CA (US); Patrick Mellor, Hayward, CA (US); Karli Rasmussen, Hayward, CA (US); Yumin Tao, Hayward, CA (US)

(73) Assignee: LIVING CARBON PBC, Haywood, CA (US)

( * ) Notice: Subject to any disclaimer, the term of this patent is extended or adjusted under 35 U.S.C. 154(b) by 0 days.

(21) Appl. No.: 18/153,863

(22) Filed: Jan. 12, 2023

(65) Prior Publication Data

US 2023/0235336 A1    Jul. 27, 2023

Related U.S. Application Data

(60) Provisional application No. 63/302,895, filed on Jan. 25, 2022.

(51) Int. Cl.
  *C12N 15/52* (2006.01)
  *C12N 15/113* (2010.01)
(52) U.S. Cl.
  CPC ............ *C12N 15/52* (2013.01); *C12N 15/113* (2013.01); *C12N 2310/11* (2013.01)
(58) Field of Classification Search
  CPC .................................................... C12N 15/52
  USPC ......................................................... 800/286
  See application file for complete search history.

(56) References Cited

U.S. PATENT DOCUMENTS

| | | | |
|---|---|---|---|
| 7,208,318 B2 | 4/2007 | Hain et al. | |
| 7,396,979 B2 | 7/2008 | Alexandrov et al. | |
| 7,663,027 B2 | 2/2010 | Feldmann et al. | |
| 7,803,983 B2 | 9/2010 | Alexandrov et al. | |
| 7,884,261 B2 | 2/2011 | Alexandrov et al. | |
| 8,022,273 B2 | 9/2011 | Christensen et al. | |
| 8,937,215 B2 | 1/2015 | Ayal et al. | |
| 9,371,538 B2 | 6/2016 | Kreuzaler et al. | |
| 9,388,423 B2 | 7/2016 | Hatzfeld et al. | |
| 10,106,826 B2 | 10/2018 | Yuan et al. | |
| 10,233,460 B2 | 3/2019 | Zhou et al. | |
| 10,273,496 B2 | 4/2019 | Peterhaensel et al. | |
| 10,337,022 B2 | 7/2019 | Roberts et al. | |
| 10,450,580 B2 | 10/2019 | Ambavaram et al. | |
| 10,519,206 B2 | 12/2019 | Noelke et al. | |
| 2004/0019927 A1 | 1/2004 | Sherman et al. | |
| 2006/0236427 A1 | 10/2006 | Chiang et al. | |
| 2007/0169219 A1 | 7/2007 | Nadzan et al. | |
| 2011/0023181 A1 | 1/2011 | Maurino et al. | |
| 2011/0268865 A1 | 11/2011 | Kebeish et al. | |
| 2012/0297505 A1 | 11/2012 | Wu et al. | |
| 2013/0007916 A1 | 1/2013 | Spalding | |
| 2013/0019346 A1 | 1/2013 | Hatzfeld | |
| 2013/0019347 A1 | 1/2013 | Sanz Molinero | |
| 2013/0031670 A1 | 1/2013 | Vandenabeele | |
| 2013/0125262 A1 | 5/2013 | Russinova et al. | |
| 2015/0118385 A1 | 4/2015 | Kebeish et al. | |
| 2015/0267218 A1 | 9/2015 | Dangoor et al. | |
| 2016/0138038 A1 | 5/2016 | Sederoff et al. | |
| 2018/0079789 A1 | 3/2018 | Wu et al. | |
| 2018/0105830 A1 | 4/2018 | Dangoor et al. | |
| 2018/0223295 A1 | 8/2018 | Harling et al. | |
| 2018/0258440 A1* | 9/2018 | Ort | C12N 15/8262 |
| 2018/0291352 A1 | 10/2018 | Malik et al. | |
| 2019/0376077 A1 | 12/2019 | Peterhaensel et al. | |
| 2020/0048651 A1 | 2/2020 | Ambavaram et al. | |
| 2020/0208125 A1 | 7/2020 | Negi et al. | |

FOREIGN PATENT DOCUMENTS

| | | |
|---|---|---|
| CN | 110184293 A | 8/2019 |
| CN | 110564760 A | 12/2019 |
| CN | 110628810 A | 12/2019 |
| KR | 101509032 B1 | 4/2015 |
| WO | 2016164810 | 10/2016 |

OTHER PUBLICATIONS

Thomas et al. The Plant Journal 25(4):417-425 (Year: 2001).*
South et al., "Synthetic Glycolate Metabolism Pathways Stimulate Crop Growth and Productivity in the Field," Science 363, No. 6422: eaat9077 (2019).
Maier et al., "Transgenic Introduction of a Glycolate Oxidative Cycle into A. Thaliana Chloroplasts Leads to Growth Improvement," Front. Plant Sci., 3:38 (2012).
Pick et al., "PLGG1, a Plastidic Glycolate Glycerate Transporter, is Required for Photorespiration and Defines a Unique Class of Metabolite Transporters," Proc. Natl. Acad. Sci. 110:3185-3190 (2013).
Kebeish et al., "Chloroplastic Photorespiratory Bypass Increases Photosynthesis and Biomass Production in Arabidopsis Thaliana," Nat. Biotech. 25:593-599 (2007).

(Continued)

*Primary Examiner* — Li Zheng
(74) *Attorney, Agent, or Firm* — Troutman Pepper Hamilton Sanders LLP (Rochester)

(57) ABSTRACT

The present disclosure relates to a transgenic plant cell comprising polynucleotide sequences encoding glycolate dehydrogenase, malate synthase, and an inhibitory polynucleotide targeting an endogenous glycolate transporter Plgg1, wherein expression of endogenous glycolate transporter Plgg1 in the transgenic plant cell is about 20% to 80% of expression of endogenous glycolate transporter Plgg1 in a plant cell that is not transformed with an inhibitory polynucleotide targeting an endogenous glycolate transporter Plgg1. Also disclosed are transgenic plants, transgenic plant cultures, and methods for increasing photosynthesis efficiency in plants. The disclosed methods enhance biomass productivity and reduce the negative impact of photorespiration and introduction of transgenic constructs on plant growth.

26 Claims, 17 Drawing Sheets

Specification includes a Sequence Listing.

(56) References Cited

OTHER PUBLICATIONS

Shim et al., "Loss of Function of rice Plastidic Glycolate/Glycerate Translocator 1 Impairs Photorespiration and Plant Growth," Frontiers in Plant Science 10: 1726 (2020).
Non-Final Office Action for U.S. Appl. No. 15/913,395 dated Jun. 12, 2020.
Response to Jun. 12, 2020 Non-Final Office action for U.S. Appl. No. 15/913,395, dated Sep. 11, 2020.
Final Office Action for U.S. Appl. No. 15/913,395, dated Dec. 23, 2020.
Response to Dec. 23, 2020 Final Office action for U.S. Appl. No. 15/913,395, dated May 20, 2021.
Non-Final Office Action for U.S. Appl. No. 15/913,395 dated Jun. 24, 2021.
Response to Jun. 24, 2021 Non-Final Office action for U.S. Appl. No. 15/913,395, dated Nov. 24, 2021.
Final Office Action for U.S. Appl. No. 15/913,395 dated Mar. 16, 2022.
Response to Mar. 16, 2022 Final Office action for U.S. Appl. No. 15/913,395, dated Jun. 16, 2022.
Non-Final Office Action for U.S. Appl. No. 15/913,395, dated Aug. 16, 2022.
Examiner Interview Summary for U.S. Appl. No. 15/913,395, dated Dec. 22, 2022.
Response to Aug. 16, 2022 Non-Final Office action for U.S. Appl. No. 15/913,395, dated Feb. 1, 2023.
Hart et al., "Gene Expression—Phenotype Relationships in a Field Study of Photorespiration-Suppressed Transgenic Poplars," Abstract from Plant and Animal Genome Conference 30 (Available online mid-Dec. 2022).
Written Opinion and International Search Report for WO2023147222, dated Jun. 22, 2023.

\* cited by examiner

```
                        1                                                    50
SEQ_ID_NO_38_Palba      ATGGCTACTC CTTTAGTCGC TCTTTCCGTT CAACTCTGTC ATCACCACTC
SEQ_ID_NO_39_Ptrem      ATGGCTACTC CTTTAGTCGC TCTTTCCGTT CAACTCTGTC ATCACCACTC
SEQ_ID_NO_06_Ptric      ATGGCTACTC CTTTAGTCGC TCATTCCGTT CAGCTCTGTC ATCACCACTC
SEQ_ID_NO_08_RNAI       .......... .......... .......... .......... ..........

51                                                   100
SEQ_ID_NO_38_Palba      AAAACAATAT TCTTTCAAAT CACAATCACA ATCACGTGTC AATAGGGATT
SEQ_ID_NO_39_Ptrem      AAAACAATAT TCTTTCAAAT CACAATCAC. .....GTGTC AATAGGGATT
SEQ_ID_NO_06_Ptric      AAAACAATAT TCTTTCAAAT CACAATCAC. .....GTGTC AATAGGGATA
SEQ_ID_NO_08_RNAI       .......... .......... .......... .......... ..........

101                                                  150
SEQ_ID_NO_38_Palba      TCCGTACAAA AACACTACTT GGTGTTTACA ATGGATTCCA AAATGTATAT
SEQ_ID_NO_39_Ptrem      TCCGTACGAA AACACTACTT GGTGTTTACA ATGGATTCCA AAATGTATAT
SEQ_ID_NO_06_Ptric      TCGGTACAAA AACACTACTT GGTGTTTACA ATGGATTCCA CAATGTATAT
SEQ_ID_NO_08_RNAI       .......... .......... .......... .......... ..........

151                                                  200
SEQ_ID_NO_38_Palba      AACCAATCTT ATTTTCATAA GCCTTGGGCA CCCATTAGAG TTCTTGAGCC
SEQ_ID_NO_39_Ptrem      AACCAATCTT ATTTTCATAA GCCTTGGGCA CCCATTAGAG TTCTTGAGCC
SEQ_ID_NO_06_Ptric      AACCAATCTT ATTTTCATAA GCCTTGGGCA CCCATTAGAG TTCTTGAGCC
SEQ_ID_NO_08_RNAI       .......... .......... .......... .......... ..........

201                                                  250
SEQ_ID_NO_38_Palba      TAATTCAAGG TTCTTGCAAA TGGGTCCTCA AGAAACCTGC TCTAGTCGAG
SEQ_ID_NO_39_Ptrem      TAATTCAAGG TTCTTGCAAA TGGGTCCTCA AGAAACCTGC TCTAGTCGAG
SEQ_ID_NO_06_Ptric      TAATTCAAGG TTCTTGCAAA TGGGTCCTCA AGAAACCTGC TCTAGTCGAG
SEQ_ID_NO_08_RNAI       .......... .......... .......... .......... ..........

251                                                  300
SEQ_ID_NO_38_Palba      GAATTTCCAA GAAATCTATG AGCTCAGAAG GCAGTACCAG TACTAGCTCT
SEQ_ID_NO_39_Ptrem      GAATTTCCAA GAAATCTATG AGCTCAGAAG GCAGTACCAG TACTAGCTCT
SEQ_ID_NO_06_Ptric      GAATTTCCAA GAAATCTATG AGCTCAGAAG GCAGTACCAG TACTAGCTCT
SEQ_ID_NO_08_RNAI       .......... .......... .......... .......... ..........

301                                                  350
SEQ_ID_NO_38_Palba      TCATCTATTT CTCAACAGGT GATTGGGATC TTGCATTTGC TTGTTTCACT
SEQ_ID_NO_39_Ptrem      TCATCTATTT CTCAACAGGT GATTGGGATC TTGCATTTGC TTGTTTCACT
SEQ_ID_NO_06_Ptric      TCATCTATTT CTCAACAGGT GATTGGGATC TTGCATTTGC TTGTTTCACT
SEQ_ID_NO_08_RNAI       .......... .......... .......... .......... ..........

351                                                  400
SEQ_ID_NO_38_Palba      TGGGATTATC CTTGCAATGG ATAAGTTGTT GAAAAAGGCA TTTGTGGCTG
SEQ_ID_NO_39_Ptrem      TGGGATTATC CTTGCAATGG ATAAGTTGTT GAAAAAGGCA TTTGTGGCTG
SEQ_ID_NO_06_Ptric      TGGGATTATC CTTGCAATGG ATAAGTTGTT GAAAAAGGCA TTTGTGGCTG
SEQ_ID_NO_08_RNAI       .......... .......... .......... .......... ..........

401                                                  450
SEQ_ID_NO_38_Palba      CTGCTATCAA GTTCCAAGT GCTCTGTTTG GCATGTTCTG CATATTCTCA
SEQ_ID_NO_39_Ptrem      CTGCTATCAA GTTCCAAGT GCTCTGTTTG GCATGTTCTG CATATTCTCG
SEQ_ID_NO_06_Ptric      CTGCTATCAA GTTCCAAGT GCTCTGTTTG GCATGTTCTG CATATTCTCA
SEQ_ID_NO_08_RNAI       .......... .......... .......... .......... ..........

451                                                  500
SEQ_ID_NO_38_Palba      GTTTTAGTGA TTCTTGATAT AACTATTCCG GCTGCTGCAA CAAGCTTAAT
SEQ_ID_NO_39_Ptrem      GTTTTAGTGA TTCTTGATAT AACTATTCCG GCTGCTGCAA CAAGCTTAAT
SEQ_ID_NO_06_Ptric      GTTTTAGTCA TTCTTGATAT AACTATTCCG GCTGCTGCAA CAAGCTTAAT
SEQ_ID_NO_08_RNAI       .......... .......... .......... .......... ..........
```

FIG. 4

```
                       501                                                        550
SEQ_ID_NO_38_Palba     GAACTTCTTT GAGCCAGCAC TGTTATTCAT TCAGAGATGG CTTCCGTTGT
SEQ_ID_NO_39_Ptrem     GAACTTCTTT GAGCCAGCAC TGTTATTCAT TCAGAGATGG CTTCCGTTGT
SEQ_ID_NO_06_Ptric     GAACTTCTTT CAGCCAGCAC TGTTATTCAT TCAGAGATGG CTTCCGTTGT
SEQ_ID_NO_08_RNAI      .......... .......... .......... .......... ..........

551                                                        600
SEQ_ID_NO_38_Palba     TCTACGTTCC ATCATTGGTT GTTTTGCCTC TCTCTGTTAA AGATATCCCT
SEQ_ID_NO_39_Ptrem     TCTACGTTCC ATCATTGGTT GTTTTGCCTC TCTCTGTTAA AGATATCCCT
SEQ_ID_NO_06_Ptric     TCTACGTTCC ATCATTGGTT GTTTTGCCTC TCTCTGTTAA AGATATCCCT
SEQ_ID_NO_08_RNAI      .......... .......... .......... .......... ..........

601                                                        650
SEQ_ID_NO_38_Palba     GCTGCATCAG GTGTCAAGAT TTGCTTCATC ACAGCTGGAG GGTGGCTGGC
SEQ_ID_NO_39_Ptrem     GCTGCATCAG GTGTCAAGAT CTGCTTCATC ACAGCTGGAG GGTGGCTGGC
SEQ_ID_NO_06_Ptric     GCTGCATCAG GTGTCAAGAT TTGCTTCATC ACAGCTGGAG GGTGGTTGGC
SEQ_ID_NO_08_RNAI      .......... .......... .......... .......... ..........

651                                                        700
SEQ_ID_NO_38_Palba     GTCACTTTGT GTGGCGGGTT TCACAGCTAT TGCTGTGAGA AAAATGGTGA
SEQ_ID_NO_39_Ptrem     GTCACTTTGC GTGGCGGGTT TCACAGCTAT TGCTGTGAGA AAATTGGTGA
SEQ_ID_NO_06_Ptric     GTCACTTTGT GTGGCGGGTT TTACAGCTAT TGCTGTGAGA AAAATGGTGA
SEQ_ID_NO_08_RNAI      .......... .......... .......... .......... ..........

701                                                        750
SEQ_ID_NO_38_Palba     AGACAGAAAT GACTGACGCT GAGCCTATGG CGAAACCCTC TCCTTTTTCT
SEQ_ID_NO_39_Ptrem     AGACAGAAAT GACTGACGCT GAGCCTATGG CGAAACCCTC TCCTTTTTCT
SEQ_ID_NO_06_Ptric     AGACAGAAAT GACTGATGCT GAGCCTATGG CGAAACCCTC TCCTTTTTCT
SEQ_ID_NO_08_RNAI      .......... .......... .......... .......... ..........

751                                                        800
SEQ_ID_NO_38_Palba     CCATTGGAAA TGTGGGCTTG GAGTGGGGTC TTCCTTGTAT CATTTGTTGT
SEQ_ID_NO_39_Ptrem     CCATTGGAAA TGTGGGCTTG GAGTGGGGTC TTCCTTGTAT CATTTGTTGT
SEQ_ID_NO_06_Ptric     CCATTGGAAA TATGGGCTTG GAGTGGGGTC TTCCTTGTAT CATTTGTTGT
SEQ_ID_NO_08_RNAI      .....GGAAA TATGGGCTTG GAGTGGGGTC TTCCTTGTAT CATTTGTTGT 801                                                        850
SEQ_ID_NO_38_Palba     CGCATTATTA TATAGAACGG CATTGGGGAC TGCAGCCAGA ACATGCCTTC
SEQ_ID_NO_39_Ptrem     CGCATTATTA TATAGAACGG CATTGGGGAC TGCAGCCAGA ACATGCCTTC
SEQ_ID_NO_06_Ptric     CGCATTATTA TATAGAACGG CATTAGGGAC TGCAGCCAGA ACATGCCTTC
SEQ_ID_NO_08_RNAI      CGCATTATTA TATAGAACGG CATTAGGGAC TGCAGCCAGA ACATGCCTTC 851                                                        900
SEQ_ID_NO_38_Palba     CTTTCCTACT AGCGTCCACC GTGCTAGGCT ATATGGTTGG TTCTGGGTTA
SEQ_ID_NO_39_Ptrem     CTTTCCTACT AGCGTCCACC GTGCTAGGCT ATATGGTTGG TTCTGGGTTA
SEQ_ID_NO_06_Ptric     CTTTCCTACT AGCGTCCACC GTGCTAGGCT ATATGGTTGG TTCTGGGTTA
SEQ_ID_NO_08_RNAI      CTTTCCTACT AGCGTCCACC GTGCTAGGCT ATATGGTTGG TTCTGGGTTA 901                                                        950
SEQ_ID_NO_38_Palba     CCATCTGGTG TTAAGAAGGT TTTCCATCCC ATTATTTGTT GTGCACTATC
SEQ_ID_NO_39_Ptrem     CCATCTGGTG TTAAGAAGGT TTTCCATCCC ATTATTTGCT GTGCACTATC
SEQ_ID_NO_06_Ptric     CCATCTGGTG TTAAGAAGGT TTTCCATCCC ATTATTTGTT GTGCACTATC
SEQ_ID_NO_08_RNAI      CCATCTGGTG TTAAGAAGGT TTTCCATCCC ATTATTTGTT GTGCACTATC 951                                                       1000
SEQ_ID_NO_38_Palba     TGCAGATTTG GCAGCGTTGG CCTTTGGGTA CCTTTCCCAA TCTGGACTTG
SEQ_ID_NO_39_Ptrem     TGCAGATTTG GCAGCGTTGG CCTTTGGGTA CCTTTCCCAA TCTGGACTTG
SEQ_ID_NO_06_Ptric     TGCAGATTTG GCAGCGTTGG CCTTTGGGTT CCTTTCCCAA TCTGGACTCG
SEQ_ID_NO_08_RNAI      TGCAGATTTG GCAGCGTTGG CCTTTGGGTT CCTTTCCCAA TCTGGACTCG
```

FIG. 4 (continued)

```
                             1001                                                1050
SEQ_ID_NO_38_Palba   ATCCCGTTCT AGGATATTAC CTTACAAAAG TTTCATCTAA TCCTGGAGCT
SEQ_ID_NO_39_Ptrem   ATCCCGTTCT AGGATATTAC CTTACAAAAG TTTCATCTAA TCCTGGAGCT
SEQ_ID_NO_06_Ptric   ATCCCGTTCT AGGATATTAC CTTACAAAAG TTTCATCTAA TCCTGGAGCT
SEQ_ID_NO_08_RNAI    ATCCCGTTCT AG........ .......... .......... ..........

1051                                                1100
SEQ_ID_NO_38_Palba   GGTGATGTGT TAATGGGATT CTTGGGACCT GTCATTCTTT CTTTTGCCTT
SEQ_ID_NO_39_Ptrem   GGTGATGTGT TAATGGGATT CTTGGGACCT GTCATTCTTT CTTTTGCCTT
SEQ_ID_NO_06_Ptric   GGTGATGTGT TAATGGGATT CTTGGGACCT GTCATTCTTT CTTTTGCCTT
SEQ_ID_NO_08_RNAI    .......... .......... .......... .......... ..........

1101                                                1150
SEQ_ID_NO_38_Palba   CTCAATGTTC AAGCAGCGAA AGCTTGTTAA GAGACATGCA GCTGAGATTT
SEQ_ID_NO_39_Ptrem   CTCAATGTTC AAGCAGCGAA AGCTTGTTAA GAGACATGCA GCTGAGATTT
SEQ_ID_NO_06_Ptric   CTCAATGTTC AAGCAGCGAA AGCTTGTTAA GAGACATGCA GCTGAGATTT
SEQ_ID_NO_08_RNAI    .......... .......... .......... .......... ..........

1151                                                1200
SEQ_ID_NO_38_Palba   TCACGTCGGT CATTGTTTCA ACACTATTTT CATTGTATTC AACGGCTCTC
SEQ_ID_NO_39_Ptrem   TCACGTCGGT CATTGTTTCA ACACTATTTT CATTGTATTC AACGGCTCTC
SEQ_ID_NO_06_Ptric   TCACGTCCGT CATTGTTGCA ACACTATTTT CATTGTATTC AACGGCTCTC
SEQ_ID_NO_08_RNAI    .......... .......... .......... .......... ..........

1201                                                1250
SEQ_ID_NO_38_Palba   GTGGGACGTC TAGTTGGGTT AGAACCAACG TTGACTGTAT CCATTATTCC
SEQ_ID_NO_39_Ptrem   GTGGGACGTC TAGTTGGGTT AGAACCAACG TTGACTGTAT CCATTATTCC
SEQ_ID_NO_06_Ptric   GTGGGACGTC TAGTTGGGTT AGAACCAACG TTGACTGTAT CCATTATTCC
SEQ_ID_NO_08_RNAI    .......... .......... .......... .......... ..........

1251                                                1300
SEQ_ID_NO_38_Palba   CAGATGTATA ACCGTGGCAT TAGCCCTCAG CATTGTGTCA TTCTTTGAAG
SEQ_ID_NO_39_Ptrem   CAGATGTATA ACCGTGGCAT TAGCCCTCAG CATTGTGTCA TTCTTTGAAG
SEQ_ID_NO_06_Ptric   CAGATGTATA ACCGTGGCAT TAGCCCTCAG CATTGTGTCA TTCTTTGAAG
SEQ_ID_NO_08_RNAI    .......... .......... .......... .......... ..........

1301                                                1350
SEQ_ID_NO_38_Palba   GTGCCAATTC ATCTCTCACA GCTGCTGTAG TTGTTGTAAC TGGTCTCATT
SEQ_ID_NO_39_Ptrem   GTGCCAATTC ATCTCTCACA GCTGCTGTAG TTGTTGTAAC TGGTCTCATT
SEQ_ID_NO_06_Ptric   GTGCCAATTC ATCTCTCACA GCTGCTGTAG TTGTTGTAAC TGGTCTCATT
SEQ_ID_NO_08_RNAI    .......... .......... .......... .......... ..........

1351                                                1400
SEQ_ID_NO_38_Palba   GGAGCAAATT TTGTACAAGC AGTGCTTGAT AAATTAAGTT TTCGTGATCC
SEQ_ID_NO_39_Ptrem   GGAGCAAATT TTGTACAAGC AGTGCTCGAT AAATTAAATT TTCGTGATCC
SEQ_ID_NO_06_Ptric   GGAGCAAATT TTGTACAAGC AGTGCTCGAT AAATTAAATT TTCGTGATCC
SEQ_ID_NO_08_RNAI    .......... .......... .......... .......... ..........

1401                                                1450
SEQ_ID_NO_38_Palba   CATTGCTCGA GGAATAGCTA CTGCTTCCAG TGCTCATGGA CTGGGAACTG
SEQ_ID_NO_39_Ptrem   CATTGCTCGA GGAATAGCAA CTGCTTCCAG TGCTCATGGA CTGGGAACTG
SEQ_ID_NO_06_Ptric   CATTGCTCGA GGAATAGCAA CTGCTTCCAG TGCTCATGGA CTGGGAACTG
SEQ_ID_NO_08_RNAI    .......... .......... .......... .......... ..........

1451                                                1500
SEQ_ID_NO_38_Palba   CAGCATTGTC AGCCAAGGAA CCTGAGGCAC TTCCATTTTG TGCCATTGCT
SEQ_ID_NO_39_Ptrem   CAGCATTGTC AGCCAAGGAA CCTGAGGCAC TTCCATTTTG TGCCATTGCT
SEQ_ID_NO_06_Ptric   CAGCATTGTC AGCCAAGGAA CCTGAGGCAC TTCCATTTTG TGCCATTGCT
SEQ_ID_NO_08_RNAI    .......... .......... .......... .......... ..........
```

FIG. 4 (continued)

```
                    1501                                                     1550
SEQ_ID_NO_38_Palba  TATGCTCTCA CTGGTATATT TGGTTCATTG TTTTGTTCAG TTCCTGCAGT
SEQ_ID_NO_39_Ptrem  TATGCTCTCA CTGGTATATT TGGTTCATTG TTTTGTTCAG TTCCTGCAGT
SEQ_ID_NO_06_Ptric  TATGCTCTCA CTGGTATATT TGGTTCATTG TTTTGTTCAG TTCCTGCAGT
  SEQ_ID_NO_08_RNAI ..........  ..........  ..........  ..........  ..........

1551                      1581
SEQ_ID_NO_38_Palba  TAGGCAAAGC TTACTTGCAA TAATTGGCTG A
SEQ_ID_NO_39_Ptrem  TAGGCAAAGC TTACTTGCAA TAATTGGCTG A
SEQ_ID_NO_06_Ptric  TAGGCAAAGC TTACTTGCAA TAATTGGCTG A
  SEQ_ID_NO_08_RNAI ..........  ..........  .......... .
```

FIG. 4 (continued)

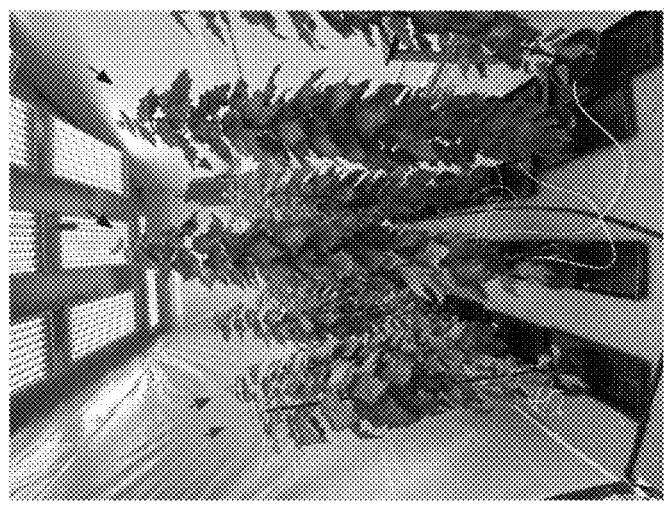
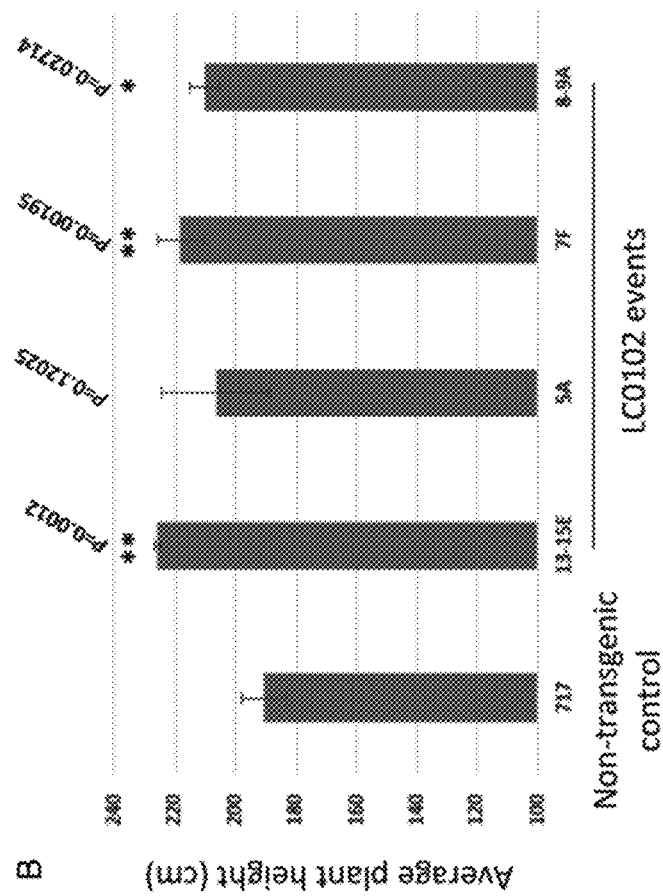
FIGs. 13A-B

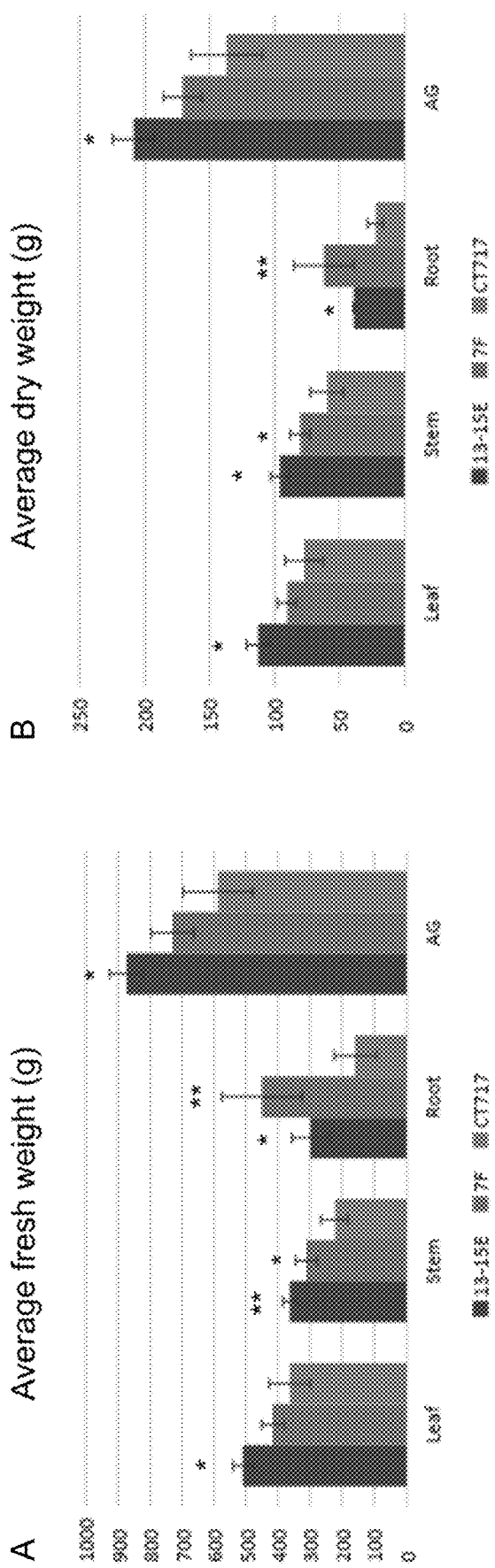
FIGs. 14A-B

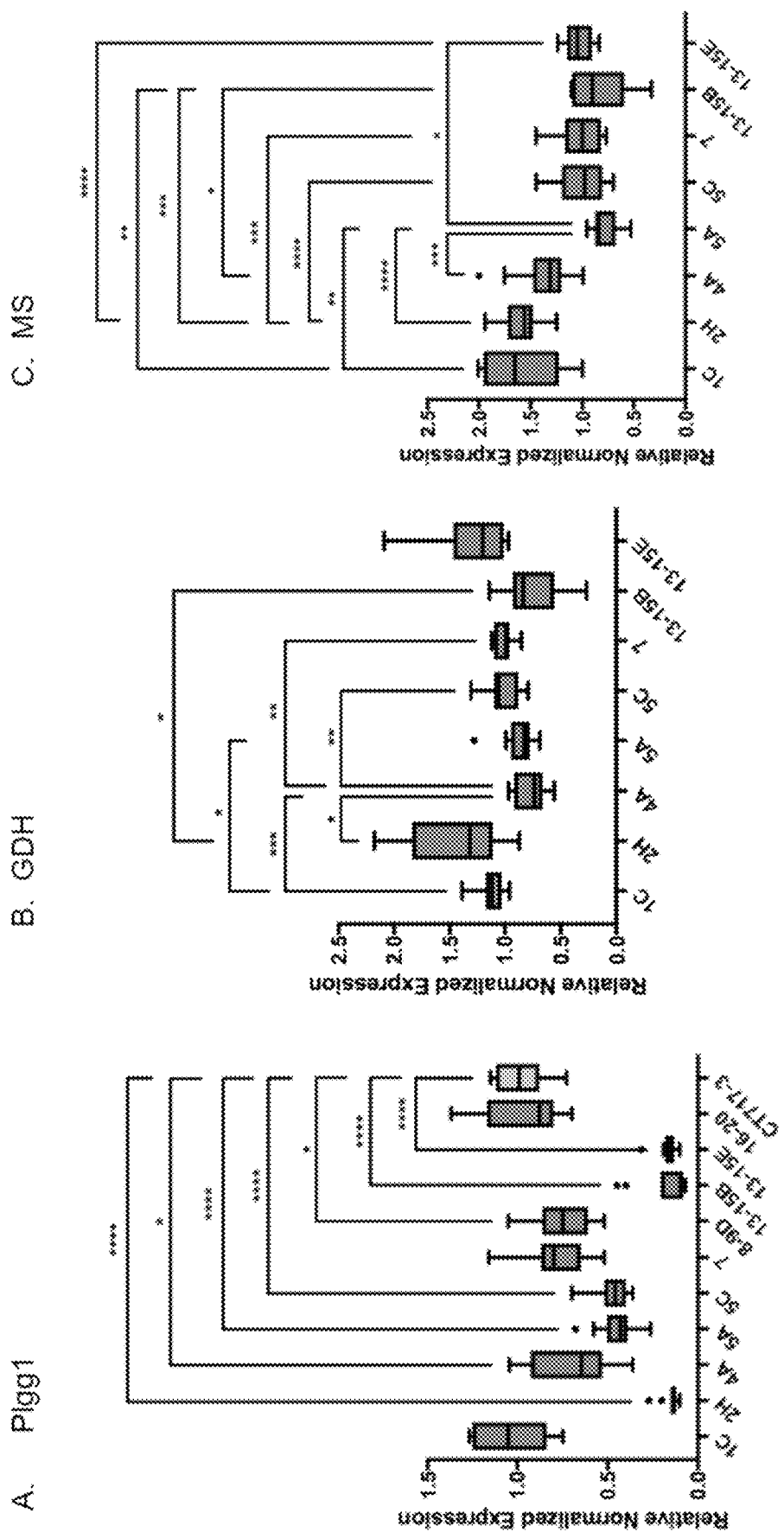
FIGs. 18A-C

COMPOSITIONS AND METHODS FOR ENHANCING BIOMASS PRODUCTIVITY IN PLANTS

This application claims the priority benefit of U.S. Provisional Patent Application Ser. No. 63/302,895, filed Jan. 25, 2022, which is hereby incorporated by reference in its entirety.

FIELD

The present disclosure relates to compositions and methods for enhancing biomass productivity and decreasing the negative impact of photorespiration in plants.

SEQUENCE LISTING

The Sequence Listing is being submitted electronically in XML format and is hereby incorporated by reference in its entirety. Said XML copy, created on Jan. 12, 2023, is named 257948000133.xml and is 100 KB in Size.

BACKGROUND

Over the last century, the burning of fossil fuels such as coal and oil has increased the concentration of carbon dioxide in the atmosphere, with consequent global warming and shift in climate patterns.

Reforestation is, in theory, a low-cost and effective method to decrease carbon dioxide concentration in the atmosphere. However, reforestation is limited by the increase in global food demand, which elevates the need for cropland, and also by political considerations. Carbon drawdown and wood production in forest trees both depend on growth rate. Genetic transformations are able to increase the durability of wood, but they could also possibly reduce growth rate. Pressure treatment solutions used for wood are expensive, toxic, and greatly increase the weight of treated wood without improving its structural properties. There is therefore a need to stimulate growth rate of forest trees.

Fertilizers and pesticides are routinely applied to plants to stimulate growth rate. However, attempts to increase photosynthetic carbon capture in plants have not proven successful in field trials.

Photorespiration is the process by which the enzyme ribulose-1,5-bisphosphate carboxylase/oxygenase ("RuBisCO") in C3 plants uses oxygen to oxygenate ribulose bisphosphate ("RuBP"), rather than fixing carbon dioxide to produce 3-phosphoglycerate and 2-phosphoglycolate, and release oxygen. This process requires energy in the form of ATP and reducing NADPH molecules and, as a consequence, it greatly reduces photosynthesis efficiency. Photorespiration produces glycolate and releases carbon dioxide and ammonia into the atmosphere. Glycolate must be metabolized at high-energy cost to prevent ammonia from accumulating in the leaves. Because of its high-energy cost, the photorespiration process significantly reduces biomass productivity and increases the release of carbon dioxide into the atmosphere. $CO_2$ emission into the atmosphere contributes to the "greenhouse effect" that has steadily increased in recent years, with consequent warming of the planet. There is a need to increase photosynthetic efficiency and biomass productivity in plants, and especially in trees.

The present disclosure is directed to overcoming these and other deficiencies in the art.

SUMMARY

One aspect of the present disclosure relates to a transgenic plant cell comprising a first promoter operably linked to a polynucleotide sequence encoding a glycolate dehydrogenase, a second promoter operably linked to a polynucleotide sequence encoding a malate synthase, and an inhibitory polynucleotide targeting an endogenous glycolate transporter Plgg1, where expression of the endogenous glycolate transporter Plgg1 in the transgenic plant cell is about 20% to 80% of expression of endogenous glycolate transporter Plgg1 in a plant cell that is not transformed with an inhibitory polynucleotide targeting an endogenous glycolate transporter Plgg1.

Another aspect of the present disclosure relates to a transgenic plant comprising a transgenic plant cell of the present disclosure.

A further aspect of the present disclosure relates to a polynucleotide construct comprising an inhibitory polynucleotide comprising a polynucleotide sequence that targets an endogenous glycolate transporter Plgg1 present in a plant cell, wherein when expressed in the plant cell, the inhibitory polynucleotide reduces expression of the endogenous glycolate transporter Plgg1 by about 20% to 80% of expression of endogenous glycolate transporter Plgg1 in a plant cell where the inhibitory polynucleotide is not present.

Another aspect of the present disclosure relates to a method for increasing biomass productivity in a plant. This method involves transforming a plant cell with one or more polynucleotides comprising a first promoter operably linked to a polynucleotide sequence encoding a glycolate dehydrogenase, a second promoter operably linked to a polynucleotide sequence encoding a malate synthase, and an inhibitory polynucleotide targeting an endogenous glycolate transporter Plgg1. Expression of the endogenous glycolate transporter Plgg1 in the transformed plant cell is about 20% to 80% of expression of endogenous glycolate transporter Plgg1 in a plant cell that is not transformed with an inhibitory polynucleotide targeting an endogenous glycolate transporter Plgg1 and said transforming increases biomass productivity of the plant.

Another aspect of the present disclosure relates to a transgenic plant cell culture produced by methods described herein.

A further aspect of the present disclosure relates to a method for increasing photosynthetic activity and stomatal conductance under drought conditions in a plant. This method involves transforming a plant cell with one or more polynucleotides comprising a first promoter operably linked to a polynucleotide sequence encoding a glycolate dehydrogenase, a second promoter operably linked to a polynucleotide sequence encoding a malate synthase, and an inhibitory polynucleotide targeting an endogenous glycolate transporter Plgg1, where expression of the endogenous glycolate transporter Plgg1 in the transgenic plant cell is about 20% to 80% of expression of endogenous glycolate transporter Plgg1 in a plant cell that is not transformed with an inhibitory polynucleotide targeting an endogenous glycolate transporter Plgg1. The method further involves regenerating a plant from the transformed plant cell, and subjecting the plant to drought conditions. Said transforming increases photosynthetic activity and stomatal conductance under drought conditions in the regenerated plant.

The present disclosure relates to compositions (e.g., polynucleotide constructs, transgenic plant cells, plants containing polynucleotide constructs and transgenic plant cells, and transgenic plant cell cultures) and methods for increasing photosynthesis efficiency and/or biomass productivity in plants. Also provided are compositions (e.g., polynucleotide constructs, transgenic plant cells, plants containing polynucleotide constructs and transgenic plant cells, and transgenic plant cell cultures) and methods for increasing photosynthetic activity and/or stomatal conductance in plants. In some embodiments, such plants are growing or are expected to grow under drought conditions.

Compositions and methods of the present disclosure are designed or engineered to induce glycolate metabolism and by inhibiting glycolate transport in the photorespiratory pathway, thereby decreasing the negative impact of photorespiration on plant growth and offsetting any slowdown in growth, which may be caused by incorporation of transgenic constructs into plants. The negative impact of photorespiration on the growth of plants, including tree plants, can be significantly decreased by engineering the plants to reduce the transportation of glycolate out of chloroplasts and to metabolize the retained glycolate to $CO_2$ for RuBisCo enzyme to fix inside chloroplasts.

Based on findings described in the Examples infra, the present disclosure provides compositions and methods to enhance biomass productivity and carbon uptake in plants by increasing their photosynthetic efficiency and reducing photorespiration losses, such that negative impacts on plant growth caused by photorespiration and introduction of transgenic constructs is reduced.

Moreover, the disclosed compositions and methods described herein make use of inhibitory polynucleotides to down-regulate, but not eliminate or severely reduce, the expression of the native chloroplast glycolate transporter Plgg1 in the photorespiratory pathway, thus limiting glycolate efflux from the chloroplasts. U.S. Patent Application Publication No. 2018/0258440 to Ort et al., co-expressed a malate synthase and glycolate dehydrogenase with an RNAi construct against glycolate transporter Plgg1 in tobacco plants, and showed that knockdown and knockout strains of glycolate transporter Plgg1 function similarly. However, as described herein, it is surprisingly shown that the down-regulation of endogenous glycolate transporter Plgg1 expression by about 80% or more compared to the normal, wild-type expression or expression level of glycolate transporter Plgg1 in a control plant, leads to severe detrimental morphological effects on plants when co-expressed with malate synthase and glycolate dehydrogenase. A reduction of endogenous glycolate transporter Plgg1 expression by less than 20% had little effect on phenotype. However, a more moderate reduction of endogenous expression levels of glycolate transporter Plgg1 (i.e., a plant having about 20% to about 80% of the expression level of glycolate transporter Plgg1 relative to a wild-type control plant) improved growth rate and biomass productivity.

The compositions and methods disclosed herein led to plants and forest trees with increased biomass productivity of at least 10-40% or more, as well as increased photosynthetic activity and stomatal conductance under drought conditions.

BRIEF DESCRIPTION OF THE DRAWINGS

FIG. 4 is a sequence alignment of *Populus alba* Plgg1 (PalbaPlgg1) (SEQ ID NO:38), *Populus Tremula* (Ptrem-Plgg1) (SEQ ID NO:39), and *Populus trichocarpa* Plgg1 (PtricPlgg1) (SEQ ID NO:6) coding regions, and the sense portion of the sequence used for RNAi (SEQ ID NO:8) in pLC0102.

FIGS. 13A-B relate to plant height analysis of four-month-old plants of selected events LC0102.13-15E, 5A, 7F, and 8-9A in comparison to non-transgenic control plants 717. Number of ramets: 13-15E, 2; 5A, 3; 7F, 3; 8-9A, 3; Control 717, 5. FIG. 13A is a photograph showing the height difference between events and controls. Blue arrow: LC0102 events; Red arrow: non-transgenic control. FIG. 13B is a graph showing the average plant height measured at 17 weeks post potting. The symbols * and ** represent a significant difference at $p<0.05$ and $p<0.01$, respectively, when compared to non-transgenic 717 plants. Statistical analysis was performed based on one-way ANOVA.

FIGS. 14A-B are graphs showing the average fresh weight (FIG. 14A) and average dry weight (FIG. 14B) biomass production after 21 weeks of growth in controlled environments. Number of ramets: Event 13-15E, 2; Event 7F, 3; Non-transgenic control CT717, 5. AG: Above ground biomass=Leaf+Stem. Symbols * and ** represent significant differences at $p<0.05$ and $p<0.01$, respectively, when compared with non-transgenic CT717. Statistical analysis was performed based on one-way ANOVA.

FIGS. 18A-C are graphs showing the relative expression levels of endogenous Plgg1 (FIG. 18A) and transgenes Glycolate Dehydrogenase (CrGDH) (FIG. 18B) and Malate Synthase (ChMS) (FIG. 18C) in various transgenic events and controls.

DETAILED DESCRIPTION

Figure 1:
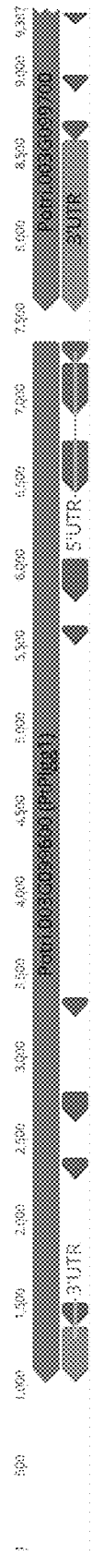
FIG. 1 is a schematic illustration of *Populus trichocarpa* PtPlgg1 in its endogenous genomic context.

The present disclosure relates to transgenic plant cells, transgenic plants, and methods for increasing biomass productivity, decreasing the negative impact of photorespiration, and increasing photosynthesis efficiency in plants.

Unless otherwise indicated, the definitions and embodiments described in this and other sections are intended to be applicable to all embodiments and aspects of the present disclosure herein described for which they are suitable as would be understood by a person of ordinary skill in the art.

Singular forms "a", "an", and "the" include plural references unless the context clearly dictates otherwise. Thus, for example, a reference to "a method" includes one or more methods, and/or steps of the type described herein and/or which will become apparent to a person of ordinary skill in the art upon reading the present disclosure.

The term "about" includes being within a statistically meaningful range of a value. Such a range can be within an order of magnitude, preferably within 0-10%, 10%, 5%, 4%, 3%, 2%, 1%, or at a given value or within a given range. The allowable variation encompassed by the term "about" depends on the particular context and as a person of ordinary skill in the art would appreciate.

The term "and/or" as used herein means that the listed items are present, or used, individually (e.g., as alternatives) or in combination. In effect, this term means that "at least one of" or "one or more" of the listed items is used or present.

In understanding the scope of the present disclosure, the term "comprising" and its derivatives, as used herein, are intended to be open ended terms that specify the presence of the stated features or method steps, but do not exclude the presence of other unstated features or method steps. The foregoing also applies to words having similar meanings such as the terms, "including", "involving", "having", and their derivatives. The term "comprising" may be substituted with the term "consisting of" to specify the presence of the stated features or method steps only and to exclude the presence of other unstated features or method steps. The term "comprising" may alternatively be substituted with the term "consisting essentially of" to specify the presence of the stated features or method steps as well as those that do not materially affect the basic and novel characteristic(s) of features or method steps as a person of ordinary skill in the art would appreciate.

As used herein, the term "coding region" is a portion of a nucleic acid, which is transcribed and translated into a polypeptide or protein.

As used herein, the term "conservative substitution" is a mutation in amino acid sequence where one or more amino acids is substituted by another amino acid having highly similar properties. Examples include, but are not limited to, one or more amino acids comprising nonpolar or aliphatic side chains, such as glycine, alanine, valine, leucine, isoleucine, or proline, which can be substituted for one another; one or more amino acids comprising polar, uncharged side chains, such as serine, threonine, cysteine, methionine, asparagine, or glutamine, which can be substituted for each other; one or more amino acids comprising aromatic side chains, such as phenylalanine, tyrosine, or tryptophan, which can be substituted for each other; one or more amino acids comprising positively charged side chains, such as lysine, arginine, or histidine, which can be substituted for each other; one or more amino acids comprising negatively charged side chains, such as aspartic acid or glutamic acid, which can be substituted for each other. For example, conservative substitutions for leucine include alanine, isoleucine, valine, phenylalanine, tryptophan, methionine, and cysteine, and conservative substitutions for asparagine include arginine, lysine, aspartate, glutamate, and glutamine. Conservatively modified nucleic acids include nucleic acids that encode identical or essentially identical amino acid sequences.

A "gene" refers to an assembly of nucleotides that encode a polypeptide, and includes cDNA and genomic DNA nucleic acids. "Gene" also refers to a nucleic acid fragment that expresses a specific functional RNA, protein, or polypeptide, optionally including regulatory sequences preceding (5' noncoding sequences) and following (3' noncoding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene, "heterologous" gene, or "exogenous" gene refers to a gene not normally found in the host organism, but that is introduced into the host organism by gene transfer. Heterologous genes can comprise native genes inserted into a non-native organism, or chimeric genes, such as a native gene under control of a different promoter than its endogenous promoter. A "transgene" is a gene that has been introduced into the genome by a transformation or transfection procedure.

"Heterologous" or "exogenous" DNA refers to DNA not naturally located in the cell, or in a chromosomal site of the cell. The heterologous DNA can include a gene or other polynucleotides foreign to the cell.

"Operably linked" means an association between polynucleotide (e.g., nucleic acid) sequences on a single nucleic acid molecule such that the function of one is affected by the other. For example, a promoter is operably linked to a coding sequence when the coding sequence is under the transcriptional control of the promoter. Coding sequences can be operably linked to regulatory sequences in sense or antisense orientation.

A "polypeptide" is a naturally occurring or synthetic peptide, oligopeptide, polypeptide, gene product, expression product, or protein comprising an amino acid sequence, where the amino acids are joined to each other by peptide bonds or modified peptide bonds.

A "promoter" refers to a nucleic acid fragment capable of controlling transcription of another nucleic acid fragment. A promoter is a non-coding genomic DNA sequence, usually upstream (5') to and operably linked to the relevant coding sequence, and its primary function is to act as a binding site for RNA polymerase to initiate transcription by the RNA polymerase. A promoter may also include distal enhancer or repressor elements, which can be located as much as several thousand base pairs from the start site of transcription. The terms "capable of controlling expression" or "initiating transcription", refer to the primary function of a promoter. Additionally, there is "expression" of RNA, including functional RNA, or the expression of polypeptide for operably linked encoding nucleotide sequences, as the transcribed RNA ultimately may be translated into the corresponding polypeptide. Promoters vary in their "strength" (i.e., their ability to promote transcription). The nucleotide sequence of the promoter determines the nature of the RNA polymerase binding and other related protein factors that attach to the RNA polymerase and/or promoter, and the rate of RNA synthesis.

A "constitutive" promoter is a promoter that is active under most environmental and developmental conditions. An "inducible" promoter is a promoter that is active under environmental or developmental regulation.

A "reference sequence" means a nucleic acid or amino acid used as a comparator for another nucleic acid or amino acid, respectively, when determining sequence identity. A reference sequence can be a wildtype sequence.

"Sequence identity," "percent identity," or "% identical" refers to the exactness of a match between a reference sequence and a sequence being compared to it when optimally aligned. For example, sequence alignments and percent identity calculations may be determined using a variety of comparison methods designed to detect homologous sequences including, but not limited to, the Multalin program (Corpet, "Multiple Sequence Alignment with Hierarchical Clustering," *Nucleic Acids Res.* 16:10881-90 (1988), which is hereby incorporated by reference in its entirety) or the Megalign® program of the LASERGENE® bioinformatics computing suite (DNASTAR® Inc., Madison, Wis.). Sequences may also be aligned using algorithms known in the art including, but not limited to, CLUSTAL V algorithm or the BLASTN or BLAST 2 sequence programs.

As used herein, the term "plant cell" includes cells, protoplasts, cell tissue cultures from which plants can be regenerated, calli, clumps, and cells that are intact in plants or parts of plants including, but not limited to seeds, leaves, stems, roots, vegetative buds, floral buds, meristems, embryos, hypocotyls, cotyledons, endosperm, sepals, petals, pistils, carpels, stamens, anthers, microspores, pollen, pollen tubes, ovules, nucellar tissue, ovaries, and other plant tissue or cells. In some embodiments, the plant cell is a protoplast.

"Transformation" or "transforming" refers to the introduction of a nucleic acid into a host organism. Host organisms containing a transformed polynucleotide construct or DNA fragment are referred to as "transgenic" or "recombinant" organisms. "Transfection" refers to the introduction of a nucleic acid, a protein, or both into a host organism. Thus, isolated polynucleotides disclosed herein can be incorporated into recombinant constructs, typically polynucleotide constructs, capable of introduction into and replication in a host cell. A construct can be a vector that includes a replication system and sequences that are capable of transcription and translation of a polypeptide-encoding sequence in a given host cell. Typically, expression vectors include, for example, one or more cloned genes under the transcriptional control of 5' and 3' regulatory sequences and a selectable marker. Such vectors also can contain a promoter regulatory region, such as a regulatory region controlling inducible or constitutive, environmentally- or developmentally-regulated, or tissue-specific expression, a transcription initiation start site, a ribosome binding site, a transcription termination site, and/or a polyadenylation signal.

The phrase "under conditions effective" is used to describe any environment that permits the desired reaction to take place.

A "vector" or "polynucleotide construct" is a nucleic acid, plasmid, or virus used to transfer coding information to a host cell. A "cloning vector" is a small piece of DNA into which a foreign DNA fragment is inserted to be transcribed. Typically the vector contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. The DNA sequence in the expression vector is operably linked to appropriate expression control sequences, including a promoter, to direct RNA synthesis and protein expression. The expression vector can contain one or more selectable marker genes to provide a phenotypic trait for selection of a transformed host cell. Useful selectable markers include dihydrofolate reductase or neomycin resistance for eukaryotic cell culture, or tetracycline or ampicillin resistance in *E. coli*. The vector may be introduced into the host cell(s) using any of a variety of techniques, including transformation, transfection, transduction, viral infection, gene guns, Ti-mediated gene transfer, calcium phosphate transfection, DEAE-Dextran-mediated transfection, lipofection, or electroporation. Examples of vectors include, but are not limited to, viral particles, baculovirus, phage, plasmids, phagemids, cosmids, fosmids, bacterial artificial chromosomes, viral DNA, such as vaccinia and adenovirus, P1-based artificial chromosomes, yeast plasmids, *Bacillus* vectors, and *Aspergillus* vectors. Examples of bacterial vectors include, but are not limited to, pQE vectors, pBluescript plasmids, pNH vectors, and lambda-ZAP vectors. Examples of eukaryotic vectors include pXT1, pSG5, pSVK3, pBPV, pMSG, and pSVLSV40 vectors. Suitable constitutive promoters that are functional in a plant cell include, but are not limited to, the cauliflower mosaic virus 35S (CaMV35S) promoter, a tandem 35S promoter, a cauliflower mosaic virus 19S promoter, a figwart mosaic virus 35S (FMV35S) promoter, a nopaline synthase gene promoter, an octopine synthase gene promoter, a potato or tomato protease inhibitor I or II gene promoter, and a ubiquitin promoter. Suitable inducible promoters that are functional in a plant cell may include, but are not limited to, a phenylalanine ammonia-lyase gene promoter, a chalcone synthase gene promoter, a pathogenesis-related protein gene promoter, a copper-inducible regulatory element, tetracycline, and chlor-tetracycline-inducible regulatory elements.

Preferences and options for a given aspect, feature, embodiment, or parameter of the disclosure should, unless the context indicates otherwise, be regarded as having been disclosed in combination with any and all preferences and options for all other aspects, features, embodiments, and parameters of the disclosure.

Compositions and Methods of Producing Photosynthesis-Efficient Plants

One aspect of the present disclosure relates to a transgenic plant cell comprising a first promoter operably linked to a polynucleotide sequence encoding a glycolate dehydrogenase, a second promoter operably linked to a polynucleotide sequence encoding a malate synthase, and an inhibitory polynucleotide targeting an endogenous (i.e., native) glycolate transporter Plgg1, where expression of the endogenous glycolate transporter Plgg1 in the transgenic plant cell is about 20% to 80% of expression of endogenous glycolate transporter Plgg1 in a plant cell that is not transformed with an inhibitory polynucleotide targeting an endogenous glycolate transporter Plgg1.

This aspect of the present disclosure can be carried out with any of the embodiments disclosed herein.

In the transgenic plant cell and other aspects of the present disclosure, glycolate dehydrogenase ("GDH") is an enzyme, such as glycolate dehydrogenase from *Chlamydomonas reinhardtii*, which oxidates glycolate into glyoxylate using organic co-factors instead of oxygen as electron acceptors. In some embodiments, the polynucleotide sequence encodes a bacterial glycolate dehydrogenase or an algae glycolate dehydrogenase, such as a glycolate dehydrogenase from *Chlamydomonas reinhardtii*.

In some embodiments, the polynucleotide sequence encodes glycolate dehydrogenase from *Chlamydomonas reinhardtii* ("CrGDH"), which has a coding sequence of SEQ ID NO:1 (GenBank Accession No. XM_001695329.2, which is hereby incorporated by reference in its entirety) as follows:

```
ATGCCACGCG GCCAGGGCAA GCGCCTGGCT CAGCTCCTTG GAGCTCAGCT GAAGCAGTAC

GCAGCGGAGG TGCGTGGCAT CAGCACAGCT GGTGGCGCTT CTCGCGGTGG AGCTCGAGGA

CCTGCATCCC CTAGCTCGCT AGAGCAGCAG ACGCGCCAGG TCGCTCAGGT TGCTGTTCAG

CAGTCGACTC AGCAGGCAGT GAAGGTCGTT GTGCCGGCCA TCAAAGTAGA CCTGGTTGGT

GCGGTCAGCT CGGTGTCTGA GAGCGACAAG GTGGAGCCGG GTGTGTTCAA GAACGTGGAT

GGCCACCGCT TCGAGGACGG TCGCTATGCC GCTTTTGTTG AGGAGATTAC AAAGTTTATC

CCCAAGGAGC GCCAGTACTC GGACCCCGTG CGCACATTCG CGTATGGCAC GGATGCCTCC

TTCTACCGGC TTAACCCGAA GCTGGTAGTG AAGGTGCACA ACGAGGACGA GGTCCGCCGC

ATCATGCCCA TCGCGGAGCG GCTGCAGGTC CCTATCACCT TCCGCGCGGC CGGCACGTCG

CTGTCTGGGC AGGCAATTAC CGACTCGGTG CTCATTAAGC TGAGCCACAC GGGCAAGAAC

TTCCGCAACT TTACCGTGCA CGGCGACGGT AGCGTGATCA CGGTGGAGCC GGGCCTCATT

GGCGGCGAGG TGAACCGCAT CCTGGCGGCA CACCAGAAGA AGAACAAGCT GCCCATCCAG

TACAAGATCG GACCCGACCC CTCCTCCATC GACAGCTGCA TGATCGGCGG CATCGTGTCC

AACAACAGCA GCGGCATGTG CTGCGGCGTG AGCCAGAACA CCTACCACAC GCTGAAGGAC

ATGCGGGTGG TGTTCGTAGA CGGAACGGTG CTGGACACGG CCGACCCCAA CTCGTGCACC

GCCTTCATGA AGAGCCACCG CTCGCTGGTG GATGGCGTCG TGAGCCTGGC GCGCCGCGTG

CAGGCCGACA AGGAGCTGAC GGCGCTCATC CGCCGCAAGT TCGCCATCAA GTGCACCACC

GGCTACTCCC TGAACGCGCT GGTGGACTTC CCGGTGGACA ACCCCATTGA GATCATCAAG

CACCTCATCA TCGGCAGCGA GGGCACGCTG GGCTTCGTCA GCCGCGCCAC CTACAACACC

GTGCCCGAGT GGCCCAACAA GGCCTCGGCC TTCATCGTGT TCCCGGACGT GCGCGCCGCC

TGCACCGGCG CCTCGGTGCT GCGCAACGAG ACGTCCGTGG ACGCGGTGGA GCTGTTTGAC

CGCGCCAGCC TGCGCGAGTG CGAGAACAAC GAGGACATGA TGCGCCTGGT GCCCGACATC

AAGGGCTGCG ACCCCATGGC GGCAGCGCTG CTGATCGAGT GCCGCGGCCA GGACGAGGCC

GCACTGCAGA GCCGCATTGA GGAGGTGGTG CGCGTGCTGA CGGCGGCGGG CCTGCCCTTC

GGCGCCAAGG CCGCGCAGCC CATGGCCATC GACGCCTACC CCTTCCACCA CGACCAGAAG

AACGCCAAGG TCTTCTGGGA CGTGCGCAGG GGCCTGATCC CCATTGTGGG CGCGGCGCGC

GAGCCCGGCA CATCCATGCT GATCGAGGAC GTGGCCTGCC CCGTGGACAA GCTGGCCGAC

ATGATGATCG ACCTGATCGA CATGTTCCAG CGCCACGGCT ACCACGACGC CTCCTGCTTC

GGCCACGCGC TCGAGGGCAA CCTTCACTTG GTGTTCTCGC AGGGCTTCCG CAACAAGGAG

GAGGTGCAGC GCTTCAGCGA CATGATGGAG GAGATGTGCC ACCTGGTGGC CACCAAGCAC
```

-continued

```
TCGGGCAGCC TCAAGGGCGA GCACGGCACG GGCCGCAACG TGGCGCCGTT CGTGGAGATG

GAGTGGGGCA ACAAGGCGTA CGAGCTGATG TGGGAGCTCA AGGCGCTGTT CGACCCCAGC

CACACCCTCA ACCCGGGCGT CATCCTCAAC CGCGACCAGG ACGCGCACAT CAAGTTCCTG

AAGCCCTCGC CCGCGGCCTC GCCCATCGTC AACCGCTGCA TCGAGTGCGG CTTCTGCGAG

TCCAACTGCC CCTCGCGCGA CATCACGCTC ACGCCGCGCC AGCGCATCTC CGTGTACCGC

GAGATGTACC GCCTCAAGCA GCTGGGCCCG GGCGCCAGCG AGGAGGAGAA GAAGCAGCTG

GCGGCCATGA GCAGCTCGTA CGCCTACGAC GGCGAGCAGA CGTGCGCGGC GGACGGCATG

TGCCAGGAGA AGTGCCCCGT CAAGATCAAC ACGGGAGACC TGATCAAGTC GATGCGTGCC

GAGCACATGA AGGAGGAGAA GACCGCCAGC GGCATGGCAG ACTGGCTGGC CGCCAACTTC

GGCGTCATCA ACTCCAACGT GCCGCGCTTC CTCAACATCG TCAACGCCAT GCACAGCGTG

GTGGGCTCGG CGCCTCTGTC CGCCATCAGC CGCGCGCTCA ACGCCGCCAC CAACCACTTC

GTGCCGGTGT GGAACCCCTA CATGCCCAAG GGCGCGGCGC CGCTCAAGGT GCCCGCCCCG

CCGGCGCCGG CAGCTGCTGA GGCCTCGGGC ATCCCGCGCA AGGTGGTGTA CATGCCCAGC

TGCGTGACGC GCATGATGGG CCCCGCCGCC TCCGACACCG AGACGGCGGC GGTGCACGAG

AAGGTGATGA GCCTGTTCGG CAAGGCCGGC TACGAGGTGA TCATCCCCGA GGGCGTGGCC

AGCCAGTGCT GCGGCATGAT GTTCAACAGC CGCGGCTTCA AGGACGCCGC CGCCAGCAAG

GGCGCGGAGC TGGAGGCGGC GCTGCTCAAG GCCTCGGACA ATGGCAAGAT CCCCATCGTC

ATCGACACCT CGCCCTGCCT GGCGCAGGTG AAGAGCCAGA TCAGCGAGCC GTCGCTGCGC

TTCGCGCTGT ACGAGCCGGT TGAGTTCATC CGGCACTTCC TGGTGGACAA GCTGGAGTGG

AAGAAGGTGC GCGACCAGGT GGCCATCCAC GTGCCCTGCT CCTCCAAGAA GATGGGCATC

GAGGAGTCCT TCGCGAAGCT GGCGGGCCTG TGCGCCAACG AGGTGGTGCC CTCGGGCATT

CCTTGCTGCG GCATGGCGGG CGACCGCGGC ATGCGCTTCC CCGAGCTGAC CGGCGCCTCG

CTGCAGCACC TCAACCTGCC CAAGACCTGC AAGGACGGCT ACTCCACCAG CCGCACCTGC

GAGATGTCGC TCAGCAACCA CGCCGGCATC AACTTCAGGG GCCTGGTGTA CCTGGTGGAT

GAGGCCACGG CGCCTAAGAA GCAGGCCGCC GCTGCCAAGA CCGCGTAA
```

The amino acid sequence for CrGDH (SEQ ID NO:2) (GenBank Accession No. XP_001695381.1, which is hereby incorporated by reference in its entirety) is as follows:

```
MPRGQGKRLA QLLGAQLKQY AAEVRGISTA GGASRGGARG PASPSSLEQQ TRQVAQVAVQ

QSTQQAVKVV VPAIKVDLVG AVSSVSESDK VEPGVFKNVD GHRFEDGRYA AFVEEITKFI

PKERQYSDPV RTFAYGTDAS FYRLNPKLVV KVHNEDEVRR IMPIAERLQV PITFRAAGTS

LSGQAITDSV LIKLSHTGKN FRNFTVHGDG SVITVEPGLI GGEVNRILAA HQKKNKLPIQ

YKIGPDPSSI DSCMIGGIVS NNSSGMCCGV SQNTYHTLKD MRVVFVDGTV LDTADPNSCT

AFMKSHRSLV DGVVSLARRV QADKELTALI RRKFAIKCTT GYSLNALVDF PVDNPIEIIK

HLIIGSEGTL GFVSRATYNT VPEWPNKASA FIVFPDVRAA CTGASVLRNE TSVDAVELFD

RASLRECENN EDMMRLVPDI KGCDPMAAAL LIECRGQDEA ALQSRIEEVV RVLTAAGLPF

GAKAAQPMAI DAYPFHHDQK NAKVFWDVRR GLIPIVGAAR EPGTSMLIED VACPVDKLAD

MMIDLIDMFQ RHGYHDASCF GHALEGNLHL VFSQGFRNKE EVQRFSDMME EMCHLVATKH

SGSLKGEHGT GRNVAPFVEM EWGNKAYELM WELKALFDPS HTLNPGVILN RDQDAHIKFL

KPSPAASPIV NRCIECGFCE SNCPSRDITL TPRQRISVYR EMYRLKQLGP GASEEEKKQL
```

```
AAMSSSYAYD GEQTCAADGM CQEKCPVKIN TGDLIKSMRA EHMKEEKTAS GMADWLAANF

GVINSNVPRF LNIVNAMHSV VGSAPLSAIS RALNAATNHF VPVWNPYMPK GAAPLKVPAP

PAPAAAEASG IPRKVVYMPS CVTRMMGPAA SDTETAAVHE KVMSLFGKAG YEVITPEGVA

SQCCGMMFNS RGFKDAAASK GAELEAALLK ASDNGKIPIV IDTSPCLAQV KSQISEPSLR

FALYEPVEFI RHFLVDKLEW KKVRDQVAIH VPCSSKKMGI EESFAKLAGL CANEVVPSGI

PCCGMAGDRG MRFPELTGAS LQHLNLPKTC KDGYSTSRTC EMSLSNHAGI NFRGLVYLVD

EATAPKKQAA AAKTA
```

In some embodiments, the polynucleotide sequence encodes glycolate dehydrogenase from *Chlamydomonas reinhardtii* (CrGDH) having an amino acid sequence of SEQ ID NO:2. In some embodiments, the polynucleotide sequence encodes glycolate dehydrogenase having an amino acid sequence that is at least 80% identical to the amino acid sequence of CrGDH of SEQ ID NO:2. In some embodiments, the polynucleotide sequence encodes glycolate dehydrogenase comprising an amino acid sequence that is at least 80%, 83%, 85%, 90%, 91%, 92%, 93%, 94% 95%, 96%, 97%, 98%, 99%, or 100% identical to the amino acid sequence of CrGDH of SEQ ID NO:2. Additional exemplary glycolate dehydrogenase sequences that may be encoded by the polynucleotide sequence encoding a glycolate dehydrogenase are shown in Table 9 infra.

The transgenic plant cell and other aspects of the present disclosure also make use of the enzyme malate synthase ("MS"), such as malate synthase from the plant genus *Cucurbita*, which converts glyoxylate to malate, with consequent release of carbon dioxide in the chloroplast without causing toxic accumulation of ammonia. In some embodiments, the polynucleotide sequence encoding malate synthase encodes malate synthase from a plant of the genus *Cucurbita*. In some embodiments, the polynucleotide sequence encoding malate synthase encodes a malate synthase from the species *Cucurbita hybrida* (ChMS), such as *Cucurbita* sp. *Kurokawa Amakuri Nankin*. The coding sequence for one embodiment of the enzyme MS, ChMS (SEQ ID NO:3) (GenBank Accession No. X56948.1, which is hereby incorporated by reference in its entirety) is as follows:

```
ATGGGATCGC TGGGAATGTA TTCTGAATCG GCAGTAAGGA AGAAAAGTAG CCGAGGCTAC

GATGTTCCAG AGGGAGTGGA CATTCGGGGA CGTTATGATG AAGAATTTGC CAGGATTCTC

AACAAGGAAG CCTTGCTGTT TGTGGCTGAT TTACAGAGGA CTTTCAGAAA CCACATAAGG

TATTCGATGG AATGCCGCAG AGAAGCCAAA AGGAGGTACA ATGAAGGGGC GGTGCCGGGG

TTTGATCCGG CGACCAAGTA TATAAGGGAA TCTGAGTGGA CATGTGCATC AGTCCCCCCG

GCAGTTGCTG ATCGGAGAGT GGAGATCACC GGACCTGTGG AGCGGAAGAT GATCATCAAC

GCACTCAATT CTGGAGCTAA AGTTTTCATG GCGGACTTTG AAGATGCACT ATCACCAAAC

TGGGAGAATT TGATGAGGGG GCAAATTAAT CTGAAGGATG CAGTTGATGG ACTATAAGC

TTCCATGACA AAGCTAGAAA CAAGGTTTAT AAACTGAACG ATCAGACAGC CAAGCTCTTT

GTTCGCCCTC GAGGTTGGCA CTTCGCTGAG GCTCATATCT TCATCGACGG CGAGCCTGCC

ACCGGCTGTC TTGTGGACTT CGGGCTCTAC TTTTTTCACA ACCATGCCAA TTTCCGGCGC

TCTCAAGGTC AAGGTTCTGG CCCTTTCTTT TACCTTCCCA AAATGGAGCA CTCCAGGGAA

GCAAAAATAT GGAACAGTGT ATTTGAGAGA GCAGAGAAGA TGGCAGGGAT AGAGAGGGGC

AGCATCAGGG CCACTGTGCT GATTGAAACA CTTCCAGCAG TGTTTCAAAT GGATGAAATA

CTCTATGAGC TGAGGGATCA TTCTGTGGGA TTGAACTGTG GTAGATGGGA TTACATATTC

AGCTATGTCA AGACCTTCCA GGCTCACCTA GATCGCCTGT TACCCGACCG AGTCCAAGTC

GGTATGGCAC AACATTTCAT GAGGAGTTAT TCTGATCTCC TTATCAGGAC TTGTCACACG

GTGGTGTGCC ACGTGGGAGG CATGGCTGCT CAAATTCCAA TTAGAGACGA CCCGAAGGCA

AATGAGATGG CACTTGAGCT AGTGAGGAAG GACAAATTGA GAGAGGCAAA GGCAGGACAT

GATGGAACAT GGGCAGCACA TCCAGGATTA ATCCCAGCAT GTATGGAAGT CTTCACCAAC

AGCATGGGAA ATGCCCCCAA TCAGATCCGA TCTGCAAGAC GAGACGATGC TGCAAACCTA

ACTGAAGACG ACCTCTTGCA GCAACCGAGG GGTGTTCGTA CATTGGAAGG GCTCCGGTTG
```

-continued

```
AACACCCGAG TCGGAATTCA GTACCTAGCA GCATGGCTAA CCGGGACAGG CTCTGTGCCT

CTCTACAACC TTATGGAAGA TGCAGCCACA GCTGAAATCA GCAGGGTTCA AAACTGGCAA

TGGCTGAAGT ATGGAGTGGA ATTGGATGGA GATGGGCTTG GAGTGAGAGT GAACAAGGAA

CTGTTCGCAA GAGTGGTGGA AGAAGAAATG GAAAGGATTG AAAGAGAAGT GGGGAAGGAG

AAATTCAGGA AGGGAATGTA CAAAGAGGCT TGCAAGATGT TCACAAGGCA ATGCACAGCG

CCAACCTTGG ATGATTTTCT GACCTTGGAT GCGTACAACC ACATAGTCAT ACATCATCCC

AGGGAGCTGT CCAGGCTCTG A
```

The amino acid sequence for ChMS (SEQ ID NO:4) (GenBank Accession No. CAA40262, which is hereby incorporated by reference in its entirety) is as follows:

```
MGSLGMYSES AVRKKSSRGY DVPEGVDIRG RYDEEFARIL NKEALLFVAD LQRTFRNHIR

YSMECRREAK RRYNEGAVPG FDPATKYIRE SEWTCASVPP AVADRRVEIT GPVERKMIIN

ALNSGAKVFM ADFEDALSPN WENLMRGQIN LKDAVDGTIS FHDKARNKVY KLNDQTAKLF

VRPRGWHFAE AHIFIDGEPA TGCLVDFGLY FFHNHANFRR SQGQGSGPFF YLPKMEHSRE

AKIWNSVFER AEKMAGIERG SIRATVLIET LPAVFQMDEI LYELRDHSVG LNCGRWDYIF

SYVKTFQAHL DRLLPDRVQV GMAQHFMRSY SDLLIRTCHT VVCHVGGMAA QIPIRDDPKA

NEMALELVRK DKLREAKAGH DGTWAAHPGL IPACMEVFTN SMGNAPNQIR SARRDDAANL

TEDDLLQQPR GVRTLEGLRL NTRVGIQYLA AWLTGTGSVP LYNLMEDAAT AEISRVQNWQ

WLKYGVELDG DGLGVRVNKE LFARWEEEM ERIEREVGKE KFRKGMYKEA CKMFTRQCTA

PTLDDFLTLD AYNHIVIHHP RELSRL
```

In some embodiments, the polynucleotide sequence encodes malate synthase from *Cucurbita hybrida* (ChMS) having an amino acid sequence of SEQ ID NO:4. In some embodiments, the polynucleotide sequence encodes MS having an amino acid sequence that is at least 80% identical to the amino acid sequence of ChMS of SEQ ID NO:4. In some embodiments, the polynucleotide sequence encodes malate synthase comprising an amino acid sequence that is at least 80%, 83%, 85%, 90%, 91%, 92%, 93%, 94% 95%, 96%, 97%, 98%, 99%, or 100% identical to the amino acid sequence of ChMS of SEQ ID NO:4. Additional exemplary malate synthase sequences that may be encoded by the polynucleotide sequence encoding malate synthase are shown in Table 9 infra.

As noted above, the polynucleotide sequences encoding a glycolate dehydrogenase or a malate synthase are operably linked to a promoter. Exemplary promoters suitable for use include those that are inducible, viral, synthetic, or constitutive, all of which are well known in the art.

Non-limiting examples of promoters that may be useful in particular embodiments include the parsley ubiquitin promoter (Kawalleck et al. (1993) *Plant Mol Biol* 21: 673-684), which is hereby incorporated by reference in its entirety), *Arabidopsis* HSP70 promoter (Sung et al. (2001) *Plant Physiol* 126: 789-800, which is hereby incorporated by reference in its entirety), nopaline synthase (NOS) promoter (Ebert et al. (1987) *Proc. Natl. Acad. Sci.* USA 84(16):5745-9, which is hereby incorporated by reference in its entirety); the octopine synthase (OCS) promoter (which is carried on tumor-inducing plasmids of *Agrobacterium tumefaciens*); the caulimovirus promoters such as the cauliflower mosaic virus (CaMV) 19S promoter (Lawton et al. (1987) *Plant Mol. Biol.* 9:315-24, which is hereby incorporated by reference in its entirety); the CaMV 35S promoter (Odell et al. (1985) *Nature* 313:810-2; U.S. Pat. Nos. 5,322,938, 5,352,605, 5,359,142, and 5,530,196, which are hereby incorporated by reference in their entirety); the figwort mosaic virus 35S (FMV35S) promoter (Walker et al. (1987) *Proc. Natl. Acad. Sci. USA* 84(19):6624-8; U.S. Pat. Nos. 6,051,753, and 5,378,619, which are hereby incorporated by reference in their entirety); the sucrose synthase promoter (Yang and Russell (1990) *Proc. Natl. Acad. Sci. USA* 87:4144-8, which is hereby incorporated by reference in its entirety); the R gene complex promoter (Chandler et al. (1989) *Plant Cell* 1:1175-83, which is hereby incorporated by reference in its entirety); the chlorophyll a/b binding protein gene promoter; a PCl SV promoter (U.S. Pat. No. 5,850,019, which is hereby incorporated by reference in its entirety); the SCP1 promoter (U.S. Pat. No. 6,677,503, which is hereby incorporated by reference in its entirety); and AGRtu.nos promoters (GenBank Accession No. V00087; Depicker et al. (1982) *J. Mol. Appl. Genet.* 1:561-73; Bevan et al. (1983) *Nature* 304:184-7, which are hereby incorporated by reference in their entirety).

In some embodiments, a promoter may comprise a tissue-specific promoter. A tissue-specific promoter is a nucleotide sequence that directs a higher level of transcription of an operably linked nucleic acid in the tissue for which the promoter is specific, relative to the other tissues of the organism. Examples of tissue-specific promoters include, without limitation: tapetum-specific promoters; anther-specific promoters; pollen-specific promoters (see, e.g., U.S. Pat. No. 7,141,424, and PCT International Patent Publication No. WO 99/042587, which are hereby incorporated by reference in their entirety); ovule-specific promoters (see, e.g., U.S. Patent Application No. 2001/047525 A1, which is hereby incorporated by reference in its entirety); fruit-specific promoters (see, e.g., U.S. Pat. Nos. 4,943,674, and 5,753,475, which are hereby incorporated by reference in their entirety); and seed specific promoters (see, e.g., U.S. Pat. Nos. 5,420,034, and 5,608,152, which are hereby incorporated by reference in their entirety). In some embodiments, a developmental stage-specific promoter (e.g., a promoter active at a later stage in development) may be used to control expression of a polynucleotide.

In some embodiments, the polynucleotide sequence encoding a glycolate dehydrogenase is operably linked to a first promoter. In some embodiments, the first promoter is a constitutive promoter. In some embodiments, the constitutive promoter is an Act2 (actin 2) promoter or a Cauliflower mosaic virus 35S promoter. In some embodiments, the first promoter is a suppressor-mutator (Spm) transposable element promoter.

In some embodiments, the polynucleotide sequence encoding a malate synthase is operably linked to a second promoter. In some embodiments, the second promoter is a constitutive promoter, such as an Act2 promoter, or a Cauliflower mosaic virus 35S promoter. In some embodiments, the second promoter is a suppressor-mutator (Spm) transposable element promoter.

In some embodiments, the polynucleotide sequence encoding the glycolate dehydrogenase is operably linked to a chloroplast-targeting signal sequence at the amino-terminus. In some embodiments, the polynucleotide sequence encoding a malate synthase is operably linked to a chloroplast-targeting signal sequence at the amino-terminus.

In some embodiments, the chloroplast-targeting signal sequence encodes a ribulose-1,5-bisphosphate carboxylase-oxygenase (RuBisCO) small subunit RbcS signal sequence.

The transgenic plant cell and other aspects of the present disclosure also comprise an inhibitory polynucleotide targeting an endogenous glycolate transporter Plgg1 to reduce its expression. Methods for reducing gene expression involving the expression of DNA sequences in plants are known in the art, and include, but are not limited to, cosuppression, antisense suppression, double-stranded RNA (dsRNA) interference, hairpin RNA (hpRNA) interference, intron-containing hairpin RNA (ihpRNA) interference, transcriptional gene silencing, and micro RNA (miRNA) interference.

For example, an "inhibitory polynucleotide" may be an antisense polynucleotide or an RNA inhibitor (RNAi) polynucleotide capable of down-regulating gene expression of a native or endogenous chloroplast glycolate transporter Plgg1 in the photorespiratory pathway, thus limiting glycolate efflux from chloroplasts in the transgenic plant cell.

RNA interference (RNAi) occurs when an organism recognizes double-stranded RNA molecules and hydrolyzes them. The resulting hydrolysis products are small RNA fragments of 19-24 nucleotides in length, called small interfering RNAs (siRNAs) or microRNAs (miRNAs). The siRNAs then hybridize to mRNAs (or other RNAs) and cause hydrolysis of the RNA. Most plant miRNAs show extensive base pairing to, and guide cleavage of their target mRNAs.

The RNAi pathway can be exploited in plants by using recombinant technology, which entails transforming a plant with a vector comprising DNA that when expressed produces a dsRNA homologous or nearly homologous to a gene target. The gene target can be homologous to an endogenous plant RNA. RNA interference in plants can also be referred to as post-transcriptional gene silencing or RNA silencing, and can be triggered by expression of an antisense strand of a target sequence of interest. In general, a plant is transformed with DNA that is incorporated into the plant genome, and when expressed produces a dsRNA that is complementary to a gene of interest, which can be an endogenous plant gene, leading to the reduction or elimination of expression of that gene.

In some embodiments, the inhibitory polynucleotide is an RNAi polynucleotide comprising a sense polynucleotide strand comprising at least 20 contiguous nucleotides from a glycolate transporter Plgg1 sequence, and an antisense polynucleotide strand that hybridizes to the sense polynucleotide strand, where the sense and the antisense polynucleotide strand form a duplex. In some embodiments, the RNAi polynucleotide comprises a sense polynucleotide strand comprising at least 20, 30, 40, 50, 60, 70, 80, 90, 100, 200, 300, 400 or more than 400 contiguous nucleotides from a glycolate transporter Plgg1 sequence, and an antisense polynucleotide strand that hybridizes to the sense polynucleotide strand, wherein the sense and the antisense polynucleotide strand form a duplex. In some embodiments, the RNAi polynucleotide comprises a sense polynucleotide strand 20-400 contiguous nucleotides from a glycolate transporter Plgg1 sequence, and an antisense polynucleotide strand that hybridizes to the sense polynucleotide strand, wherein the sense and the antisense polynucleotide strand form a duplex.

RNAi constructs may also include a polynucleotide sequence that separates the sense and antisense strands to facilitate duplex formation. In some embodiments, the RNAi polynucleotide further comprises a polynucleotide sequence heterologous to the sense and antisense polynucleotides. In some embodiments, the RNAi polynucleotide comprises an intron. In some embodiments, the RNAi polynucleotide comprises a PDK intron.

In some embodiments, the inhibitory polynucleotide comprises an antisense polynucleotide. In some embodiments, the inhibitory polynucleotide comprises an antisense polynucleotide of a glycolate transporter Plgg1 coding sequence of at least 20 base pairs (bp), 25 bp, 30 bp, 35 bp, 40 bp, 45 bp, 50 bp, 55 bp, 60 bp, 65 bp, 70 bp, 75 bp, 80 bp, 85 bp, 90 bp, 95 bp, 100 bp, 125 bp, 150 bp, 175 bp, 200 bp, 300 bp, 400 bp, 500 bp, 600 bp, 700 bp, 800 bp, 900 bp, or greater than 1000 bp, or any number of base pairs or range of base pairs between 20 bp and 1000 bp.

In some embodiments, the glycolate transporter Plgg1 is selected from the group consisting of the genus *Populus, Eucalyptus, Pinus, Quercus, Pseudotsuga, Picea,* and *Ficus,* meaning that the transgenic cell is a cell of a plant of the genus *Populus, Eucalyptus, Pinus, Quercus, Pseudotsuga, Picea,* or *Ficus,* and the inhibitory polynucleotide targeting glycolate transporter Plgg1 targets glycolate transporter Plgg1 native or endogenous to a plant of the genus *Populus, Eucalyptus, Pinus, Quercus, Pseudotsuga, Picea,* or *Ficus.* In some embodiments, the glycolate transporter Plgg1 is from the genus *Populus,* meaning that the transgenic cell is a cell of a plant of the genus *Populus* and the inhibitory polynucleotide targeting glycolate transporter Plgg1 targets glycolate transporter Plgg1 native or endogenous to a plant of the genus *Populus.*

In some embodiments, the glycolate transporter Plgg1 is selected from the group consisting of the species *Populus tremula* x *Populus alba, Populus alba, Populus tremula, Populus trichocarpa, Populus euphratica,* and *Populus tremuloides,* meaning that the transgenic cell is a cell of a plant of the species *Populus tremula* x *Populus alba, Populus alba, Populus tremula, Populus trichocarpa, Populus euphratica,* or *Populus tremuloides* and the inhibitory polynucleotide targeting glycolate transporter Plgg1 targets glycolate transporter Plgg1 native or endogenous to one or more of the species *Populus tremula* x *Populus alba*, *Populus alba*, *Populus tremula*, *Populus trichocarpa*, *Populus euphratica*, or *Populus tremuloides*.

There is natural variation in the genetic sequence of the native chloroplast glycolate transporter Plgg1 coding sequences of different *Populus* varieties. In some embodiments, an inhibitory polynucleotide can reduce expression of glycolate transporter Plgg1 from different species. For example, FIG. 4 shows sequence variation between Plgg1 coding sequences of *Populus trichocarpa*, *Populus tremula*, and *Populus alba*. Even so, an inhibitory polynucleotide RNAi construct with *Populus trichocarpa* Plgg1 is able to reduce gene expression of Plgg1 in a *Populus tremula* x *Populus alba* hybrid (see Examples 1-11).

In some embodiments, the plant cell comprises two or more inhibitory polynucleotides targeting one or more endogenous glycolate transporter Plgg1 genes. For example, in a hybrid plant having two different endogenous glycolate transporter Plgg1 genes (one from each parent), it may be advantageous to use two inhibitory polynucleotides, each targeting and reducing the expression of a different endogenous glycolate transporter Plgg1 genes. Alternatively, it may be advantageous to have two or more inhibitory polynucleotides targeting the same endogenous glycolate transporter Plgg1 genes.

In some embodiments, the glycolate transporter Plgg1 is from the genus *Pinus*, meaning that the transgenic cell is a cell of a plant of the genus *Pinus* and the inhibitory polynucleotide targeting glycolate transporter Plgg1 targets glycolate transporter Plgg1 native or endogenous to a plant of the genus *Pinus*. In some embodiments, the glycolate transporter Plgg1 is from the species *Pinus taeda*, meaning that the transgenic cell is a cell of a plant of the species *Pinus taeda* and the inhibitory polynucleotide targeting glycolate transporter Plgg1 targets glycolate transporter Plgg1 native or endogenous to a plant of the species *Pinus taeda*.

In some embodiments, the inhibitory polynucleotide targeting an endogenous glycolate transporter Plgg1 comprises a polynucleotide sequence from *Populus trichocarpa* ("PtPlgg1").

The genomic sequence of PtPlgg1 (SEQ ID NO:5) Potri.003G099600 (Chromosome 3:12562661-12568870, of the *Populus trichocarpa* genome (popgenie.org), which is hereby incorporated by reference in its entirety) is as follows, with the coding sequence indicated in bold font:

ATGGCTACTC CTTTAGTCGC TCATTCCGTT CAGCTCTGTC ATCACCACTC AAAACAATAT

TCTTTCAAAT CACAATCACG TGTCAATAGG GATATCGGTA CAAAAACACT ACTTGGTGTT

TACAATGGAT TCCACAATGT ATATAACCAA TCTTATTTTC ATAAGCCTTG GGCACCCATT

AGAGTTCTTG AGCCTAATTC AAGGTTCTTG CAAATGGGTC CTCAAGAAAC CTGCTCTAGT

CGAGGAATTT CCAAGAAATC TATGAGCTCA GAAGGCAGTA CCAGTACTAG CTCTTCATCT

ATTTCTCAAC AGGTTAGTAT AAAGGTTTTA CTGTTTTTCT TTTTTGCACT CCTTTTTATT

TTTTTTTATG CTTTCCTGTT TTGTATGATT TCTACTAATT GGTATTGAGT TGTTGCATTT

AATTAAGCTG ATTCAACTAT TTGATTTACC TCCTTTTTAT ATTGATTGCA TAAGGTGATT

GGGATCTTGC ATTTGCTTGT TTCACTTGGG ATTATCCTTG CAATGGATAA GTTGTTGAAA

AAGGCATTTG TGGCTGCTGC TATCAAGTTT CCAAGTGCTC TGTTTGGCAT GTTCTGCATA

TTCTCAGTTT TAGTCATTCT TGATATAACT ATTCCGGCTG CTGCAACAAG CTTAATGAAC

TTCTTTCAGC CAGCACTGTT ATTCATTCAG AGATGGCTTC CGTTGTTCTA CGTTCCATCA

TTGGTTGTTT TGCCTCTCTC TGTTAAAGAT ATCCCTGCTG CATCAGGTGT CAAGATTTGC

TTCATCACAG GTAAAACGAA GCTTTTTGTT GATTCATTGC TTTTCACTCT CTAAATCTTT

AATATAGTTG GCTTGATGAA TAAAATGTCA CTATGAATTT GTGATAATCA CACATAATTA

ATGTTATCTA TTGAAATCAC AGAAATTACT GCAAGCTCAA AAGCCAAGAT AACATAGCAT

CTCCTTCATT CTCCTTATGT TTCAAGTTTT TTGCTGACCA TTTCATTATT CATATCTCCG

ATTCCAATGG CCACCATTTT TTTTCTCACT TTGGTCATTA TTCATATACC ATCCAGTCAG

CATTCCCATG TTTACTTCCA TTTTGGTGGG ACTATTTTTC AAGTTGTGTT TTGCAATTGT

AATAAATAAT AATAATAATG ATGATACAAA TGCTTTCTAA TAACTGCAGC TGGAGGGTGG

TTGGCGTCAC TTTGTGTGGC GGGTTTTACA GCTATTGCTG TGAGAAAAAT GGTGAAGACA

GAAATGACTG ATGCTGAGCC TATGGCGAAA CCCTCTCCTT TTTCTCCATT GGAAATATGG

GCTTGGAGTG GGGTCTTCCT TGTATCATTT GTTGTCGCAT TATTATATAG AACGGCATTA

GGGACTGCAG CCAGAACATG CCTTCCTTTC CTACTAGCGT CCACCGTGCT AGGCTATATG

GTTGGTTCTG GGTAAAATCT CAGTTTCCTC AGATTAGCAA CCTCTGTGTT GACAATTGTT

```
TTCCAGACCA AATTGACGAG GAATGGAATT GTTGCACACA TTCATTATAA TTGTAGCCCA

GTTAAAAAAT CATGGCTTTA CTCTTCTGGT TTTCAGGTTA CCATCTGGTG TTAAGAAGGT

TTTCCATCCC ATTATTTGTT GTGCACTATC TGCAGATTTG GCAGCGTTGG CCTTTGGGTT

CCTTTCCCAA TCTGGACTCG ATCCCGTTCT AGGTACCACT TTTCAAAGTG TTTGCTGTCT

TCATTTAGTT CACTCATTTT CTGATGTGGA GCAACAACAA ATGACAACAA TTGTTACTAC

AAAATGCCTG TATTATTTTG TTCCACAAGC CATCTCTTGC TTTTCCTTTC TATCATATGT

GTTAGTTTCC ATTATGTATT ATGTTTCCTT CTGATACATG TAGTGTTAGT AGAGAACAAA

ACCTGGAGGG GCCATTTCAG GCAGTTTCCA TTGACAAACT TAGGTAGTGT TTGGTATTCC

GAACAAAGAT GGACCGGATA TGACAATATT TTTTGTGAAG TTGTTTTGTG TACTTTTGAA

TAGTACAAAA ATCAATTTTT ATCTTGTCCA AAGCTGTTCT AGTAGAGAAA ATTGTCTCAT

TAGAAGGGGT AGAACAACCT TGTCTAGTTC CTTGCAGAAG AGTTAACTTA GGTTGATCCG

AATCAGCATA AATAAAAAT AGTTATTGTT ATAGTTATAG TTTTAAACTT GACTAGAGAG

TTGACTCAGG GCAAAGTTTG GGTTACGGAT TAGGTTGACT ATTGACTCAA GTCAATGTAA

GGATAAAAAT GTTTATTATC GTAGTTTTAA AACTTGACTT AGGGTCGAAC CGGGGCAAAG

CCCCGATCAC GGGTCGGGTT GAGTATTGAT CTAGGTCAAT GTAAGGATAA AATTATTGTT

ATCATAGCTT TAAAACCTGA CTAGGGGGTT GACCCGGGTC ACGGGTTGGT TGACCATTGA
GCCGAGTCAA CGTAAAGATA AAATGATTA TTATCACAGT TTTAAAACCT GATTTAGGAG

TTGACCTGGG ATAAGACCTA AGTCACAGGT TGAGATGATT ATTGAACAAG GTCAATGTAA

AGATAAAAGT GTTTATTATT ATAGTTTTAA AGTCTAACTA GGAGGTCAAC TCGGGTAAAG

TCCCTGTCAC AGGTTTGGTT AACCATTGAC CCAGGTCAAT ATAAAGATAA AAGTAGCTTG

AGTTACAAGT CGGGTTGACC ATTGATCTGA GTTAATGTAA GGATAAAAAT AGTTATTATC

ATAGTATTAA AACTCGACTA GGAGATCGAC CTGAGGTAAG ACCCATGTCA CGGGTCGAGA

TGGTCAACTT GTTTTGACCC AAGATAACGT AAGAGTAAGA ATAATTATTA TCAAAATTTT

AAAATCCGAC TCGAGGTTCA GCTTGAGTCA TGGGTTGGGA GGGTTAACGT AAGAATAAAA

ATGATTATTA TTATAATTTT AAAACTCAAT TTAAAGGTCG ATCCGGGGCA AGGCCTGAGT

TATGGGTTGA GATGGTCAGC TTGGGTTGAC TTAGGTCAAT ATATAGATAA AAATAGTTAT

TATCATAATT TTAAAACCTA ACTTGGGGGT CGACCTGGGG CAAGGTTTGA GTCTTAAGAT

GAGAGGGTCA ACCTAAGTTG ACAAAATATT TTGTTTTTTA AAAAAATCAA ACAATTTTG

TTTTATAAAA AAAAATAAAA AAAGTCAAAA GGATTTCTTA GCCTTGTTTT ATCTTGGGTC

GCAAGTCGAC CTGATTTTTT AACCGAGTAG GGTCGGATCA ATTGTTTCTT TATTTTTCT

CAAACTTAGA TTAGTCCAAT TCTTGTGTCA GTCGGGTCTC ATCCGGTATC TACCAAACAC

GAAATAAAT AAATTGTCTA GTTCAATTCA AAGCACACTA AATACAAAAA CAAACAATT

ATTTGTCGAG TCCAATTAAT ATTGTCTAGC ATACCAAACA CTACCCTACC ACTCATAGCC

TTTGTGCAAA ATGTTGAGGG ACCTCGAACG TTTTATTTAT TGCATCACTT GTGCTAATAC

TGTTTTGTCA ATGATAAAAA AGATGGTTAT TTATGATCTA ATGATGAACA CTTCTATAAT

TCAAAACTGA AGTTAACTGA TATATAGTTT TACAAATATT TTGGACAACA TTTTTTAAAT

TTCAGGGATG AAAATCTTAA AGTTCAAAAG CCGTTTTGAT CTAGTTTCTG TTGGAATTCA

AATCACATAC CATGTGAACT CCCTCTTTTT TCCTCCATCC TTCTCTATGG TCACATTTTT

TTCATTAAGT TTTTTCATAT CTATTTTTAA GCTCATTTTC TGTACTTCCT CATTGTAGTT

ATGGTAATTT TCTTCCAATG CACACAGGAT ATTACCTTAC AAAAGTTTCA TCTAATCCTG

GAGCTGGTGA TGTGTTAATG GGATTCTTGG GACCTGTCAT TCTTTCTTTT GCCTTCTCAA
```

-continued

TGTTCAAGCA GCGAAAGGTA ACTTCTTTTC TCACAATCCA TGCCAACAGG TCGGGTTCAT

TTTGTATTAA GTGGATATGT TTCATCTGTG CTGTTACTCA GGAAGGACTA GGGGTTCCTT

TTATTTAATT GTAACTATTT GGTGTTGCCA ACCAAACTAT CTGGTGTTGC CAACCAAACT

ATCTGCTATA CATTATTTTT TTTCATTTGG TAATGGAAGA CGATGCGTTT GAAATTCAGA

GTAGAGAATA AGCAATGAAA AACCTCAAAA TATTTAGACC TTGCAAGAAT CTAGGAATCT

AGAATATTGC ATCTACCTTT ATATGAATTT ATCCTCAGTA GTATTCTATG TATGCTTTGT

CATTACATGG TTTGTTGTCC TCGATTCAGA ATAATAAAAA TTTGTCATCA GATGATGCTC

TTAACTTACT GGTCCTTTTG TCATGGCAAT GTGAGTTTAT ATACTCTGGT GTTTCTGCAG

CTTGTTAAGA GACATGCAGC TGAGATTTTC ACGTCCGTCA TTGTTGCAAC ACTATTTTCA

TTGTATTCAA CGGCTCTCGT GGGACGTCTA GTTGGGTTAG AACCAACGTT GACTGTATCC

ATTATTCCCA GATGTATAAC CGTGGCATTA GCCCTCAGCA TTGTGTCATT CTTTGAAGGT

ATAGTAATGT TCAGAAGCCA GCTGGAAGCA GGGAATTCCA TAAATGGGCA TCCACTAGTG

ATGCTAAAAT TAAATTTTGA CATATCAAAC ACCGTTATTC TGAGATGAAT TCATTTCCAA

TTTACTTAAC GACTTTGGTC AGTTAGAACA CAATGTACTG CAGATGATTG GTGTGACTCA

TTACCATTTT TAATCGAATT AATTTTACAT ATTGGTTGTA GGTGCCAATT CATCTCTCAC

AGCTGCTGTA GTTGTTGTAA CTGGTCTCAT TGGAGCAAAT TTTGTACAAG CAGTGCTCGA

TAAATTAAAT TTTCGTGATC CCATTGCTCG AGGAATAGCA ACTGCTTCCA GGTTTGTGGT

TTACCAAAGA CAAATCAGTA CGAACTCAAG CACTAAACAA TCTTTGCAAG CATAGACCCT

TCCCTTTCTT TAGTAAATAT AATGATGTGT CATATCAGCT ACAAGCAACT ATCTTTCTCA

TAGCTCACCT GTATAGTTTT CTTTCAGGGG ACTGCAACAA AAATGCATCT GGGACCAATA

CTTTGTACTA ACAAAATGCT TGCTGTTGGC CAGAAACTGG AAACTGAATC TCCTGGGGAA

CTTAAAACTG GTTAATAATT AAGCTATTTA ATATGTAGAA AATTCTGAAT GTCACTGAGA

TTCTTATTGC TGAATCTTAT AAAAATCAAA ATCATTTTAG AATTGGACTA GTCAATGAAA

GGAGATCTGT GTTTTCTGT TTTGGTTGAA TATTTTAGTC attttGGtta TAGCATATAA

AAACAAAACC GTGGATTGAA AATAAGAAGA AAGATAGGAT GCTCGAACTT TGCTCACTGA

ATTGGACTTG ATGCACAATC TTGAGTTATG CTTTAAAAAC CTTACCCAAG TTTGTTTGTG

ACTTCGGTTA TAGTCGCAGC TTGTGATGCT CAGATAAGCT CAGTTTACCT GTTCTGTTCA

AGAGTGTACA ACCTGACATG CTCAGTCCTG AGTATTATAT TCATATCCTA CTTTAGTTTT

CCTGTGTGAA GATTTTGCAA AGTTTTGTAG GAACTGTGTC CCATTACTGC ATTTATGCTT

ATCCTTCTTA ATTGTTTCAG TGCTCATGGA CTGGGAACTG CAGCATTGTC AGCCAAGGAA

CCTGAGGCAC TTCCATTTTG TGCCATTGCT TATGCTCTCA CTGGTATATT TGGTTCATTG

TTTTGTTCAG TTCCTGCAGT TAGGCAAAGC TTACTTGCAA TAATTGGCTG AAAGATTGGG

CAGCTTTTGG TTATTGGTGG CCAGACACAC TTTTGATTGA TTATCCTTGT CCACCCACAG

CATGATTTTT AGCAAGTACA CAGTGCTAAT AGCCAACCTT GTATTATTGA TTACAGTCAA

TTATGTATAG AAGTTGACAT CATCCTTCTG CAAAAACTCC TCACCTCCTT TAAATTCCTT

TAAATTATGA ATAGTGAACT GATTGTCTTC TTGTTAGAAG GCGGTCAGCT GGCTGAAAAG

CAAAAGCTAA AGGTCAAAGG TAAATTATCT ATTCTACACC TTGAGAGGGT GGAAAATCCA

GTGGATACCA AGAAGCCAC TGTTGCTCAG

The coding sequence for PtPlgg1 (SEQ ID NO:6) (GenBank Accession No. XM_0245597884 (LOC18096994), which is hereby incorporated by reference in its entirety) is as follows:

ATGGCTACTC CTTTAGTCGC TCATTCCGTT CAGCTCTGTC ATCACCACTC AAAACAATAT

TCTTTCAAAT CACAATCACG TGTCAATAGG GATATCGGTA CAAAAACACT ACTTGGTGTT

TACAATGGAT TCCACAATGT ATATAACCAA TCTTATTTTC ATAAGCCTTG GGCACCCATT

AGAGTTCTTG AGCCTAATTC AAGGTTCTTG CAAATGGGTC CTCAAGAAAC CTGCTCTAGT

CGAGGAATTT CCAAGAAATC TATGAGCTCA GAAGGCAGTA CCAGTACTAG CTCTTCATCT

ATTTCTCAAC AGGTGATTGG GATCTTGCAT TTGCTTGTTT CACTTGGGAT TATCCTTGCA

ATGGATAAGT TGTTGAAAAA GGCATTTGTG GCTGCTGCTA TCAAGTTTCC AAGTGCTCTG

TTTGGCATGT TCTGCATATT CTCAGTTTTA GTCATTCTTG ATATAACTAT TCCGGCTGCT

GCAACAAGCT TAATGAACTT CTTTCAGCCA GCACTGTTAT TCATTCAGAG ATGGCTTCCG

TTGTTCTACG TTCCATCATT GGTTGTTTTG CCTCTCTCTG TTAAAGATAT CCCTGCTGCA

TCAGGTGTCA AGATTTGCTT CATCACAGCT GGAGGGTGGT TGGCGTCACT TTGTGTGGCG

GGTTTTACAG CTATTGCTGT GAGAAAAATG GTGAAGACAG AAATGACTGA TGCTGAGCCT

ATGGCGAAAC CCTCTCCTTT TTCTCCATTG GAAATATGGG CTTGGAGTGG GGTCTTCCTT

GTATCATTTG TTGTCGCATT ATTATATAGA ACGGCATTAG GGACTGCAGC CAGAACATGC

CTTCCTTTCC TACTAGCGTC CACCGTGCTA GGCTATATGG TTGGTTCTGG GTTACCATCT

GGTGTTAAGA AGGTTTTCCA TCCCATTATT TGTTGTGCAC TATCTGCAGA TTTGGCAGCG

TTGGCCTTTG GGTTCCTTTC CCAATCTGGA CTCGATCCCG TTCTAGGATA TTACCTTACA

AAAGTTTCAT CTAATCCTGG AGCTGGTGAT GTGTTAATGG GATTCTTGGG ACCTGTCATT

CTTTCTTTTG CCTTCTCAAT GTTCAAGCAG CGAAAGCTTG TTAAGAGACA TGCAGCTGAG

ATTTTCACGT CCGTCATTGT TGCAACACTA TTTTCATTGT ATTCAACGGC TCTCGTGGGA

CGTCTAGTTG GGTTAGAACC AACGTTGACT GTATCCATTA TTCCCAGATG TATAACCGTG

GCATTAGGCC TCAGCATTGT GTCATTCTTT GAAGGTGCCA ATTCATCTCT CACAGCTGCT

GTAGTTGTTG TAACTGGTCT CATTGGAGCA AATTTTGTAC AAGCAGTGCT CGATAAATTA

AATTTTCGTG ATCCCATTGC TCGAGGAATA GCAACTGCTT CCAGTGCTCA TGGACTGGGA

ACTGCAGCAT TGTCAGCCAA GGAACCTGAG GCACTTCCAT TTTGTGCCAT TGCTTATGCT

CTCACTGGTA TATTTGGTTC ATTGTTTTGT TCAGTTCCTG CAGTTAGGCA AAGCTTACTT

GCAATAATTG GCTGA

The amino acid sequence of PtPlgg1 (SEQ ID NO:7) (GenBank Accession No. XP_024453652, which is hereby incorporated by reference in its entirety) is as follows:

MATPLVAHSV QLCHHHSKQY SFKSQSRVNR DIGTKTLLGV YNGFHNVYNQ SYFHKPWAPI

RVLEPNSRFL QMGPQETCSS RGISKKSMSS EGSTSTSSSS ISQQVIGILH LLVSLGIILA

MDKLLKKAEV AAAIKFPSAL FGMFCIFSVL VILDITIPAA ATSLMNFFQP ALLFIQRWLP

LFYVPSLVVL PLSVKDIPAA SGVKICFITA GGWLASLCVA GFTAIAVRKM VKTEMTDAEP

MAKPSPFSPL EIWAWSGVFL VSFVVALLYR TALGTAARTC LPFLLASTVL GYMVGSGLPS

GVKKVFHPII CCALSADLAA LAFGFLSQSG LDPVLGYYLT KVSSNPGAGD VLMGFLGPVI

LSFAFSMFKQ RKLVKRHAAE IFTSVIVATL FSLYSTALVG RLVGLEPTLT VSIIPRCITV

```
                                    -continued
ALALSIVSFF EGANSSLTAA VVVVTGLIGA NFVQAVLDKL NFRDPIARGI ATASSAHGLG

TAALSAKEPE ALPFCATAYA LTGIFGSLFC SVPAVRQSLL AIIG
```

Additional exemplary Plgg1 sequences are described in Table 9 infra, and are intended to illustrate the various types of plant cells that may be transformed to form a transgenic plant cell of the present disclosure with an inhibitory polynucleotide targeting an endogenous glycolate transporter Plgg1. In some embodiments, the glycolate transporter Plgg1 is a *Populus alba* Plgg1 with a coding region of SEQ ID NO:38. In some embodiments, the glycolate transporter Plgg1 is a *Populus tremula* Plgg1 with a coding region of SEQ ID NO:39. In some embodiments, the glycolate transporter Plgg1 is a *Populus euphratica* Plgg1 with a coding region of SEQ ID NO:40. In some embodiments, the Plgg1 is a *Populus tremula* and a *Populus tremuloides* Plgg1. In some embodiments, the Plgg1 is a *Populus tremula* and a *Populus alba* Plgg1. In some embodiments, the glycolate transporter Plgg1 is from the genus *Picea*. In some embodiments, the glycolate transporter Plgg1 is from the species *Picea abies* with a coding region of SEQ ID NO:41. In some embodiments, the glycolate transporter Plgg1 is from the genus *Pinus*. In some embodiments, the glycolate transporter Plgg1 is from the species *Pinus taeda* with a coding region of SEQ ID NO:35.

The present disclosure also encompasses inhibitory polynucleotides that target endogenous glycolate transporter Plgg1 beyond the specific exemplary glycolate transporter Plgg1 sequences disclosed herein. Glycolate transporter Plgg1 sequences targeted by inhibitory polynucleotides of the transgenic cells of the present disclosure may include glycolate transporter Plgg1 molecules from other organisms that can be readily identified by methods known in the art such as through next generation sequencing and sequence identification based on sequence identity or homology at the nucleotide or the amino acid level. A person of ordinary skill in the art would readily appreciate that glycolate transporter Plgg1 across different genuses and species of plants may have some variation. Transgenic plant cells of the present disclosure may be made with an inhibitory polynucleotide targeting an endogenous glycolate transporter Plgg1 of any plant species.

In some embodiments, inhibitory polynucleotides targeting other endogenous or native chloroplast glycolate transporter Plgg1 coding sequences of other plant varieties and species comprise a glycolate transporter Plgg1 that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity to any one of SEQ ID NO:6, SEQ ID NO:35, or SEQ ID NOs:38-41.

In some embodiments, the inhibitory polynucleotide targeting an endogenous glycolate transporter Plgg1 is an antisense or RNAi molecule comprising a nucleotide sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity of any one of SEQ ID NO:6, SEQ ID NO:35, or SEQ ID NOs:38-41.

In some embodiments, the inhibitory polynucleotide targets a polynucleotide sequence coding for a *Populus trichocarpa* PtPlgg1 having an amino acid sequence of SEQ ID NO:7. In some embodiments, the targeted native chloroplast glycolate transporter Plgg1 has an amino acid sequence that is at least 80% identical to the amino acid sequence of *Populus trichocarpa* PtPlgg1 of SEQ ID NO:7. In some embodiments, the targeted glycolate transporter Plgg1 comprises an amino acid sequence that is at least 80%, 83%, 85%, 90%, 93%, 95%, 98%, 99%, or 100% identical to the amino acid sequence of *Populus trichocarpa* PtPlgg1 of SEQ ID NO:7.

In some embodiments, the inhibitory polynucleotide reduces the expression of the endogenous glycolate transporter Plgg1. As used herein, "reduces expression" refers to the amount or level of RNA or protein expressed in a cell being reduced compared to the amount or level of RNA or protein in a cell that does not have an inhibitory polynucleotide. Expression of RNA may be measured by methods known in the art. For example, RNA expression can be quantified by quantitative and semi-quantitative RT-PCR, RNA sequencing, microarrays, and Northern blots, as non-limiting examples. Protein expression can be quantified by mass spectrometry and western blots, as non-limiting examples.

Expression may be reduced at certain times in the cell or throughout the life of the cell. In some embodiments, expression of the endogenous glycolate transporter Plgg1 is about 10%-90% of the expression of endogenous glycolate transporter Plgg1 in a plant cell that is not transformed with an inhibitory polynucleotide targeting an endogenous glycolate transporter Plgg1, or any amount or range therein. In some embodiments expression of the endogenous glycolate transporter Plgg1 is about 10%, 20%, 30%, 40%, 50%, 60%, 70%, 80%, or 90% of the expression of endogenous glycolate transporter Plgg1 in a plant cell that is not transformed with an inhibitory polynucleotide targeting an endogenous glycolate transporter Plgg1. In some embodiments, expression of endogenous glycolate transporter Plgg1 is about 20% to 80% of the expression of endogenous Plgg1 in a plant cell that is not transformed, or any amount or range therein. In some embodiments, the expression of endogenous glycolate transporter Plgg1 is about 25% to 75% of the expression of endogenous glycolate transporter Plgg1 in a plant cell that is not transformed with an inhibitory polynucleotide targeting an endogenous glycolate transporter Plgg1, or any amount or range therein. In some embodiments, the expression of endogenous glycolate transporter Plgg1 is about 30% to 70% of the expression of endogenous glycolate transporter Plgg1 in a plant cell that is not transformed with an inhibitory polynucleotide targeting an endogenous glycolate transporter Plgg1, or any amount or range therein. In some embodiments, expression of endogenous glycolate transporter Plgg1 is about 30% to 60% of the expression of endogenous glycolate transporter Plgg1 in a plant cell that is not transformed with an inhibitory polynucleotide targeting an endogenous glycolate transporter Plgg1, or any amount or range therein. In some embodiments, expression of endogenous glycolate transporter Plgg1 is about 40% to 60% of the expression of endogenous glycolate transporter Plgg1 in a plant cell that is not transformed with an inhibitory polynucleotide targeting an endogenous glycolate transporter Plgg1, or any amount or range therein.

The expression or activity of an endogenous glycolate transporter Plgg1 can also be reduced by mutating the endogenous glycolate transporter Plgg1. Thus, in some embodiments, the transgenic cell may not have an inhibitory molecule targeting an endogenous glycolate transporter Plgg1, but has a mutation that inhibits normal expression of endogenous glycolate transporter Plgg1. The terms "mutation" or "genome edit" mean a human-induced change in the genetic sequence compared to a wild type sequence (i.e., a sequence that exists in nature). The mutation may be, without limitation, one or more nucleotide insertions, one or more nucleotide substitutions, one or more nucleotide deletions, or any combination thereof. In some embodiments, mutations are those that cause the gene coding sequence or promoter to not be expressed or to have a reduced level of expression, or those that reduce the activity of the encoded protein, such as from a conservative or other amino acid substitution or deletion, a splice junction mutation, or the introduction of a frameshift to the coding region that may lead to a premature stop codon.

In some embodiments, one or more mutations reduce expression of endogenous glycolate transporter Plgg1 by about 20% to 80%, or any amount or range therein, compared to endogenous glycolate transporter Plgg1 in a control. In some embodiments, one or more mutations reduce activity of the glycolate transporter Plgg1 protein by about 20% to 80%, or any amount or range therein compared to an un-mutated glycolate transporter Plgg1. In some embodiments, a mutation may be induced by treatment with a mutagenic agent. Any suitable mutagenic agent can be used for embodiments of the present disclosure. For example, mutagens creating point mutations, deletions, insertions, rearrangements, transversions, transitions, or any combination thereof may be used. Suitable radiation mutagens include, without limitation, ultraviolet light, x-rays, gamma rays, and fast neutrons. Suitable chemical mutagens include, but are not limited to, ethyl methanesulfonate (EMS), methylmethane sulfonate (MMS), N-ethyl-N-nitrosourea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-nitrosoguanidine 25 (MNNG), nitrosoguanidine, 2-aminopurine, 7, 12 dimethyl-benz(a)anthracene (DMBA), ethylene oxide, hexamethylphosphoramide, bisulfan, diepoxyalkanes (diepoxyoctane (DEO), diepoxybutane (DEB), 2-methoxy-6-chloro-9[3-(ethyl-2-chloro-ethyl) aminopropylamino] acridine dihydrochloride (ICR-170), sodium azide, formaldehyde, or combinations thereof.

In some embodiments, a mutation may be induced by genome editing. Genome editing is a type of genetic engineering in which DNA is inserted, replaced, or removed, or any combination thereof, from a genome using artificially engineered nucleases or "molecular scissors." The nucleases typically create double-stranded breaks (DSBs) at desired locations in the genome, and harness the cell's endogenous mechanisms to repair the induced break by processes of homology dependent repair (HDR) or nonhomologous end-joining (NHEJ). Any method of genome editing may be used in the embodiments of the present disclosure.

Transgenic Plant Cell Cultures, Transgenic Plants, and Transgenic Trees

Another aspect of the present disclosure relates to a transgenic plant comprising the transgenic plant cell described herein.

A further aspect of the present disclosure relates to a transgenic plant cell culture produced by methods described herein below.

In the present disclosure, a transgenic plant cell may comprise a polynucleotide of any of the embodiments disclosed herein. A plant cell includes, without limitation, cells from plant tissue, including seeds, suspension cultures, embryos, meristematic regions, cotyledons, hypocotyls, callus tissue, leaves, roots, shoots, gametophytes, sporophytes, pollen, microspores, cotyledons, zygotic and somatic embryos, protoplasts, pollen, embryos, anthers, and the like.

Also provided herein are transgenic plant cell cultures, which comprise plant cells transformed according to the methods disclosed herein, and transgenic plants produced by the methods provided herein.

In one embodiment of the plant cell described above, the plant cell originates from a monocotyledonous or a dicotyledonous plant.

In another embodiment the plant cell originates from a genus selected from the group consisting of *Hordeum, Sorghum, Saccharum, Zea, Setaria, Oryza, Triticum, Secale, Triticale, Malus, Brachypodium, Aegilops, Daucus, Beta, Eucalyptus, Nicotiana, Solanum, Coffea, Vitis, Erythrante, Genlisea, Cucumis, Marus, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium, Spinacia, Helianthus, Populus, Eucalyptus, Pinus, Quercus, Pseudotsuga, Picea, Abies, Tsuga, Sequoia, Thuja, Chamaecyparis*, or *Ficus*.

In some embodiments, the plant cell originates from a species selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus* domestica, *Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia fournieri, Allium cepa, Allium fistulosum, Allium sativum, Allium tuberosum, Helianthus annuus, Helianthus tuberosus*, and/or *Spinacia oleracea*.

In some embodiments, the transgenic plant cell is a transgenic tree plant. Suitable trees include, but are not limited to, plant trees of the genus *Populus, Eucalyptus, Pinus, Quercus, Pseudotsuga, Picea, Abies, Tsuga, Sequoia, Thuja, Chamaecyparis*, or *Ficus*. In some embodiments, the transgenic plant cell is a transgenic tree cell of a genus selected from the group consisting of *Populus, Eucalyptus, Pinus, Quercus, Pseudotsuga, Picea, Abies, Tsuga, Sequoia, Thuja, Chamaecyparis*, and *Ficus*. In some embodiments, the transgenic tree cell is from a tree of the genus *Populus*. In some embodiments, the transgenic tree cell is from a hybrid tree of *Populus tremula* x *Populus alba*.

Transgenic plants may be produced by methods described herein. In some embodiments, a transgenic plant comprises the transgenic plant cell. In some embodiments, the transgenic plant is a transgenic tree plant. Suitable trees include, but are not limited to, *Populus, Eucalyptus, Pinus, Quercus, Pseudotsuga, Picea*, and *Ficus* trees. In some embodiments, the transgenic tree is of the genus *Populus, Eucalyptus, Pinus, Quercus, Pseudotsuga, Picea*, or *Ficus*. In some embodiments, the transgenic tree is of the genus *Populus*. In some embodiments, the transgenic tree is a hybrid of *Populus tremula* x *Populus alba*.

The methods and compositions of the present disclosure can be used over a broad range of plant species. Such plants, include, but are not limited to *Populus* species (*P. alba, P. alba* x *P. grandidentata, P. alba* x *P. tremula, P. alba* x *P. tremula* var. *glandulosa, P. alba* x *P. tremuloides, P. balsamifera, P. balsamifera* subsp. *trichocarpa, P. balsamifera* subsp. *trichocarpa* x *P. deltoides, P. ciliata, P. deltoides, P. euphratica, P. euramericana, P. kitakamiensis, P. lasiocarpa, P. laurifolia, P. maximowiczii, P. maximowiczii* x *P. balsamifera* subsp. *trichocarpa, P. nigra, P. sieboldii* x *P. grandidentata, P. suaveolens; P. szechuanica, P. tomentosa, P. tremula, P. tremula* x *P. tremuloides, P. tremuloides, P. wilsonii, P. canadensis*, and *P. yunnanensis*).

Such plants, also include, but are not limited to, *Eucalyptus* species (*E. alba, E. albens, E. amygdalina, E. aromaphloia, E. baileyana, E. balladoniensis, E. bicostata, E. botryoides, E. brachyandra, E. brassiana, E. brevistylis, E. brockwayi, E. camaldulensis, E. ceracea, E. cloeziana, E. coccifera, E. cordata, E. cornuta, E. corticosa, E. crebra, E. croajingolensis, E. curtisii, E. dalrympleana, E. deglupta, E. delegatensis, E. delicata, E. diversicolor, E. diversifolia, E. dives, E. dolichocarpa, E. dundasii, E. dunnii, E. data, E. erythrocorys, E. erythrophloia, E. eudesmoides, E. falcata, E. gamophylla, E. glaucina, E. globulus, E. globulus* subsp. *bicostata, E. globulus* subsp. *globulus, E. gongylocarpa, E. grandis, E. grandis* x *urophylla, E. guilfoylei, E. gunnii, E. hallii, E. houseana, E. jacksonii, E. lansdowneana, E. latisinensis, E. leucophloia, E. leucoxylon, E. lockyeri, E. lucasii, E. maidenii, E. marginata, E. megacarpa, E. melliodora, E. michaeliana, E. microcorys, E. microtheca, E. muelleriana, E. nitens, E. nitida, E. obliqua, E. obtusiflora, E. occidentalis, E. optima, E. ovata, E. pachyphylla, E. pauciflora, E. pellita, E. perriniana, E. petiolaris, E. pilularis, E. piperita, E. platyphylla, E. polyanthemos, E. populnea, E. preissiana, E. pseudoglobulus, E. pulchella, E. radiata, E. radiata* subsp. *radiata, E. regnans, E. risdonii, E. robertsonii, E. rodwayi, E. rubida, E. rubiginosa, E. saligna, E. salmonophloia, E. scoparia, E. sieberi, E. spathulata, E. staeri, E. stoatei, E. tenuipes, E. tenuiramis, E. tereticornis, E. tetragona, E. tetrodonta, E. tindaliae, E. torquata, E. umbra, E. urophylla, E. vernicosa, E. viminalis, E. wandoo, E. wetarensis, E. willisii, E. willisii* subsp. *falciformis, E. willisii* subsp. *willisii, and E. woodwardii*).

Such plants, also include, but are not limited to, conifers. Exemplary conifers include, without limitation, trees of the genus *Pinus*, including, for example, loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The transgenic plants (and trees) obtained by the methods disclosed herein show enhanced biomass productivity and have increased carbon content compared to a non-transgenic plant or a non-transgenic tree of the same species. Transformation of plants and forest trees by the disclosed methods increases biomass productivity by 10-40% or more.

Increased biomass can be measured, for example, as an increase in plant height, plant total leaf area, plant fresh weight, plant dry weight, plant volume, plant stem, plant root, plant seed, lumber yield, or any combination thereof, as compared with control plants. In some embodiments, the transgenic plant has increased biomass accumulation compared to a plant of the same species not comprising the transgenic plant cell. In some embodiments, the transgenic plant has at least 5% to 100%, or any amount or range therein, or greater than 100% more biomass accumulation compared to a plant of the same species not comprising the transgenic plant cell. In some embodiments, the transgenic plant has at least 10% more biomass accumulation compared to a non-transgenic plant of the same species. In some embodiments, the transgenic plant has at least 20% more biomass accumulation compared to a non-transgenic plant of the same species. In some embodiments, the transgenic plant has at least 30% more biomass accumulation compared to a non-transgenic plant of the same species. In some embodiments, the transgenic plant has at least 40% more biomass accumulation compared to a non-transgenic plant of the same species. In some embodiments, the transgenic plant has more stem biomass compared to the stem biomass of a plant of the same species not comprising the transgenic plant cell. In some embodiments, the transgenic plant has at least 5% to 100%, or any amount or range therein, or greater than 100% more stem biomass accumulation compared to the stem biomass of a plant of the same species not comprising the transgenic plant cell. In some embodiments, the transgenic plant has more leaf biomass compared to the leaf biomass of a plant of the same species not comprising the transgenic plant cell. In some embodiments, the transgenic plant has at least 5% to 100%, or any amount or range therein, or greater than 100% more leaf biomass accumulation compared to the leaf biomass of a plant of the same species not comprising the transgenic plant cell. In some embodiments, the transgenic plant has more root biomass compared to the root biomass of a plant of the same species not comprising the transgenic plant cell. In some embodiments, the transgenic plant has at least 5% to 100%, or any amount or range therein, or greater than 100% more root biomass accumulation compared to the root biomass of a plant of the same species not comprising the transgenic plant cell.

Biomass may be measured at various time points, including, for example and without limitation, 3 months to several years after seed germination or planting, or any amount of time therein.

In some embodiments, the transgenic plant has more height compared to the height of a plant of the same species not comprising the transgenic plant cell. In some embodiments, the transgenic plant has at least 5% to 100%, or any amount or range therein, or greater than 100% more height compared to the height of a plant of the same species not comprising the transgenic plant cell. In some embodiments, the transgenic plant has more stem volume compared to the stem volume of a plant of the same species not comprising the transgenic plant cell. In some embodiments, the transgenic plant has at least 5% to 100%, or any amount or range therein, or greater than 100% more stem volume compared to the stem volume of a plant of the same species not comprising the transgenic plant cell.

Polynucleotide Constructs

A further aspect of the present disclosure relates to a polynucleotide construct comprising an inhibitory polynucleotide comprising a polynucleotide sequence that targets an endogenous glycolate transporter Plgg1 present in a plant cell, wherein when expressed in the plant cell, the inhibitory polynucleotide reduces expression of the endogenous glycolate transporter Plgg1 by about 20% to 80% of expression of endogenous glycolate transporter Plgg1 in a plant cell where the inhibitory polynucleotide is not present.

This aspect of the present application can be carried out with any of the embodiments disclosed herein.

The polynucleotide sequences of the present disclosure may be present on one or more constructs such as a plasmid for use in transformation, or on linear fragments of DNA. In some embodiments, the polynucleotide construct comprises one or more of the polynucleotide sequences disclosed herein. In some embodiments, the polynucleotide construct comprises a first polynucleotide sequence encoding a glycolate dehydrogenase, and a first promoter operably linked to the first polynucleotide sequence. In some embodiments, the polynucleotide construct comprises a second polynucleotide sequence encoding a malate synthase, and a second promoter operably linked to the second polynucleotide sequence.

In some embodiments, the polynucleotide sequence that targets an endogenous glycolate transporter Plgg1 present in a plant cell comprises 20-1000 nucleotides of any one of SEQ ID NO:6, SEQ ID NO:35, or SEQ ID NOs:38-41 In some embodiments, the polynucleotide sequence that targets an endogenous glycolate transporter Plgg1 present in a plant cell comprises 20-1000 nucleotides comprising a nucleotide sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity of any one of SEQ ID NO:6, SEQ ID NO:35, or SEQ ID NOs:38-711.

In some embodiments, the inhibitory polynucleotide comprises SEQ ID NO:8 and SEQ ID NO:9. In some embodiments, the inhibitory polynucleotide comprises SEQ ID NO:36 and SEQ ID NO:37.

In some embodiments, the glycolate dehydrogenase comprises a nucleotide sequence of any one of SEQ ID NO:1, 46, or 48. In some embodiments, the glycolate dehydrogenase comprises a nucleotide sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity of any one of SEQ ID NO:1, 46, or 48. In some embodiments, the malate synthase comprises a nucleotide sequence of any one of SEQ ID NO: 3, or 42-45. In some embodiments, the malate synthase comprises a nucleotide sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity of any one of SEQ ID NO:3, or 42-45.

In some embodiments, the polynucleotide construct includes left and right *Agrobacterium* T-DNA border sequences (Peralta and Ream, "T-DNA Border Sequences Required for Crown Gall Tumorigenesis," *Proc. Natl. Acad. Sci.* 82:5112-5116 (1985), which is hereby incorporated by reference in its entirety). These border sequences allow the introduction of heterologous DNA located between the left and right T-DNA border sequences into a host cell when using *Agrobacterium*-mediated DNA transformation.

Standard cloning procedures known in the art can be used to prepare the polynucleotide construct and/or the vector, such as described by Sambrook et al., Molecular Cloning: A Laboratory Manual, Third Edition, Cold Spring Harbor: Cold Spring Harbor Laboratory Press, New York (2001), which is hereby incorporated by reference in its entirety.

Methods of Increasing Biomass Productivity in Plants

Another aspect of the present disclosure relates to a method for increasing biomass productivity in a plant. This method involves transforming plant cells with one or more polynucleotides comprising a first promoter operably linked to a polynucleotide sequence encoding a glycolate dehydrogenase, a second promoter operably linked to a polynucleotide sequence encoding a malate synthase, and an inhibitory polynucleotide targeting an endogenous glycolate transporter Plgg1, where expression of the endogenous glycolate transporter Plgg1 in the transformed plant cell is about 20% to 80% of expression of endogenous glycolate transporter Plgg1 in a plant cell that is not transformed with an inhibitory polynucleotide targeting an endogenous glycolate transporter Plgg1, wherein said transforming increases biomass productivity of the plant.

This aspect of the present disclosure can be carried out with any of the embodiments disclosed herein.

Also provided herein are transgenic plant cell cultures, which comprise plant cells transformed according to the methods disclosed herein, and transgenic plants produced by the methods provided herein. In some embodiments, the methods comprise a transgenic plant cell culture. Some embodiments may further comprise culturing the transgenic plant cells under conditions effective to obtain transgenic plants.

In some embodiments, the polynucleotide construct comprising the polynucleotide sequences of the present disclosure is introduced into a host cell. "Introduced" includes the incorporation of a nucleotide into a eukaryotic or prokaryotic cell, where the nucleotide may be incorporated into the genome of the cell, and includes reference to the transient provision of a nucleotide or protein to the cell. The term also may include a reference to stable or transient transformation methods, as well as sexually crossing. Thus, "introduced" in the context of inserting a polynucleotide fragment (e.g., a polynucleotide construct/expression construct) into a cell, means transfection, transformation, or transduction and includes the incorporation of a nucleotide fragment into a eukaryotic or prokaryotic cell where the nucleotide fragment is incorporated into the genome of the cell (e.g., chromosome, plasmid, plastid, or mitochondrial DNA), converted into an autonomous replicon, or transiently expressed.

Polynucleotide constructs and vectors can be introduced into cells via transformation. Transformation refers to both stable transformation and transient transformation. A transient transformation refers to the introduction of the polynucleotide construct into the plant cell of a host organism resulting in gene expression without genetically stable inheritance.

A stable transformation refers to the introduction of the polynucleotide construct into a genome of a host organism resulting in genetically stable inheritance. Once stably transformed, the nucleotide fragment is stably integrated in the genome of the host organism and any subsequent generation.

Selectable markers may be used to select for plants or plant cells that comprise a polynucleotide construct. Selection of transformed cells comprising the polynucleotide construct utilizes an antibiotic or other compound useful for selective growth as a supplement to the media. The compound to be used will be dictated by the selectable marker element present in the vector with which the host cell was transformed. The marker may encode biocide resistance, antibiotic resistance (e.g., kanamycin, Geneticin (G418), bleomycin, hygromycin, etc.), or herbicide resistance (e.g., glyphosate, glufosinate, etc.). Examples of selectable markers include, but are not limited to, a neo gene which codes for kanamycin resistance and can be selected for using kanamycin, G418, etc.; a bar gene which codes for bialaphos resistance; a mutant EPSP synthase gene which encodes glyphosate resistance; a nitrilase gene, which confers resistance to bromoxynil; a mutant acetolactate synthase gene (ALS), which confers imidazolinone or sulfonylurea resistance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, etc. Examples of selectable markers are described in, e.g., U.S. Pat. Nos. 5,550,318; 5,633,435; 5,780,708; and 6,118,047, which are hereby incorporated by reference in their entirety.

The methods disclosed herein comprise introducing the polynucleotide sequences into plant cells by transformation. In some embodiments the polynucleotides are introduced into the plant cells by methods such as *Agrobacterium tumefaciens* infection, electroporation, particle bombardment, or protoplast transfection to obtain transgenic plant cells.

A variation of *Agrobacterium* transformation uses vacuum infiltration in which whole plants are used (Senior, "Uses of Plant Gene Silencing," *Biotechnology and Genetic Engineering Reviews* 15:79-119 (1998), which is hereby incorporated by reference in its entirety). In some embodiments, transformation involves fusion of protoplasts with other entities, either minicells, cells, lysosomes, or other fusible lipid-surfaced bodies (Fraley et al., "Liposome-Mediated Delivery of Tobacco Mosaic Virus RNA into Tobacco Protoplasts: A Sensitive Assay for Monitoring Liposome-Protoplast Interactions," *Proc. Natl. Acad. Sci. USA* 79:1859-63 (1982), which is hereby incorporated by reference in its entirety).

In some embodiments, transformation can be accomplished by electroporation (Fromm et al., "Expression of Genes Transferred into Monocot and Dicot Plant Cells by Electroporation," *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

In some embodiments, transformation can be accomplished through PEG-mediated DNA transfer, microinjection, or vacuum infiltration to provide for stable or transient expression of the polynucleotide construct. Other methods of transformation include polyethylene-mediated plant transformation, micro-injection, physical abrasives, and laser beams (Senior, "Uses of Plant Gene Silencing," *Biotechnology and Genetic Engineering Reviews* 15:79-119 (1998), which is hereby incorporated by reference in its entirety). In any of these methods, transformation can be enhanced by the use of a suitable microbe, such as a *Rhizobia* microbe, or an *Agrobacterium*, to facilitate DNA uptake by plant cells.

In some embodiments, transient or stable transformation of polynucleotide constructs described herein is performed using particle bombardment (also known as biolistic transformation). In some embodiments, particle bombardment involves propelling inert or biologically active particles at cells. This technique is disclosed, for example, in Klein et al., "High-Velocity Microprojectiles for Delivering Nucleic Acids Into Living Cells," *Nature* 327:70-73 (1987), which is hereby incorporated by reference in its entirety, and is also known as biolistic transformation of the host cell, as disclosed in U.S. Pat. Nos. 4,945,050; 5,036,006; and 5,100,792, all to Sanford et al., and in Emerschad et al., "Somatic Embryogenesis and Plant Development from Immature Zygotic Embryos of Seedless Grapes (*Vitis vinifera*)," Plant Cell Reports 14:6-12 (1995), which are hereby incorporated by reference in their entirety. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. In some embodiments, the target cell can be surrounded by the vector so that the vector is carried into the cell by the wake of the particle. Biologically active particles (e.g., dried bacterial cells containing the vector and heterologous DNA) can also be propelled into cells.

In some embodiments, biolistic methods use gold or tungsten particles typically of 0.5 to 2 micrometers in size and coated with DNA, RNA, or ribonucleotide particles that has been precipitated onto the particles; the particles are discharged using a "gene gun" powered by a gas at high pressure (typically hundreds to thousands pounds per square inch) onto a plant held in an evacuated chamber. Some biolistic methods using equipment such as the Helios® gene gun (Bio-Rad Laboratories, Inc.) use lower pressures (in the hundreds pounds per square inch). Biologically active particles (e.g., dried bacterial cells containing the vector and heterologous DNA) can also be propelled into plant cells. Other variations of particle bombardment, now known or hereafter developed, can also be used.

Methods for transforming trees are known in the art, such as described in U.S. Pat. No. 6,518,485, which is hereby incorporated by reference in its entirety, which discloses biolistic transformation method of gymnosperm somatic embryos, and Li et al., "Simple, Rapid and Efficient Transformation of Genotype Nisqually-1: A Basic Tool for the First Sequenced Model Tree," *Scientific Reports* 7:2638 (2017), which is hereby incorporated by reference in its entirety. Any method of transformation that results in efficient transformation of the host cell of choice is appropriate for practicing the methods of the present disclosure.

In some embodiments, the disclosed methods may further comprise culturing the transgenic plant cells under conditions, which stimulate plant growth to obtain transgenic plants. In some embodiments, the transgenic plants show enhanced biomass productivity and/or have increased carbon content compared to non-transgenic plants of the same species.

After transformation, transformed plant cells can be regenerated. Means for regeneration vary from species to species of plant, but generally a petri plate containing explants or a suspension of transformed protoplasts is first provided. Callus tissue is formed and transformation of callus tissue can be performed. Shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, genotype, and history of the culture.

Transformed cells may first be identified using a selection marker simultaneously introduced into the host cells along with the polynucleotide construct or vector as described herein. Suitable selection markers are described above. Cells or tissues are grown on a selection medium containing the appropriate antibiotic, whereby generally only those transformants expressing the antibiotic resistance marker continue to grow. Other types of markers are also suitable for inclusion in the vector, such as reporter genes as described above. The selection employed will depend on the target species; for certain target species, different antibiotics, herbicide, or biosynthesis selection markers may be preferred.

Plant cells and tissues selected by means of an inhibitory agent or other selection marker are then tested for the acquisition of the polynucleotide construct. In some embodiments, a transgenic cell comprises the heterologous polynucleotides. In some embodiments, the transgenic cell is a transgenic plant cell. As used herein, a transgenic cell or plant cell comprises within its genome a heterologous nucleotide introduced by a transformation step. The heterologous nucleotide is stably integrated within the genome such that the nucleotide is passed on to successive generations. As used herein, "genome", as it applies to plant cells, encompasses not only chromosomal DNA found within the nucleus, but organelle DNA found within subcellular components (e.g., mitochondrial, plastid) of the cell. The heterologous nucleotide may be integrated into the genome alone or as part of a polynucleotide construct. In some embodiments, a transgenic plant is regenerated from the transgenic cell. In some embodiments, a transgenic plant comprises the transgenic plant cell.

Methods of Increasing Photosynthetic Activity and Stomatal Conductance in Plants A further aspect of the present disclosure is directed to a method for increasing photosynthetic activity and stomatal conductance under drought conditions in a plant. This method involves transforming plant cells with one or more polynucleotides comprising a first promoter operably linked to a polynucleotide sequence encoding a glycolate dehydrogenase, a second promoter operably linked to a polynucleotide sequence encoding a malate synthase, and an inhibitory polynucleotide targeting an endogenous glycolate transporter Plgg1, wherein expression of the endogenous glycolate transporter Plgg1 in the transgenic plant cell is about 20% to 80% of expression of endogenous glycolate transporter Plgg1 in a plant cell that is not transformed with an inhibitory polynucleotide targeting an endogenous glycolate transporter Plgg1. The method further involves regenerating a plant from the transformed plant cell, and subjecting the plant to drought conditions. Said transforming increases photosynthetic activity and stomatal conductance under drought conditions in the regenerated plant.

This aspect of the present disclosure can be carried out with any of the embodiments disclosed herein.

As used herein, "drought" refers to a decrease in water availability to a plant that, especially when prolonged, can cause damage to the plant or prevent its successful growth (e.g., limiting plant growth or seed yield). Drought tolerance is a trait of a plant to survive under drought conditions over prolonged periods of time without exhibiting substantial physiological or physical deterioration. In some embodiments, drought can be estimated by soil moisture levels. In some embodiments, a soil moisture level >9.5 indicates no drought, a soil moisture level of 7.5-9.49 indicates mild drought, a soil moisture level of 5.5-7.49 indicates moderate or medium drought, and a soil moisture level <5.49 indicates severe drought.

Photosynthetic activity can be estimated, for example, by measuring maximum rate of photosynthetic electron transport ($J_{max}$) and/or maximum carbon assimilation rate ($A_{max}$). Photosynthetic activity can decrease during drought conditions, especially severe drought conditions.

Stomatal conductance estimates the rate of gas exchange and transpiration or water loss through the leaf stomata, and is a measure of the degree of stomatal opening. Stomatal conductance reflects the physical resistance of the movement of gases between air and the interior of the leaf, and thus indirectly reflects the state of photosynthetic activity. Stomatal conductance can be a sensitive indicator of stress. During drought conditions, stoma in leaves may close to reduce water loss, which will lead to a drastic decrease in stomatal conductance Water use efficiency (WUE) is a metric that describes the potential water cost of carbon assimilation. WUE is measured as the ratio of net carbon assimilation to stomatal conductance to water vapor. Basically it reflects the ratio of water used for photosynthetic activity to water lost through transpiration. Under normal growth conditions where water supply is sufficient, higher WUE generally translates to higher photosynthetic activity. In drought conditions, stomata close to prevent water loss through transpiration resulting in WUE increases. The more severe the drought the higher the WUE. Some plants that cope well under the drought condition maintain some degree of stomatal conductance and photosynthetic activity. The rate of increase in WUE in those plants under drought conditions is smaller compared to that of plants that do not tolerate drought.

In some embodiments, the transgenic plant has increased stomatal conductance compared to a plant of the same species not comprising the transgenic plant cell during moderate or severe drought. In some embodiments the transgenic plant has at least 5% to 50%, or any amount or range therein, or more than 50% more stomatal conductance compared to a plant of the same species not comprising the transgenic plant cell during moderate or severe drought. In some embodiments, the transgenic plant has increased photosynthetic activity compared to a plant of the same species not comprising the transgenic plant cell during moderate or severe drought. In some embodiments the transgenic plant has at least 5% to 50%, or any amount or range therein, or more than 50% more photosynthetic activity compared to a plant of the same species not comprising the transgenic plant cell during moderate or severe drought.

The following examples are intended to exemplify the embodiments of the disclosure but are by no means intended to limit the scope thereof.

EXAMPLES

Example 1—RNAi Construct for *Populus* Plgg1

The genomic *Populus trichocarpa* PtPlgg1 sequence, is a 6.3 kb gene with 5 exons, large introns, a 136 bp 5'UTR and a 334 bp 3'UTR (SEQ ID NO:5). Immediately upstream of PtPlgg1 (185 bp) is the 3'UTR of neighboring Potri.003G099700 (FIG. 1).

Figure 2:
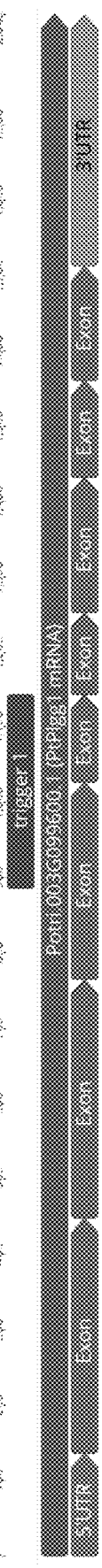
FIG. 2 is a schematic illustration of "trigger site one" represented on a post-transcriptional RNA model of the PtPlgg1 nucleotide sequence.

The RNAi region selected for intron-containing hairpin RNAi (ihRNAi) of PtPlgg1 was a 256 nt region from 750-1,006 nucleotides of the coding sequence. These numbers correspond to nucleotides 886-1,142 of the transcript sequence (FIG. 2) and 750-1006 nucleotides measured from the start codon. The sequence used for the *Populus* PtPlgg1 RNAi construct in the sense direction (FIG. 3) is SEQ ID NO:8, as follows:

```
GGAAATATGG GCTTGGAGTG GGGTCTTCCT TGTATCATTT GTTGTCGCAT TATTATATAG

AACGGCATTA GGGACTGCAG CCAGAACATG CCTTCCTTTC CTACTAGCGT CCACCGTGCT

AGGCTATATG GTTGGTTCTG GGTTACCATC TGGTGTTAAG AAGGTTTTCC ATCCCATTAT

TTGTTGTGCA CTATCTGCAG ATTTGGCAGC GTTGGCCTTT GGGTTCCTTT CCCAATCTGG

ACTCGATCCC GTTCTAG
```

The sequence used for the *Populus* PtPlgg1 RNAi construct in the antisense direction (FIG. 3) is SEQ ID NO:9, as follows:

```
CTAGAACGGG ATCGAGTCCA GATTGGGAAA GGAACCCAAA GGCCAACGCT GCCAAATCTG

CAGATAGTGC ACAACAAATA ATGGGATGGA AAACCTTCTT AACACCAGAT GGTAACCCAG

AACCAACCAT ATAGCCTAGC ACGGTGGACG CTAGTAGGAA AGGAAGGCAT GTTCTGGCTG

CAGTCCCTAA TGCCGTTCTA TATAATAATG CGACAACAAA TGATACAAGG AAGACCCCAC

TCCAAGCCCA TATTTCC
```

This sequence was selected by blasting various regions of the *Populus alba* PaPlgg1 transcript to the *Populus trichocarpa* genome and selecting regions with a low number of "hits" elsewhere in the genome in an attempt to minimize off-target siRNAs. No attempt was made to estimate and select based on siRNA efficiency, or to map the off-target potentials of individual 21-mer siRNA sequences. The coding sequence of *Populus alba* Plgg1 (SEQ ID NO:38), one of the targets of RNAi, was greater than 98% identical at the nucleotide level to the coding sequence of *Populus trichocarpa* PtPlgg1 (Potri.003G099600) (SEQ ID NO:6). Similarly, the coding sequence of *Populus tremula* Plgg1 (Potra000595g04516) (SEQ ID NO:39) was greater than 98% identical at the nucleotide level to the coding sequence of PtPlgg1 (SEQ ID NO:6). An alignment between Plgg1 coding sequences and the area selected for the RNAi sense polynucleotide (SEQ ID NO:8) is shown in FIG. 4. Included in the alignment are Plgg1 sequences from both parents of the Poplar variety INRA 717-1B4, which is a hybrid between *Populus tremula* and *Populus alba*, and the *Populus trichocarpa* PtPlgg1. As shown below in Examples 3-11, the RNAi construct was effective at reducing expression of endogenous Plgg1 genes in a hybrid *Populus tremula* x *Populus alba* tree species and would be expected to be effective in other *Populus* species and hybrid species as well.

Figure 5:
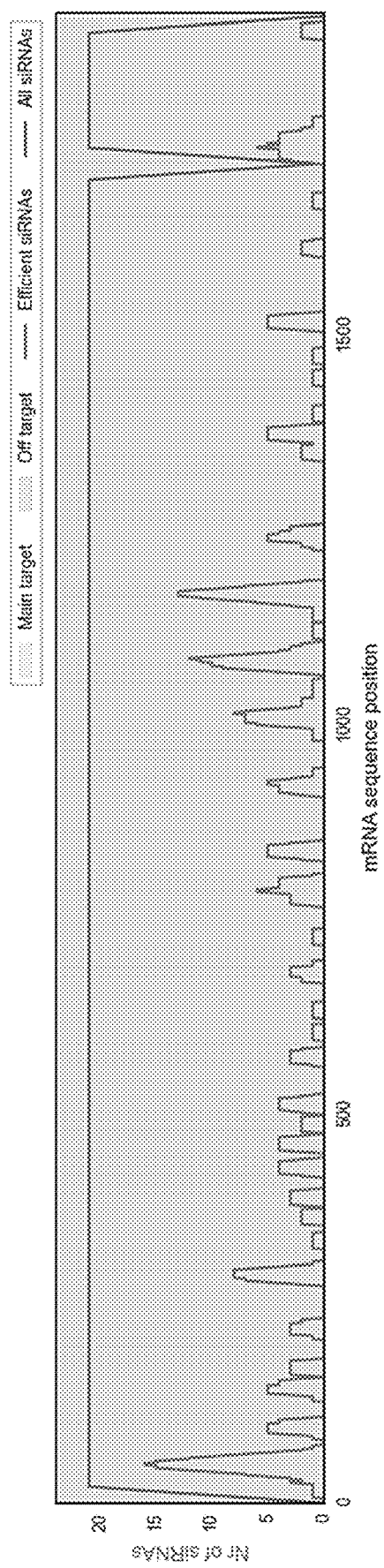
FIG. 5 is a graph showing the siRNA Finder ("siFi") output for RNAi design.
Figure 6:
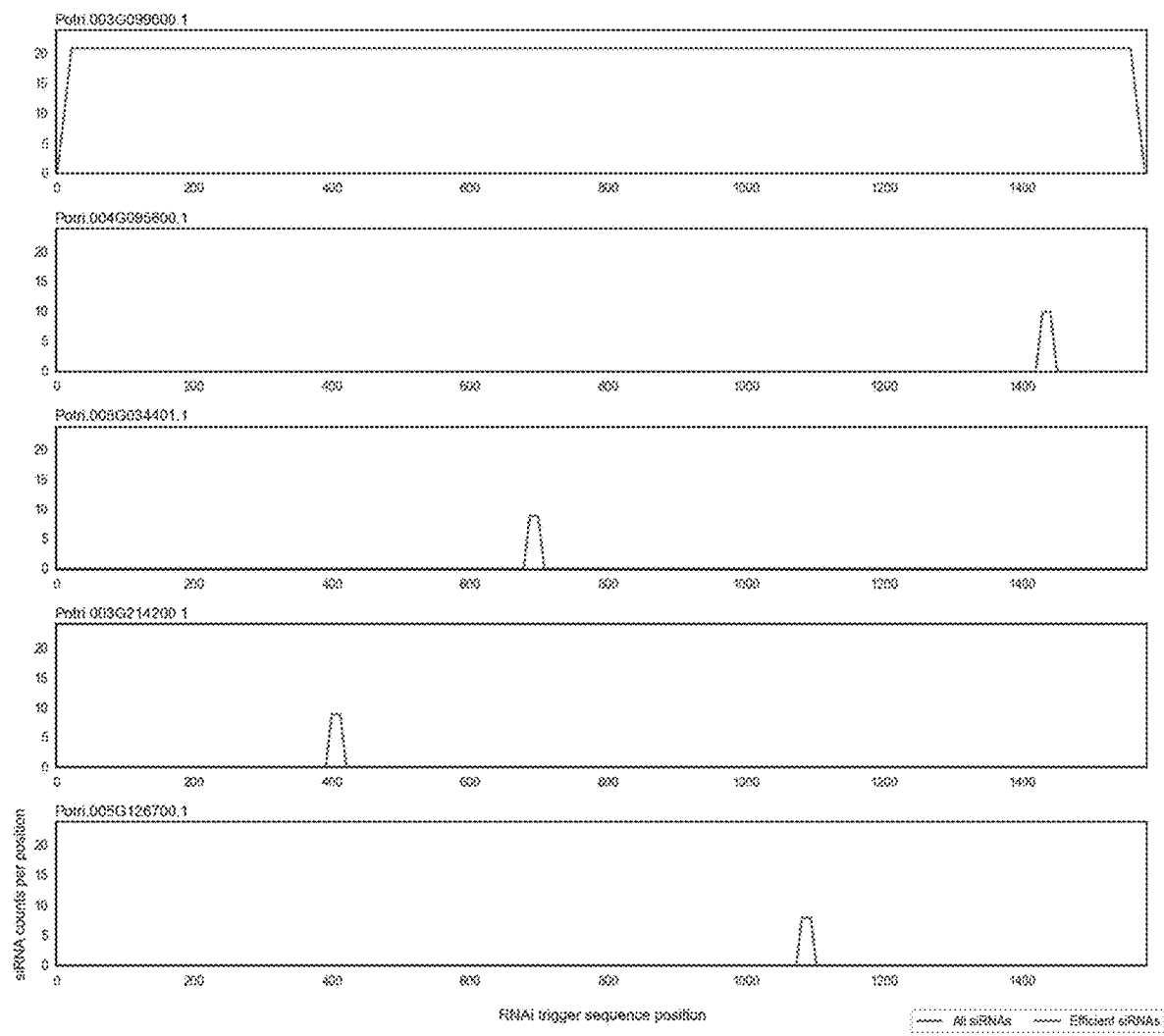
FIG. 6 shows the siFi output for off-target prediction in PtPlgg1, which allows three mismatches in 21mer siRNAs.

SiFi is a software disclosure for RNAi design and off-target prediction, which allows users to upload their own transcript database for off-target prediction (Luck et al., "siRNA-Finder (si-Fi) Software for RNAi-Target Design and Off-Target Prediction," *Front. Plant Sci.* 10:1023 (2019), which is hereby incorporated by reference in its entirety). SiFi can be run in RNAi Design mode or Off-Target Prediction mode. There are also options to change siRNA size, alter the 5' terminal nucleotide rule, strand selection, end stability difference with option to change difference, target site accessibility threshold with option to change threshold, and accessibility calculation window. The default settings used for this analysis are 21mers with (1 mismatch tolerated for design, and 3 for off-target prediction), 5' terminal nucleotide rule on, strand selection on, end stability difference set to 1.00, target site accessibility threshold set to 0.10, and accessibility calculation window set to 8. RNAi design output on the PtPlgg1 mRNA sequence (FIG. 5) shows zones of highly efficient siRNAs, including a zone from 1000-1200 bp, a dense region around 500 bp, and confirmation that the beginning of the sequence has an adequate number of active siRNAs. Off-target prediction (presented in FIG. 6) shows regions to avoid right at approximately 1430 bp, 700 bp, 400 bp, and 1100 bp measured from the start codon.

In light of the data generated by siFi, two other promising trigger regions include the first 250 bp of SEQ ID NO:6, which presents as a cluster of efficient siRNAs with low off-target potential, and the region 400-650 bp of SEQ ID NO:6, which includes many potential siRNAs and low off-target potential. RNAi constructs using these sequences can be made in a similar fashion to the construct shown in FIG. 3, with a sense and antisense fragment of the chosen Plgg1 sequence. An intronic or other sequence may be used to separate the sense and antisense sequences. The sequence used in the PtPlgg1 construct with SEQ ID NO:8 and SEQ ID NO:9 was an intron of the *Flaveria trinervia* Pyruvate Orthophosphate Dikinase ("PDK") (GenBank Accession No. X79095.1, which is hereby incorporated by reference in its entirety).

Figure 3:
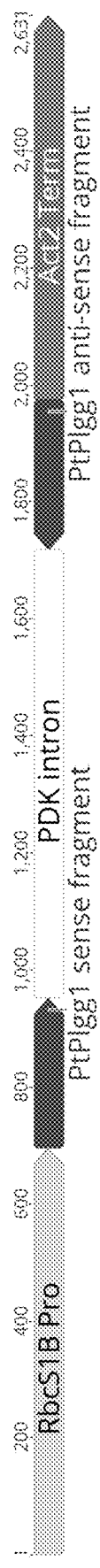
FIG. 3 is a schematic illustration of one embodiment of a PtPlgg1 RNAi cassette. The PtPlgg1 sense fragment and the PtPlgg1 anti sense fragment are separated by the PDK intron.
Figure 7:
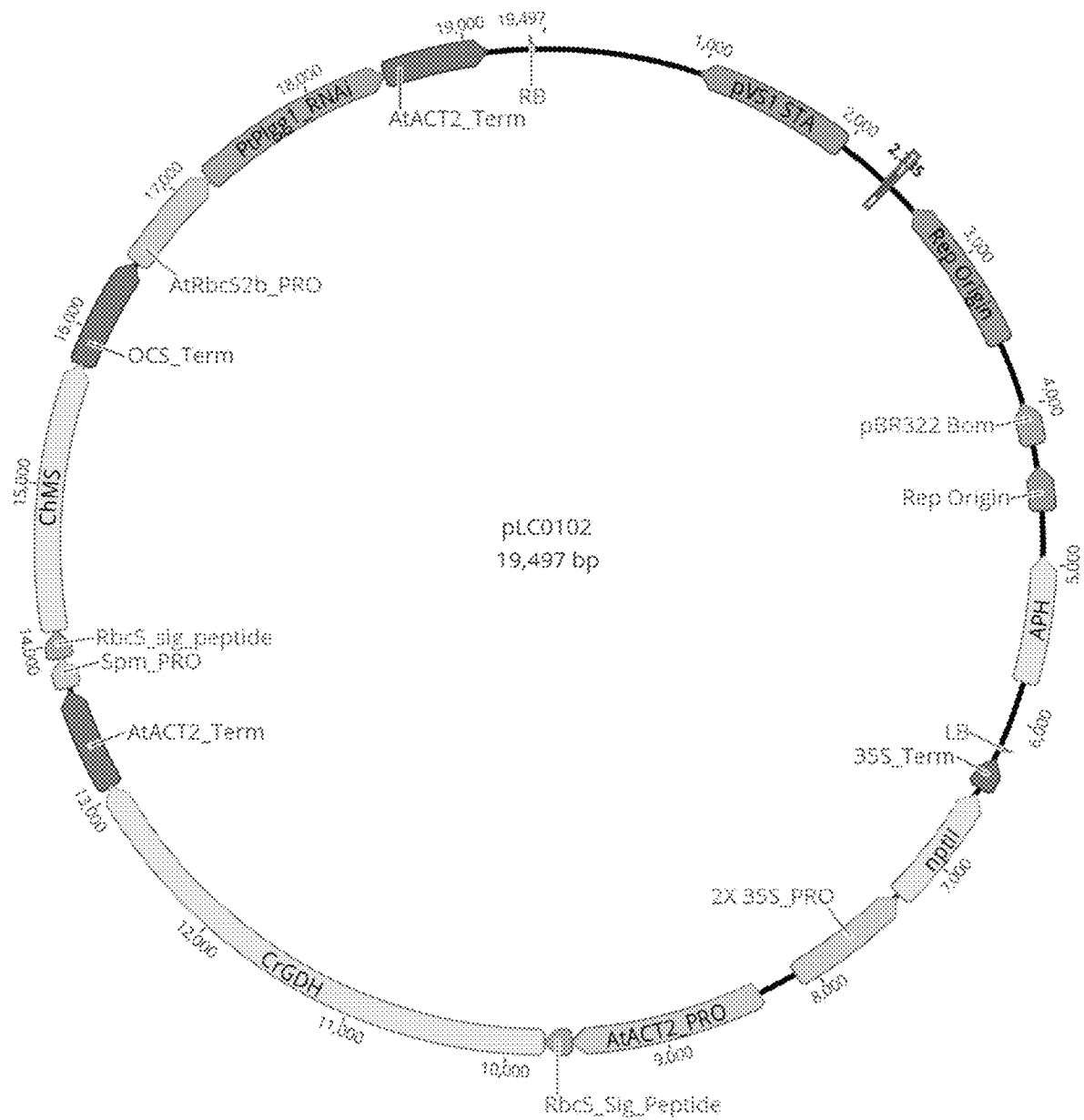
FIG. 7 is a schematic illustration showing one embodiment of a vector described herein, pLC0102, with polynucleotide constructs comprising the glycolate dehydrogenase gene from *Chlamydomonas reinhardtii* ("GDH") operably linked to the Act2 promoter and the RbcS signal peptide, the malate synthase gene ("MS") from *Cucurbita hybrida* (sp. *Kurokawa Amakuri Nankin*) operably linked to the Spm promoter and the RbcS signal peptide, and an RNAi for the glycolate transporter Plgg1 from *Populus trichocarpa*. Expression of the RNAi cassette is driven by the AtRbcs2b promoter.
Figure 8:
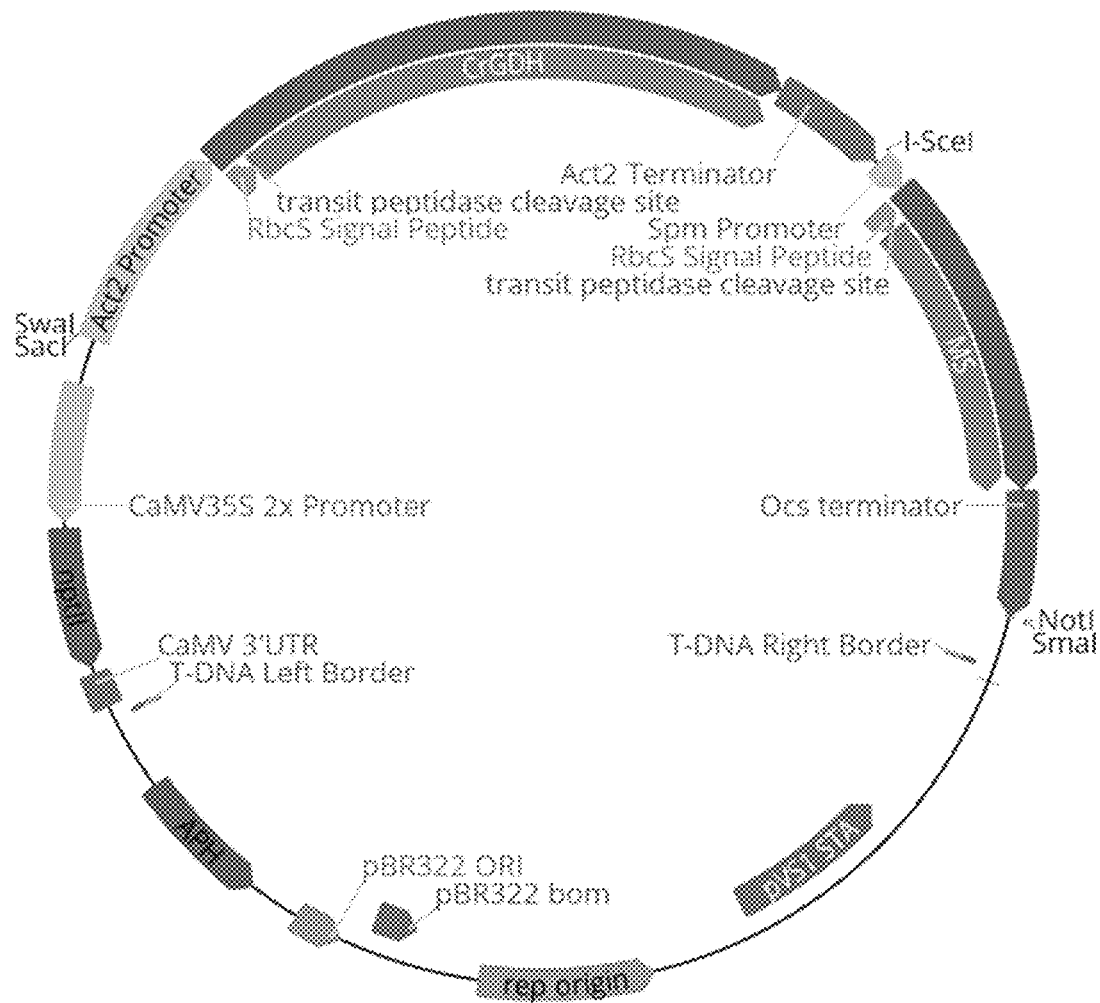
FIG. 8 is a schematic illustration showing one embodiment of a vector described herein, with the RbcS signal peptide and transit peptidase cleavage sites added at the N-terminus of CrGDH and MS to target chloroplasts.

Example 2—Tree Culture, Growth Conditions, Construction of Vectors and Genetic Transformation Construct pLC0102 comprising a gene encoding glycolate dehydrogenase from *Chlamydomonas reinhardtii* (SEQ ID NO:2) operably linked to the Arabidopsis *thaliana* Actin 2 ("Act2") promoter and terminator (GenBank Accession No. U41998.1, which is hereby incorporated by reference in its entirety), and the Arabidopsis *thaliana* Rubisco Small Subunit ("AtRbcS") signal peptide (GenBank Accession No. AY097366.1, which is hereby incorporated by reference in its entirety); a gene encoding malate synthase from *Cucurbita* sp. Kurokawa Amakuri Nankin (SEQ ID NO:4) operably linked to the *Zea maize* Suppressor Mutator ("Spm") promoter (GenBank Accession No. M25427.1, which is hereby incorporated by reference in its entirety), the AtRbcS signal peptide, and the *Agrobacterium tumifaciens* Octopine Synthase ("OCS") terminator (GenBank Accession No. CP033030.1, which is hereby incorporated by reference in its entirety); and an RNAi polynucleotide sequence (SEQ ID NO:8 and SEQ ID NO:9) targeting an endogenous glycolate/glycerate transporter Plgg1 separated by a PDK intron and operably linked to the *Arabidopsis thaliana* Rubisco Small Subunit 2 (AtRbcs2b) promoter (GenBank Accession No. X14564.1, which is hereby incorporated by reference in its entirety), and the Act2 terminator were transformed into *Agrobacterium tumefaciens*. The construct pLC0102 is shown in FIG. 7 and the Plgg1 RNAi cassette is shown in FIG. 3. FIG. 8 illustrates a construct with GDH and MS, which is useful for addition of other Plgg1 RNAi cassettes.

Figure 9:
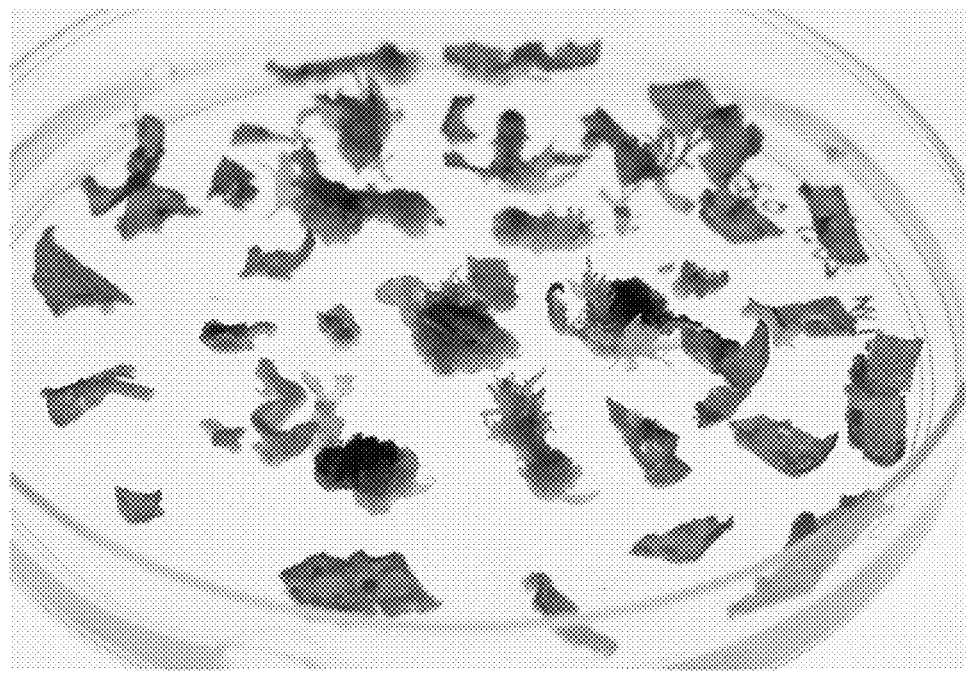
FIG. 9 is a photograph of regenerated transgenic *Populus tremula* x *Populus alba* shoots transformed with pLC0102.

Recombinant *Agrobacterium tumefaciens* colonies transformed with pLC0102 were cultured for 24 hours on an orbital shaker. Leaves of the hybrid *Populus tremula* x *Populus alba*, clone INRA 717-1B4 were collected and used to grow stem explants. Stem explants were swirled in the *Agrobacterium* suspensions for 1 hour, and then co-cultured on agar medium for 48 hours at 24° C. in darkness. The explants were washed four times in 50 ml centrifuge tubes with deionized water at 125 rpm at 24° C., transferred to growth media with antibiotics for 21 days at 24° C. in darkness, and then transferred to standard light conditions 16 h light/8 h dark to recover green calli. The green calli were transferred to agar medium containing antibiotics for generation and selection of transformed shoots as shown in FIG. 9. The regenerated shoots were excised when they were approximately 1 cm long and transferred to agar medium supplemented with antibiotics for rooting. After 5-8 weeks, the rooted and elongated shoots were propagated on the same medium. Rooted LC0102 transgenic plants were transferred out of Magenta boxes in tissue culture into soil pots, acclimated, and grown under inverted diurnal cycle. A total of 41 stable pLC0102 T0 transgenic events were evaluated and further propagated.

Eight weeks post potting, T0 plants went through a vegetative propagation cycle using a stem cutting method frequently used in horticulture practice. Briefly, the apical meristem was removed to release the apical dominance to stimulate the formation of axillary buds to produce branches. The axillary branches were cut and inserted into rockwool cubes for support to produce roots in hydroponic conditions. To maintain the genetic lineage of transgenic lines, cuttings from the T0 plant were named C1 plants with C1.1 referring to apical cutting and C1.2 and so on referring to axillary cuttings. C1 cuttings normally established root systems after approximately two weeks in hydroponic conditions and would then be transferred to soil pots for C1 plant evaluations. Multi branches or cuttings produced from one T0 mother plant are sister C1 plants called ramets, serving as biological replicates for C1 evaluation.

Example 3—Transgenic Plant Phenotypes and Gene Expression Analysis

T0 leaf tissue samples were collected from transgenic trees as they were transferred out of Magenta boxes for the evaluation of gene expression. C1 leaf tissue samples were collected from 8 week old transgenic plants grown in soil pots in a controlled environment. Total RNA was extracted from leaf tissue samples using the NucleoSpin RNA Plants and Fungi extraction kit (Takara Bio Inc., Kusatsu, Japan). Quantitation of genomic DNA and total RNA was performed on a Nanodrop 1000 spectrophotometer (Thermo Fisher Scientific, Waltham, Mass.) following the manufacturer's protocol.

cDNA was generated from T0 RNA samples, and singleplex qRT-PCR analysis was performed to quantify Plgg1 reduction in the transgenic plants using the SYBR green RT kit from (Qiagen, Hiden, Germany). Briefly, a 20 µl RT-PCR reaction was assembled with 10 µl 2× SYBR Green RT-PCR Master Mix, 0.2 µl QN SYBR Green RT-Mix, 1 µl of 20× gene specific primer mix, 0.2 µl QN ROX dye, 1 µl 100 n g/µl template RNA, and 7.6 µl RNase-free ddH2O. The reaction wells were then placed in a Chai PCR machine (Chai, Santa Clara, CA) for PCR amplification with the following cycling program: Step 1, 50° C., 10 minutes; Step 2, 95° C., 2 minutes; Step 3, 95° C., 5 seconds; Step 4, 60° C., 10 seconds, repeating Step 3 to Step 4 for 40 cycles. Data acquisition and analysis was performed with the Chai machine. For each gene of interest, two RT-PCR reactions are prepared in parallel, one with the primer set to amplify the gene of interest, the other with the primer set to amplify the housekeeping gene ACT2. The level of gene expression was reflected by the Cq value generated from the RT-PCR reaction. Higher Cq value indicates lower level of expression.

Primers used for analyzing gene expression using the QuantiNova SYBR Green qRT-PCR kit are shown in Table 1.

TABLE 1

Primers Used for Gene Expression Analysis Using SYBR Green qRT-PCR

| Gene Target | SEQ ID NO: | Sequence (5' to 3') |
| --- | --- | --- |
| Plgg1 | 10 | CAGGTGTCAAGATTTGCTTCATC |
|  | 11 | ACTCCAAGCCCACATTTCC |
| PtACT2 | 12 | ACTGAGACCATCACCAGAATC |
|  | 13 | CTCAACCCTAAGGCTAACAGAG |
| ChMS | 14 | CCACATAAGGTATTCGATGGAATGC |
|  | 15 | GACTGATGCACATGTCCACTC |
| CrGDH | 16 | CACATCAAGTTCCTGAAGCCCTC |
|  | 17 | ATCTCGCGGTACACGGAGATG |
| nptII | 18 | CCTGCCGAGAAAGTATCCATC |
|  | 19 | CATCCTGATCGACAAGACCG |

The expression analysis of transgenes via qRT-PCR was performed with T0 RNA samples using a Chai PCR machine (Chai, Santa Clara, CA). The expression level of the housekeeping gene ACT2 was similar among transgenic events and non-transgenic controls, whereas the expression level of transgenes and Plgg1 varied among different transgenic events. Expression data generated using SYBR Green assay demonstrated that 39 of the 41 transgenic events expressed all four genes in the pLC0102 construct. Table 2 shows the results of the relative gene expression level for transgene nptII, ChMS, and CrGDH as determined by the Cq value using SYBR green qRT-PCR assay. Non-transgenic controls CT717-1 and CT717-2 showed no expression of any of the transgenes, as expected, since they do not contain any of the transgene expression cassettes. Transgenic events 8-9, 8-9D, 16-20, and 16-20B showed no expression of transgenes, indicating they were transformation escapes (Table 2).

The 37 independent true transgenic events all showed varied Cq values indicating varied expression levels. As the primer efficiency for each gene is different, the Cq value of transgene A is only useful for comparison of relative expression level of transgene A among the transgenic events. Cq values are not useful for cross comparison of different transgenes in this case. Transgene expression level is summarized in Table 2 as 5 categories, with "+" indicating the lowest expression group and "+++++" indicating the highest expression group among the 37 transgenic events.

The expression level of the endogenous Plgg1 in transgenic events and non-transgenic control plants was also analyzed with T0 RNA samples using a Chai PCR machine (Chai, Santa Clara, CA). This analysis reveals the effectiveness of RNAi design in LC0102 construct. In this analysis, the expression level of Plgg1 in non-transgenic control plants is designated as 100% or 1.0-fold. Transgenic events harboring the RNAi design construct express RNAi at various levels and subsequently have various degrees of reduction effect on the expression of endogenous Plgg1.

Table 2 summarizes the relative expression level of Plgg1 in various transgenic events. Relative expression of Plgg1 is indicated with + symbols: +, less than 30%; ++, 30% to 60%; +++: 60% to 90%; ++++, 90% to 150%; +++++, greater than 150%. In the lowest Plgg1 expression group ("+" relative expression level in Table 2), events LC0102.2C and 2G show that the level of Plgg1 expression is approximately 10% of that of the non-transgenic control, reflecting a strong RNAi inhibition.

Analysis of plant morphology and the corresponding level of Plgg1 expression data generated using the Chai platform is shown in Table 2. It was found that transgenic plants with high reduction of Plgg1 with the lowest level of expression ("+", <30% of the Plgg1 expression of control plants, such as LC0102.2C, 2G, 2A, 3C, 5F, 5E, 3H, and 13-15B) were more likely to show abnormal plant morphologies compared to controls. Transgenic events with normal or abnormal plant morphologies such as dwarfism are indicated in Table 2. Controls, including non-transgenic plants CT717-1 and CT717-2, and escapes from plant transformation with no expression of transgenes (LC0102.8-9, 8-9D, 16-20, and 16-20B) all showed normal plant morphologies. It was determined that most transgenic plants had normal morphologies with Plgg1 expression of at least 30% of that of control plants. Further reduction of Plgg1 expression greater than about 30% (i.e., Plgg1 expression only 0-20% of Plgg1 expression in control plants) would likely render plants with abnormal morphologies.

Figure 10:
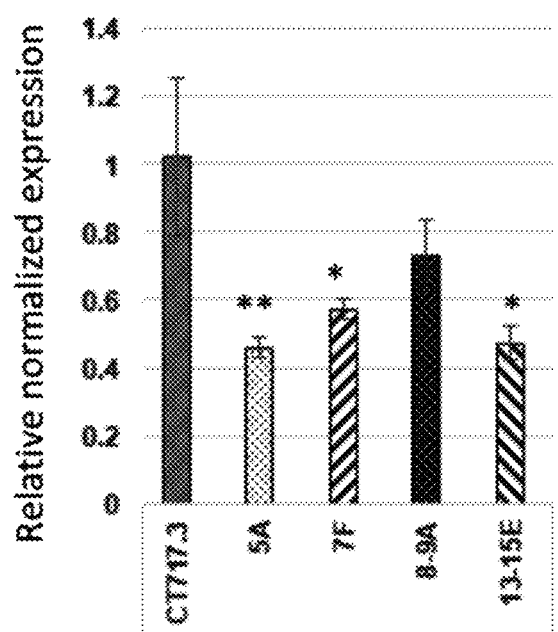
FIG. 10 is a graph showing the expression level of Plgg1 in lead LC0102 events. Expression levels of events LC0102.5A, 7F, 8-9A, and 13-15E had reduced levels of Plgg1 ranging from 46% to 73% of Plgg1 expression in the control (wild-type). Tissue samples were collected from three ramets per event except for two ramets for event 13-15E. The symbols * and ** indicate statistically significant differences at $p<0.05$ and $p<0.01$, respectively, when compared to non-transgenic CT717.3. Statistical analysis was performed based on one-way ANOVA.

Quantitative measurement of Plgg1 expression in transgenic events showing enhanced growth. As described in Example 2, vegetative propagation of T0 events was performed using stem cuttings to generate C1 plants. Total RNA prepared from leaf samples of selected groups of 8-week old C1 plants (transgenic events LC0102.13-15E, 5A, 7F, and 8-9A, and non-transgenic plants CT717.3) was analyzed for Plgg1 expression using a CFX Opus 96 Real Time PCR system (BioRad, Hercules, CA) in a multiplex assay with probe primers. Relative Plgg1 expression level was determined using the comparative CT method or ΔΔCT method with ACT2 as the reference gene (Schmittgen and Livak, "Analyzing Real-Time PCR Data by the Comparative CT Method," *Nature Protocols* 3:1101-1108 (2008), which is hereby incorporated by reference in its entirety). FIG. 10 shows the expression level of Plgg1 in these plants. Three of the four transgenic events show significant differences in the level of Plgg1 expression compared to that of the non-transgenic control CT717.3, for which the expression level was designated as 1.0. In event 13-15E, 5A, and 7F, the average level of Plgg1 expression was reduced to 0.47, 0.46, and 0.57 (or 47%, 46%, and 57%), respectively, compared to the control. The expression level of Plgg1 in event 8-9A was also reduced (average value 0.73, or 73% of the control levels) but was not statistically significant.

TABLE 2

Plant Phenotypes and Relative Gene Expression in Transgenic Events

| Event Name | Relative Expression | | | | Plgg1 Fold Expression | Plgg1 qRT-PCR Repeats | T0 phenotype |
| --- | --- | --- | --- | --- | --- | --- | --- |
| | nptII | ChMS | CrGDH | Plgg1 | | | |
| LC0102.2C | ++++ | +++++ | +++ | + | 0.11 | 2 | Dwarf |
| LC0102.2G | +++++ | +++++ | ++ | + | 0.11 | 1 | >10 leaves fell off? |
| LC0102.2A | +++ | ++++ | ++ | + | 0.15 | 2 | Double tree |
| LC0102.3C | +++ | ++++ | ++ | + | 0.16 | 1 | Branches |
| LC0102.5F | +++ | ++++ | +++ | + | 0.18 | 2 | Branches |
| LC0102.21-25A | +++ | +++ | +++ | + | 0.19 | 2 | Normal |
| LC0102.5E | ++++ | +++++ | +++ | + | 0.19 | 1 | Branches |
| LC0102.3H | +++ | ++++ | ++ | + | 0.22 | 2 | Snaky |
| LC0102.13-15 B | ++ | ++++ | + | + | 0.23 | 2 | Forest |
| LC0102.2H | ++++ | ++++ | +++ | ++ | 0.31 | 1 | Branches |
| LC0102.5A | ++++ | +++++ | ++ | ++ | 0.32 | 2 | Normal |
| LC0102.21-25E | ++++ | +++++ | +++ | ++ | 0.33 | 1 | Normal |
| LC0102.68 | +++ | ++++ | +++ | ++ | 0.36 | 2 | Normal |
| LC0102.5C | +++++ | +++++ | ++++ | ++ | 0.37 | 1 | Branches |
| LC0102.6 | ++ | ++ | ++ | ++ | 0.40 | 2 | Branches |
| LC01022 | +++ | +++ | +++ | ++ | 0.58 | 3 | Normal |
| LC0102.1 | +++++ | +++ | +++ | ++ | 0.60 | 2 | Normal |
| LC0102.3 | ++++ | +++ | ++++ | ++ | 0.60 | 2 | Branches |
| LC0102.5 | +++ | ++ | +++ | +++ | 0.67 | 3 | Normal |
| LC0102.4G | +++ | +++++ | ++ | +++ | 0.68 | 1 | Normal |
| LC0102.2F | ++ | +++++ | + | +++ | 0.7 | 1 | Moldy |
| LC0102.1B | +++ | ++++ | + | +++ | 0.79 | 2 | Normal |
| LC0102.1C | +++++ | +++ | ++++ | +++ | 0.85 | 1 | Normal |
| LC0102.13-15 | ++ | +++ | +++ | ++++ | 0.95 | 1 | Drought induced abnormality |
| LC0102.4 | +++ | ++ | ++ | ++++ | 0.96 | 2 | Normal |
| LC0102.16-20B | − | − | − | ++++ | 1.00 | 2 | Branches |

TABLE 2-continued

Plant Phenotypes and Relative Gene Expression in Transgenic Events

| Event Name | Relative Expression | | | | Plgg1 Fold Expression | Plgg1 qRT-PCR Repeats | T0 phenotype |
|---|---|---|---|---|---|---|---|
| | nptII | ChMS | CrGDH | Plgg1 | | | |
| CT717-1. | − | − | − | ++++ | 1 | 5 | Normal |
| LC0102.4A | +++ | ++++ | + | ++++ | 1.13 | 5 | Normal |
| LC0102.7 | ++++ | ++ | + | ++++ | 1.17 | 1 | Normal |
| LC0102.4B | ++++ | +++++ | ++ | ++++ | 1.22 | 2 | Branches |
| LC0102.8-9A | +++ | ++++ | +++ | ++++ | 1.24 | 1 | Normal |
| CT717-2 | − | − | − | ++++ | 1.28 | 1 | Normal |
| LC0102.3F | +++ | +++++ | +++ | ++++ | 1.38 | 3 | NA |
| LC0102.3B | +++ | ++++ | + | ++++ | 1.48 | 1 | Forest |
| LC0102.3D | ++ | +++++ | +++ | ++++ | 1.51 | 1 | Normal |
| LC0102.1A | +++++ | ++++ | +++++ | +++++ | 1.59 | 1 | Normal |
| LC0102.6D | ++++ | +++++ | ++++ | +++++ | 1.6 | 1 | Normal |
| LC0102.1D | ++++ | +++++ | +++ | +++++ | 1.93 | 1 | Normal |
| LC0102.16-20 | − | − | − | +++++ | 2.01 | 1 | Branches |
| LC0102.7F | +++ | ++++ | ++ | +++++ | 2.6 | 1 | Normal |
| LC0102.8-9 | − | − | − | +++++ | 2.69 | 1 | Normal |
| LC0102.13-15E | +++ | ++++ | +++ | +++++ | 2.99 | 1 | Normal |
| LC0102.8-9D | − | − | − | +++++ | 3.36 | 1 | Branches |

Example 4—Multiplex Real-Time Gene Expression Analysis

Multiplex qRT-PCR analysis with technical duplicates in each event using CFX Opus 96 machine (Bio-Rad) was used for gene expression analysis of Plgg1, CrGDH, and ChMS. The 20 μL reaction contains 200 ng total RNA, 1× custom made One-Step RT-qPCR Master Mix with lower amount of DTT (Launchworks), primers, and probes (Table 3). qRT-PCR was performed with the following conditions: 53° C., 10 mins, reverse transcription; 95° C., 2 mins, initial denaturation; 40 cycles amplification (15 secs 95° C. denaturation; 30 secs 60° C. annealing/extension). Reference genes were selected based on expression evaluation in leaves of various developmental stages. Average Cq of the selected reference genes were used for ΔCq calculation. The $2^{(-\Delta\Delta Cq)}$ method was used to analyze the expression data.

Primers sets (each containing a forward primer, probe, and reverse primer) used for multiplex gene expression analysis are listed in Table 3. PtaAct2 (Potri.001G309500 sPta717), PtaEF1B-1 (Potri.001G224700 sPta717) were selected as reference genes.

TABLE 3

Probe Primers for Multiplex Gene Expression Analysis

| Gene Target | SEQ ID NO: | Sequence (5' to 3') |
|---|---|---|
| Plgg1 | 20 | CAGGTGTCAAGATTTGCTTCATC |
| | 21 | FAM/CTTTGCGTG/ZEN/GCGGGTTTCACAG/3IABkFQ |
| | 22 | AGCGTCAGTCATTTCTGTCTT |
| PtACT2 | 23 | CTGCAATGTATGTTGCCATCC |
| | 24 | HEX/ACTGGCATA/ZEN/CAGGGAAAGGACAGC/3IABkFQ |
| | 25 | CACACCATCACCAGAATCCA |
| PtEF1B-1 | 26 | CATCACTACCACTCCACACAA |
| | 27 | Quasar 705/TCCTCTTTC/NOVa/AATCACACTGTTTATCGCTCT/3BHQ |
| | 28 | TTTCAATTACTTGGAAGATGGGATG |
| CrGDH | 29 | AAGGCGTACGAGCTGATG |
| | 30 | Cy5/AACCCGGGC/TAO/GTCATCCTCAA/3IAbRQSp |
| | 31 | GAGGGCTTCAGGAACTTGAT |
| ChMS | 32 | ATGGAATGCCGCAGAGAAG |
| | 33 | Texas Red-XN/ATACTTGGTCGCCGGATCAAACCC/3TAbRQSP |
| | 34 | GATGCACATGTCCACTCAGAT |

Example 5—Photosynthetic Efficiency Measurements

Transgenic seedlings were planted in pots and grown under greenhouse conditions, or planted in the field, with wild type (WT) and empty vector control (CT) seedlings used for comparisons. Weather data, including light intensity, air temperature, and precipitation, were measured.

Starting at one week post potting, morphology evaluations were carried out for greenhouse grown plants on a weekly basis including height measurement, leaf number counting, and phenotypic analysis. Eight weeks post potting, T0 plants went through a vegetative propagation cycle. Briefly, apical meristem was removed to release apical dominance and stimulate the formation of axillary buds leading to branch production for the next rounds of seedling production via stem cutting and hydroponic rooting. To indicate the genetic lineage of transgenic lines, cuttings from T0 plants were named C1 plants with C1.1 referring to the apical cutting and C1.2 and so on referring to axillary cuttings. C1 cuttings normally established root systems after approximately two weeks and would be transferred to soil pots afterwards. Morphological evaluations were performed similarly with T0 plants.

Measurements of $CO_2$ assimilation were conducted using the LI-6800 portable fluorometer following the manufacturer's manual (licor.com/env/support/LI-6800/manuals.html, LI-COR, Lincoln, Nebr.). Briefly, the LI-6800 $CO_2$ response program was used for measurement of the A-Ci curves with the reference $CO_2$ concentrations set to 400, 40, 20, 40, 60, 80, 100, 150, 200, 300, 400, 500, 700, 900, 1,100, 1,300, 1,500, and 2,000 ppm. Minimum and maximum wait times were set at 60 to 120 s based on the stability of the $CO_2$ net assimilation rate and the difference between sample and reference $CO_2$ concentrations. The reference and sample infrared gas analyzers (IRGAs) were matched before the measurement at each concentration. The measured leaf was allowed to acclimate at 400 ppm for ~5 min. The light intensity was set at 1,500 μmol/m$^2$/s.

Figure 11:
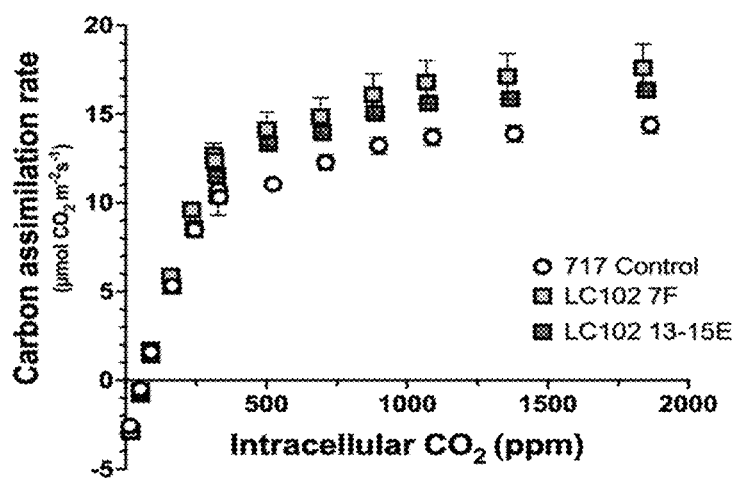
FIG. 11 is a graph of $CO_2$ assimilation curves, or A-Ci curves, measuring photosynthesis efficiency of 18 week old plants including non-transgenic 717 controls and two lead LC0102 events, 13-15E, and 7F. Number of ramets measured: 717 control plants, 5; 13-15E, 2; 7F, 3. Error bars indicate SEM.

Photosynthesis rate is increased in the LC0102 plants. The $CO_2$ assimilation rate was measured on 18 weeks-old plants grown in a controlled environment using the LI-6800. As shown in FIG. 11, plants of two transgenic events, 13-15E and 7F, show elevated levels of carbon assimilation in saturated intracellular $CO_2$ concentrations. As discussed in Example 6, this elevated level of carbon assimilation rate led to faster growth of plants and increased biomass production.

Example 6—Tree Growth and Biomass Measurements

Figure 12:
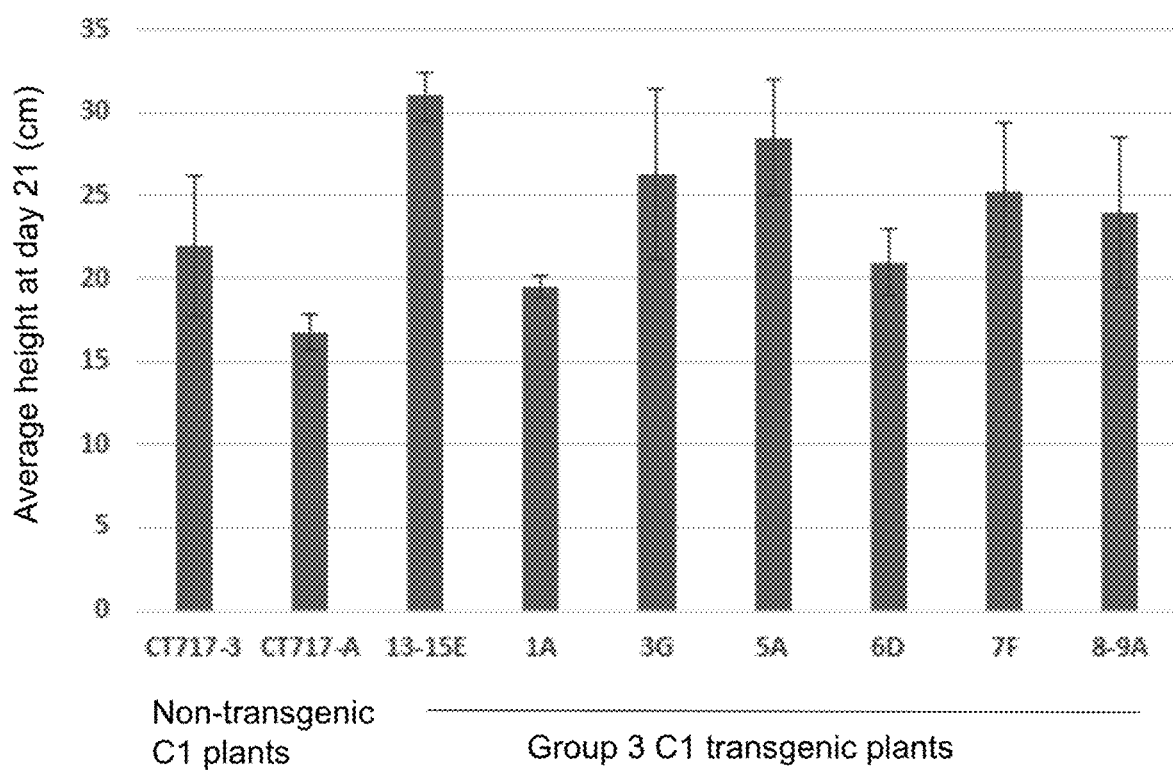
FIG. 12 is a graph illustrating the average heights of triplicate control and selected transgenic LC0102 events measured 3 weeks after transfer to soil pots.

Transgenic plants harboring the T-DNA from LC0102 grew faster. Measurement of plant growth was performed one week post soil transplantation on a weekly basis. Areas of growth measurement included plant height, root collar diameter (RCD), leaf number, SPAD readings, and other measurements. Plants of several LC0102 transgenic events started to display faster growth early, as reflected by height increases. FIG. 12 shows height measurement results of Group 3 transgenic plants 3 weeks after being transferred to soil pots. Transgenic events LC0102.13-15E, 5A, 7F, and 8-9A showed, respectively, a 40%, 14%, 27%, and 10% increase in height after 3 weeks growth in a controlled environment compared to non-transgenic control plant CT717-3.

Transgenic plants harboring LC0102 grew into taller trees over time. Plants of four selected LC0102 events (13-15E, 5A, 7F, and 8-9A) along with non-transgenic control 717 were carried forward for extended growth evaluations in a high ceiling growth room. FIG. 13A is a photograph of plants grown in soil for 17 weeks. Transgenic plants were taller than non-transgenic control plants. FIG. 13B is a graph showing that the early observed growth advantage in LC0102 events continued to be reflected in plant height after 17 weeks. Compared to non-transgenic controls, events 13-15E, 7F, and 8-9A were significantly taller displaying a 18%, 15%, and 10% respective increase in height after 4 months, with p-values less than 0.01 (13-15E and 7F) or 0.05 (8-9A) (FIG. 12B). One ramet of event 5A was as tall as plants of 13-15E, however, the variation among the three ramets was too great to render a higher p-value.

The increased growth rate of these trees allows the reduction of the growth cycle from 10-12 to 6-7 years. Both carbon drawdown and wood production in forest trees are directly dependent on growth rate, so this also represents up to a 40% increase in both.

Transgenic plants harboring LC0102 had increased biomass production. Four selected LC0102 events, 13-15E, 5A, 7F, and 8-9A, along with non-transgenic CT717 plants were selected for morphology evaluation after an extended growth period in a controlled environment. At 21 weeks post-potting, plants were harvested for biomass measurements. Fresh weight (FW) and dry weight (DW) were measured for leaf, root, and stem tissues separately, and the data is summarized in FIGS. 14A-B. As shown, lead event 13-15E had significantly higher biomass production in all tissue types at both FW (FIG. 14A) and DW (FIG. 14B) levels, with above ground (AG) DW showing a 53% increase over that of non-transgenic CT717 control plants. Lead event 7F also had significantly higher biomass production in stem and roots at both FW and DW levels, but not in leaves. Event 5A and 8-9A did not show significantly higher biomass production.

The expression analysis of C1 plants indicated Plgg1 expression levels of 47%, 46%, 57%, 73% compared to Plgg1 expression in control plants for events 13-15E, 5A, 7F, and 8-9A, respectively, as shown in FIG. 10. As shown in FIG. 14B, event LC0102.13-15E had a 53% increase in AG dry biomass production compared to the control. In Table 2, it was demonstrated that too much reduction in Plgg1 expression would lead to abnormalities in plant growth phenotypes. Taken together, in order to achieve significantly enhanced biomass production in engineered poplar trees with good morphology, a significant reduction in the expression level of Plgg1 (such as a 53% reduction (i.e., Plgg1 expression of 47% compared to Plgg1 expression in a control plant)) is beneficial. Slightly reduced Plgg1 expression did not lead to significantly enhanced biomass production. Reduction of Plgg1 expression by about 80% or more (i.e., Plgg1 expression of 20% or less compared to Plgg1 expression in a control plant) was found to be more likely to lead to growth abnormalities in engineered plants.

Example 7—Plgg1 Expression in Field-Grown Trees

At least 30 ramets each of at least 10 different transgenic poplar tree events as well as the same or larger numbers of non-transgenic controls of the same genotype were acclimated outdoors, and planted in fields. Transgenic trees included ramets from events 1C, 2H, 4A, 5A, 7, 13-15B, 13-15E, and 5C. Control ramets were from were from non-transgenic control 717 (CT717-3), and transgenic escapes (i.e., not having a transgene) including 16-20 and 8-9D.

Trees were randomly selected from the field for gene expression studies after 12 months of growth. Samples were collected from leaf 10 (counting from the top) of each tree. Samples were processed with total RNA extraction, quantitation, normalization, and qRT-PCR analysis using primers shown in Table 3. Relative fold expression was determined using standard ΔΔCT method, and the results are shown in Table 4.

TABLE 4

Relative Expression Level of Plgg1 in Field-Grown Trees

| Event | # Trees | Average Fold Expression of Plgg1 Relative to Control (& % Plgg1 Expression Relative to Control) | Std deviation |
|---|---|---|---|
| 1C | 9 | 1.05 (105 %) | 0.20 |
| 2H | 11 | 0.15 (15 %) | 0.05 |
| 4A | 11 | 0.68 (68 %) | 0.23 |
| 5A | 12 | 0.45 (45 %) | 0.11 |
| 7 | 11 | 0.79 (79 %) | 0.17 |
| 8-9D | 12 | 0.76 (76 %) | 0.16 |
| 13-15B | 10 | 0.16 (16 %) | 0.14 |
| 13-15E | 11 | 0.16 (16 %) | 0.06 |

TABLE 4-continued

Relative Expression Level of Plgg1 in Field-Grown Trees

| Event | # Trees | Average Fold Expression of Plgg1 Relative to Control (& % Plgg1 Expression Relative to Control) | Std deviation |
|---|---|---|---|
| 16-20 | 12 | 0.96 (96 %) | 0.23 |
| CT717-3 | 11 | 0.97 (97 %) | 0.14 |
| 5C | 15 | 0.49 (49 %) | 0.11 |

Plgg1 expression level in non-transgenic CT717-3 trees was designated as 1.0 fold or 100%. With the exception of event 1C which has similar level of Plgg1 expression to the control, transgenic events in general had reduced Plgg1 expression ranging from 15% to 79% of that of the control. This represented an expression reduction of 21% to 85%. Events 13-15B, 13-15E, and 2H showed the greatest reduction of Plgg1 gene expression at around 84%.

A statistical analysis of Plgg1 gene expression in field-grown trees was conducted as shown in Table 5. Statistical difference was calculated by Dunnett's test for pairwise comparisons to CT717-3. The level of significance in difference between events are indicated with p-value and noted with asterisks: ns, $p>0.05$; *, $p\leq0.05$; , $p\leq0.01$; *, $p\leq0.001$; ****, $p\leq0.0001$.

TABLE 5

Statistical Analysis of Plgg1 Expression in Field-Grown Trees

| Dunnett's T3 Multiple Comparisons Test | Mean Diff. | 95.00% CI of diff. | Below Threshold? | Summary | Adjusted P Value |
|---|---|---|---|---|---|
| CT717-3 vs. 1C | −0.06089 | −0.3254 to 0.2036 | No | ns | 0.9946 |
| CT717-3 vs. 2H | 0.8575 | 0.7101 to 1.005 | Yes | **** | <0.0001 |
| CT717-3 vs. 4A | 0.3154 | 0.05697 to 0.5739 | Yes | * | 0.0119 |
| CT717-3 vs. 5A | 0.5532 | 0.3883 to 0.7182 | Yes | **** | <0.0001 |
| CT717-3 vs. 7 | 0.2076 | −0.0008545 to 0.4610 | No | ns | 0.0514 |
| CT717-3 vs. 8-9D | 0.2247 | 0.02400 to 0.4253 | Yes | * | 0.0221 |
| CT717-3 vs. 13-15B | 0.8455 | 0.6539 to 1.037 | Yes | **** | <0.0001 |
| CT717-3 vs. 13-15E | 0.8563 | 0.7109 to 1.002 | Yes | **** | <0.0001 |
| CT717-3 vs. 16-20 | 0.01099 | −0.2421 to 0.2641 | No | ns | >0.9999 |
| CT717-3 vs. 5C | 0.5108 | 0.3528 to 0.6689 | Yes | **** | <0.0001 |

Example 8—Growth Performance of Engineered Trees in the Field

Figure 15A:
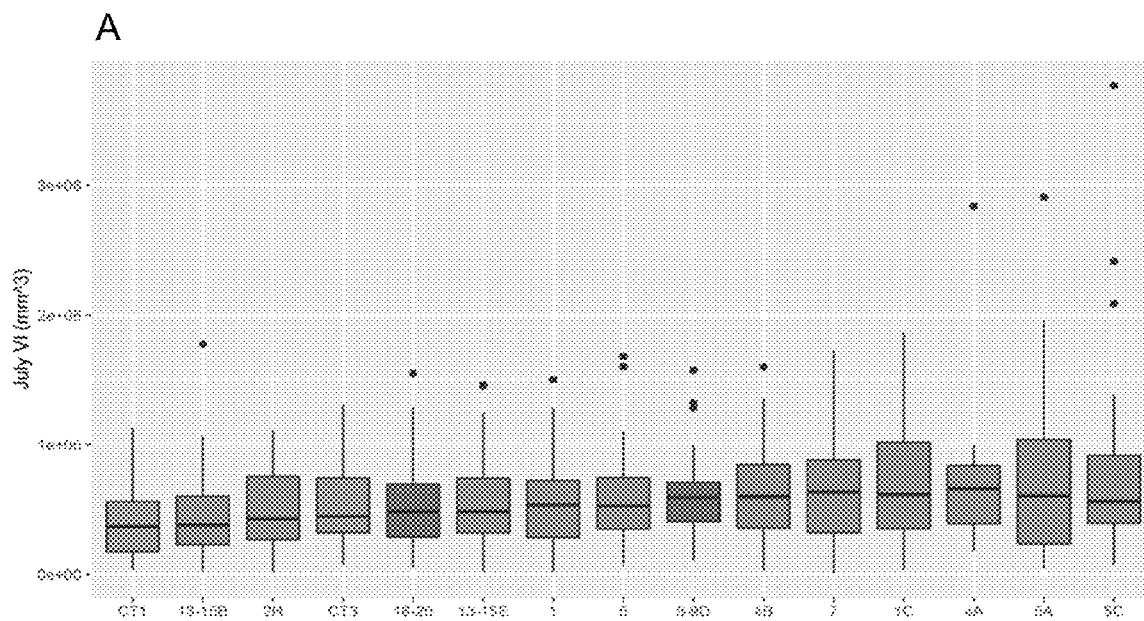
FIGS. 15A-B are graphs showing stem volume index ($mm^3$) measured approximately 1 year after transplantation in a field environment in July (FIG. 15A) and August (FIG. 15B) for various transgenic events (13-15B, 2H, 13-15E, 1, 5, 4B, 7, 1C, 4A, 5A, and 5C), non-transgenic controls (CT1 and CT3), and escapes (16-20, 8-9D (having no transgene)).
Figure 15B:
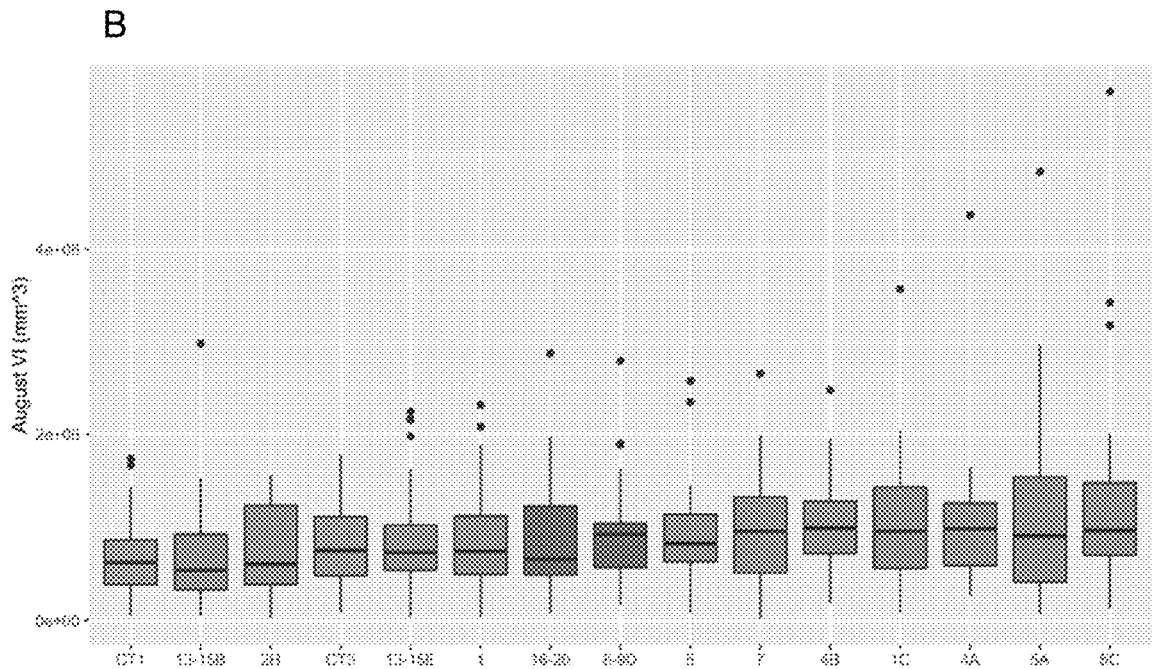

FIGS. 15A-B show graphs illustrating growth performance of engineered trees in the field. Stem volume index was generated from measurements of plant height and root collar diameter (V=diameter$^2$×height). Data was collected from all trees in the field by the S. Strauss laboratory at Oregon State University, which included 35 to 44 trees per event.

FIG. 15A shows the stem volume index (mm$^3$) measurements in July approximately 1 year after transplantation. FIG. 15B shows the stem volume index (mm$^3$) measurements in August of the same year.

The transgenic events showed an upward trend in stem volume index compared to controls. Four transgenic events, 1, 13-15B, 13-15E, and 2H, showed stem volume index increases similar to transgenic escapes (16-20 and 8-9D) and non-transgenic controls (CT1 and CT3). Other transgenic events, including 4B, 7, 1C, 4A, 5A, and 5C had higher stem volume growth. Transgenic events 13-15B, 13-15E, and 2H had the lowest volume increases of all the transgenic events, and were also the events that had the most severely reduced Plgg1 expression under field growth conditions (expression levels were 16%, 16%, and 15%, respectively, of control Plgg1 expression, see Table 4). Whereas the top three performing transgenic events 5C, 5A, and 4A, had moderately reduced Plgg1 gene expression (expression levels were 49%, 45%, and 68%, respectively, of control Plgg1 expression, see Table 4).

Example 9—Glycolate Dehydrogenase (CrGDH) and Malate Synthase (ChMS) Expression in Field Grown Transgenic Trees Relative expression levels of Glycolate Dehydrogenase (CrGDH) and Malate Synthase (ChMS) in various transgenic events and non-transgenic controls is shown in FIGS. 18B-C. In comparison, expression of endogenous Plgg1 in various transgenic events and non-transgenic controls is shown in FIG. 18A. CrGDH expression is similar among different events, with relative gene expression values ranging from 0.76 to 1.41 (FIG. 18B, and Table 6). Malate synthase expression ranges from a relative gene expression of 0.9 to 1.59 (FIG. 18C and Table 7). There is no expression of CrGDH nor ChMS in non-transgenic control CT717-3 and escapes as they do not contain these genes. Tables 6 and 7 show the number of ramets analyzed, the average normalized expression, and the standard deviation for CrGDH (Table 6) and ChMS (Table 7).

TABLE 6

GDH Expression in Various Events and Controls

| Event | Ramets | Average | Std deviation |
|---|---|---|---|
| 1C | 9 | 1.12 | 0.12 |
| 2H | 11 | 1.41 | 0.42 |
| 4A | 11 | 0.7553 | 0.13 |
| 5A | 12 | 0.88 | 0.15 |
| 7 | 11 | 1 | 0.08 |
| 8-9D | 12 | 0 | N/A |
| 13-15B | 10 | 0.76 | 0.26 |
| 13-15E | 11 | 1.31 | 0.37 |
| 16-20 | 12 | 0 | N/A |
| CT717-3 | 11 | 0 | N/A |
| 5C | 15 | 1.03 | 0.14 |

TABLE 7

MS Expression in Various Events and Controls

| Event | Ramets | Average | Std deviation |
|---|---|---|---|
| 1C | 9 | 1.57 | 0.37 |
| 2H | 11 | 1.59 | 0.20 |
| 4A | 11 | 1.3811 | 0.28 |
| 5A | 12 | 0.79 | 0.13 |
| 7 | 11 | 1.02 | 0.22 |
| 8-9D | 12 | 0 | 0.00 |
| 13-15B | 10 | 0.83 | 0.28 |
| 13-15E | 11 | 1.03 | 0.14 |
| 16-20 | 12 | 0 | 0.00 |
| CT717-3 | 11 | 0 | N/A |
| 5C | 15 | 1 | 0.22 |

Example 10—Comparison Between Transgenic Event 13-15E and Controls

A comparison between transgenic event 13-15E and non-transgenic control over five experiments is shown in Table 8. Across five experiments conducted in growth room, greenhouse, and field conditions, transgenic event 13-15E was compared to non-transgenic controls. A strong correlation was identified between the degree of Plgg1 expression reduction and the growth performance of 13-15E.

Under experimental conditions when Plgg1 was severely reduced such as in the field and some greenhouse experiments (having only 8% or 16% of the Plgg1 expression level in controls), 13-15E plants did not show a significantly better growth advantage in stem volume increase compared to non-transgenic control plants (Table 8). In experiments when the stem volume difference of event 13-15E was significant, a less-severe degree of Plgg1 expression reduction in 13-15E plants was observed (having 47%, 30%, and 27% Plgg1 expression compared to controls) (Table 8). In all these experiments, expression levels of the other two transgenes CrGDH and ChMS were very similar (Table 8). These results further support the importance of a moderate down-regulation of endogenous Plgg1 expression. Reduction of Plgg1 expression to 20% or less of the expression level of Plgg1 in a control plant, can lead to severe detrimental morphological effects and/or lack of growth benefits to the plants when co-expressed with malate synthase and glycolate dehydrogenase.

TABLE 8

Comparison of Gene Expression in Event 13-15E in Different Environments

| Experiment | Location | Expression of CrGDH (dCq) | Expression of ChMS (dCq) | Plgg1 % Expression Relative to Controls | Stem Volume Significantly Higher than Controls? |
|---|---|---|---|---|---|
| C2 Exp | Growth Room (location 1) | $-5.50 \pm 0.35$ | $-3.82 + 0.65$ | 27% | Yes |
| Field Year 2 | Field (location 3) | $-6.65 \pm 0.37$ | $-3.71 \pm 0.19$ | 16% | No |
| Pilot 1 | Greenhouse (location 2) | $-5.12 \pm 0.18$ | $-4.05 \pm 0.18$ | 30% | Yes |
| Pilot 2 | Greenhouse (location 2) | $-5.80 \pm 0.48$ | $-4.14 \pm 0.40$ | 8% | No |
| C1 Exp | Growth Room (location 1) | NA | NA | 47% | Yes |

Example 11—Transgenic Events have Higher Photosynthetic Activity & Stomatal Conductance Under Drought Conditions Transgenic plants, including 4 plants of event 13-15E, and 1 plant of event 7, as well as 4 plants of non-transgenic control CT7-717-3 were grown for twelve weeks in a controlled environment. Plants were watered to saturation before the start of the experiment. Across 4 days, plants were watered overnight with minimal water to keep them alive, but not saturated. Each plant was measured with a Licor LI-6800 photosynthesis system twice a day with full A-Ci ($CO_2$ assimilation) curves. Soil moisture was recorded with a soil moisture probe during each measurement. Soil moisture was categorized into drought severity levels: None (>9.5), Mild (7.5-9.49), Medium (5.5-7.49), Severe (<5.49).

Figure 16A:
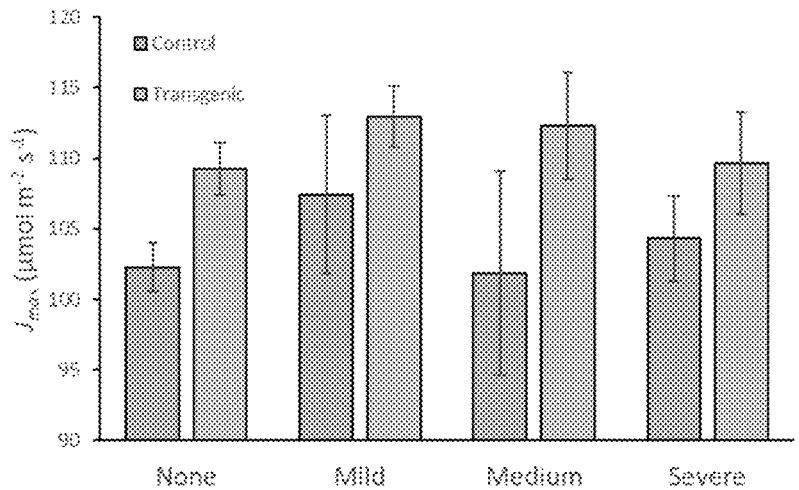
FIGS. 16A-B are graphs showing the $J_{max}$ (maximum rate of photosynthetic electron transport) under no, mild, medium, or severe drought stress (FIG. 16A) and the $A_{max}$ (maximum carbon assimilation rate) under no, mild, medium, or severe drought stress (FIG. 16B). $J_{max}$ and $A_{max}$ are indicators for photosynthetic activity in plants.
Figure 16B:
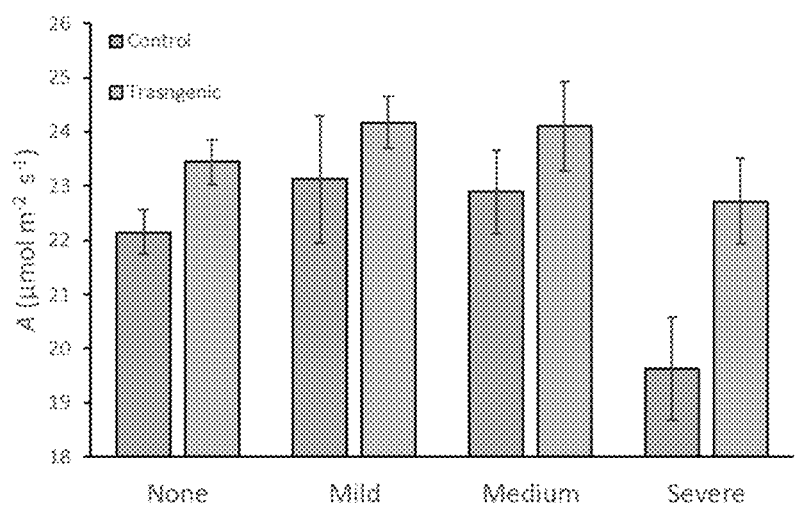

$J_{max}$ (maximum rate of photosynthetic electron transport) and $A_{max}$ (maximum carbon assimilation rate) are indicators for photosynthetic activity in plants. Higher values indicate higher activity. As shown in FIGS. 16A-B, under drought conditions, the transgenic trees were able to maintain higher level of photosynthetic activity. Even under the most severe drought conditions, $A_{max}$ in the transgenic plants was only slightly reduced, whereas it was drastically reduced in the non-transgenic plants.

Figure 17A:
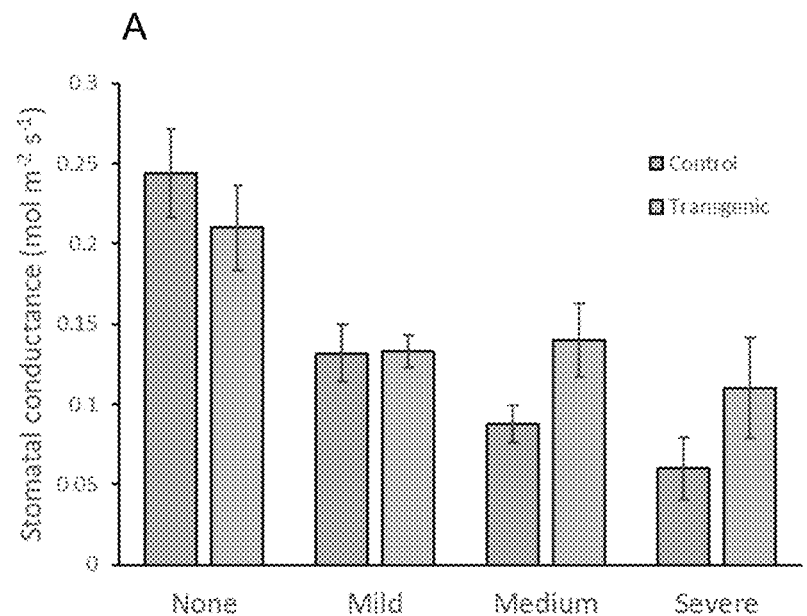
FIGS. 17A-B are graphs showing stomatal conductance under no, mild, medium, or severe drought stress (FIG. 17A) and water use efficiency (A/gsw; A, net carbon assimilation; gsw, stomatal conductance to water vapor) under no, mild, medium, or severe drought stress (FIG. 17B).
Figure 17B:
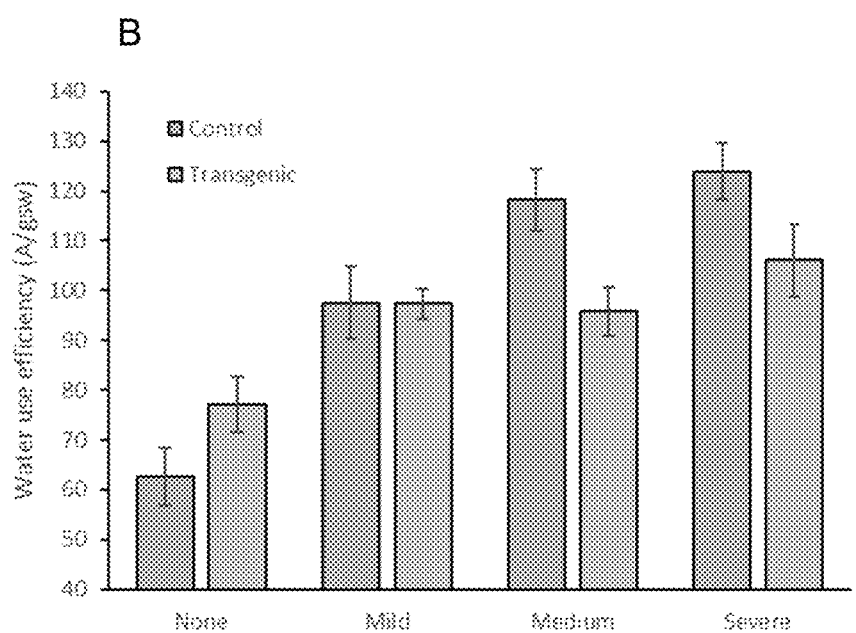

As shown in FIGS. 17A-B, the transgenic events showed higher stomatal conductance compared to non-transgenic controls under drought conditions. This was correlated with higher photosynthetic activity. On the contrary, non-transgenic plants showed a drastic reduction in stomatal conductance resulting from natural response to drought conditions when stoma in leaves are closing to reduce water loss due to transpiration, leading to artificially higher water use efficiency. Otherwise, the transgenic plants had higher water use efficiency as suggested by higher photosynthetic activity.

Example 12—Plgg1 in Other Species for RNAi & Other Exemplary Sequences

RNAi constructs for endogenous Plgg1 suppression in other tree species can be made in a similar fashion as described in the Examples above. SiFi or other software can be used to optimize sequence selection for use in the RNAi constructs. Examples of Plgg1 sequences from tree species are given in Table 9.

A full length coding sequence for *Pinus taeda* (Loblolly pine) (SEQ ID NO:35) (PITA_51316, which is hereby incorporated by reference in its entirety) is shown in Table 9. Exemplary Plgg1 RNAi polynucleotide fragments for use in *Pinus taeda* are shown below. A sense *Pinus taeda* Plgg1 fragment for use in RNAi (SEQ ID NO:36) is:

```
ATGGCTTCAT CCCACCAATT CCAAACTTCA TGGCTGCTCA CACGGAGACC GTTGGGAGAC

GCCTCTTTGC GTTTATATCA ATTACCCCGC AGGACCACAA AAGAGCAGAG GAAAAATTAT

GACAATTGCA GCTGTTGGGC GCAGAGGAGA AGAGAGGCAG CTGTCGCTGC AGCAATCAGA

ATTAATGGTG AGCGTAAGTT CATGTTCACG GGGTTTGGCA GGCAAAGGCC AAGGCGAAGT

CATGAAATAA TAATG
```

An antisense sense *Pinus taeda* Plgg1 fragment for use in RNAi (SEQ ID NO:37) is:

```
CATTATTATT TCATGACTTC GCCTTGGCCT TTGCCTGCCA AACCCCGTGA ACATGAACTT

ACGCTCACCA TTAATTCTGA TTGCTGCAGC GACAGCTGCC TCTCTTCTCC TCTGCGCCCA

ACAGCTGCAA TTGTCATAAT TTTTCCTCTG CTCTTTTGTG GTCGTGCGGG GTAATTGATA

TAAACGCAAA GAGGCGTCTC CCAACGGTCT CCGTGTGAGC AGCCATGAAG TTTGGAATTG

GTGGGATGAA GCCAT
```

Other exemplary Plgg1 sequences for use in methods disclosed herein include Plgg1 from *Populus alba* (SEQ ID NO:38) (GenBank Accession No. XM_035032358.1, which is hereby incorporated by reference in its entirety), *Populus tremula* (SEQ ID NO:39) (Potra000595g04516, which is hereby incorporated by reference in its entirety), *Populus euphratica* (SEQ ID NO:40) (GenBank Accession No. XM_011029786.1, which is hereby incorporated by reference in its entirety), and *Picea abies* (SEQ ID NO:41) (MA_92186g0010, which is hereby incorporated by reference in its entirety). SEQ ID NOs:38-41 are shown in Table 9.

Additional exemplary malate synthase and glycolate dehydrogenase sequences are shown in Table 9. These include *Populus trichocarpa* malate synthase (SEQ ID NO:42) (Potri.015G092000, which is hereby incorporated by reference in its entirety), *Populus tremula* malate synthase (SEQ ID NO:43) (Potra001425g12048, which is hereby incorporated by reference in its entirety), *Eucalyptus grandis* malate synthase coding sequence (SEQ ID NO:44) and protein sequence (SEQ ID NO:45) (GenBank Accession No. XM_010039145, which is hereby incorporated by reference in its entirety), *Chlamydomonas reinhardtii* glycolate dehydrogenase coding sequence (SEQ ID NO:46) and protein sequence (SEQ ID NO:47) (GenBank Accession No. DQ647436, which is hereby incorporated by reference in its entirety), and *Volvox carteri f. nagariensis* glycolate dehydrogenase coding sequence (SEQ ID NO:48) and protein sequence (SEQ ID NO:49) (GenBank Accession No. XM_002946413, which is hereby incorporated by reference in its entirety).

TABLE 9

Plgg1 Sequences & Other Exemplary Sequences

| Source | SEQ ID NO: | SEQUENCE (5' to 3') |
|---|---|---|
| *Pinus taeda* Plgg1 (PITA_51316) | 35 | ATGGCTTCAT CCCACCAATT CCAAACTTCA TGGCTGCTCA CACGGAGACC GTTGGGAGAC GCCTCTTTGC GTTTATATCA ATTACCCCGC AGGACCACAA AAGAGCAGAG GAAAAATTAT GACAATTGCA GCTGTTGGGC GCAGAGGAGA AGAGAGGCAG CTGTCGCTGC AGCAATCAGA ATTAATGGTG AGCGTAAGTT CATGTTCACG GGGTTTGGCA GGCAAAGGCC AAGGCGAAGT CATGAAATAA TAATGGTGAA AGCCTTTGAA AAGGATGCCA GAGGCCTCCC GGATGGCTCC CTCAAGGTGG GTCGTGTGGC GCATTTGGTG GTTTCGTTGG GCATAATTCT GGCCATCGAC AAGGCCTTGA AAAGGCTCTT CACGGCTGCC ATGATAAAGT TCCCTAGCGC ATTGTTTGGA ATGTTCTGCA TATTTTCCGT GCTGTCAATC CTCGACGTCA TCAGACCGGC AGCGGCAACG GCTCTACTGA ACTTTTTTGA GCCGGCAACA ACGTTCATAC AGAGATGGCT TCCGCTCTTC TACGTGCCGT CGCTGGTAGT GTTGCCTTA GCTGTGAAGG GAATCCCTGC TTCTTCCGGA ATGAAGATTG GCGCAATTCT TGTTGGAGGC TGGGCAGCAT CACTCTATGT TGCAGGGTAC ACAGCCATTG CCGTAAGAAA GATGGTCAGA ACAAAAATGA TAGCAGCAGA GCCCATGCCA AAGCCTTCTC CGTTTTCAAC AATAGAGATT TGGTTCTGGA CTATTATCTT GTCAGTTTCA TTTATATTGA CTGTTCTTTC ACCTCTTGCA TTTGGAACTT ATGCTCGAAC ATGCCTTCCG TGTCTTTTAG CGGCAACTGC GTTAGGATTC ATCCTTGGAT CTGGATTTCC ACCTACTGCC AAGAAGCTAC TACATCCAAT TATTACTTGT GCCCTATCTG CGGATTTGGC AGCCTTTGCT TGTGGGATCT CCACAGGATT GGGCTTTGAA TCCACGCTAG GGGCCTATTT AACTAAAAGT GCAACCAATC CTGGTGCTGG TGATATCTTG ATGGGATTTC TTGGATCTGT GATTCTTTCA TTCGCTTTCT CAATGTTCCG TCAGAGAAAG CTTGTCAAAC GGCATGCTGC GGAGATCTTC TCAGCTGTGG TGGTTTCAAC AATTTTTTCT CTGTACTCAA CAGCAGCTAT GGGCCGAATG ATTGGACTGG AACCAACCTT AACTGTTTCA ATTTTGCCAA GATGTATTAC TGTTGCACTA GCATTGAGCA TTTGTCTCGCT TTTTGATGGG CAATATAACT CTCGGGCGGA TTGTCCTTCA GGGTCTAGGG ATGAAAGAAA ATGA |
| *Populus alba* Plgg1 (XM_035032358.1) | 38 | ATGGC TACTCCTTTA GTCGCTCTTT CCGTTCAACT CTGTCATCAC CACTCAAAAC AATATTCTTT CAAATCACAA TCACAATCAC GTGTCAATAG GGATTTCCGT ACAAAAACAC TACTTGGTGT TTACAATGGA TTCCAAAATG TATATAACCA ATCTTATTTT CATAAGCCTT GGGCACCCAT TAGAGTTCTT GAGCCTAATT CAAGGTTCTT GCAAATGGGT CCTCAAGAAA CCTGCTCTAG TCGAGGAATT TCCAAGAAAT CTATGAGCTC AGAAGGCAGT ACCAGTACTA GCTCTTCATC TATTTCTCAA CAGGTGATTG GATCTTGCA TTTGCTTGTT TCACTTGGGA TTATCCTTGC AATGGATAAG TTGTTGAAAA AGGCATTTGT GGCTGCTGCT ATCAAGTTTC CAAGTGCTCT GTTTGGCATG TTCTGCATAT TCTCAGTTTT AGTGATTCTT GATATAACTA TTCCGGCTGC TGCAACAAGC TTAATGAACT TCTTTGAGCC AGCACTGTTA TTCATTCAGA GATGGCTTCC GTTGTTCTAC GTTCCATCAT TGGTTGTTTT GCCTCTCTCT GTTAAAGATA TCCCTGCTGC ATCAGGTGTC AAGATTTGCT TCATCACAGC TGGAGGGTGG CTGCCGTCAC TTTGTGTGGC GGGTTTCACA GCTATTGCTG TGAGAAAAAT GGTGAAGACA GAAATGACTG ACGCTGAGCC TATGGCGAAA CCCTCTCCTT TTTCTCCATT GGAAATGTGG GCTTGGAGTG GGGTCTTCCT TGTATCATTT GTTGTCGCAT TATTATATAG AACGGCATTG GGGACTGCAG CCAGAACATG CCTTCCTTTC CTACTAGCGT CCACCGTGCT AGGCTATATG GTTGGTTCTG GGTTACCATC TGGTGTTAAG AAGGTTTTCC ATCCCATTAT TTGTTGTGCA CTATCTGCAG ATTTGGCAGC GTTGGCCTTT GGGTACCTTT CCCAATCTGG ACTTGATCCC GTTCTAGGAT ATTACCTTAC AAAAGTTTCA TCTAATCCTG GAGCTGGTGA TGTGTTAATG GGATTCTTGG GACCTGTCAT TCTTTCTTTT GCCTTCTCAA TGTTCAAGCA GCGAAAGCTT GTTAAGAGAC ATGCAGCTGA GATTTTCACG TCGGTCATTG TTTCAACACT ATTTTCATTG TATTCAACGG CTCTCGTGGG ACGTCTAGTT GGGTTAGAAC CAACGTTGAC TGTATCCATT ATTCCCAGAT GTATAACCGT GGCATTAGCC CTCAGCATTG TGTCATTCTT TGAAGGTGCC AATTCATCTC |

TABLE 9-continued

Plgg1 Sequences & Other Exemplary Sequences

| Source | SEQ ID NO: | SEQUENCE (5' to 3') |
|---|---|---|
| | | TCACAGCTGC TGTAGTTGTT GTAACTGGTC TCATTGGAGC AAATTTTGTA CAAGCAGTGC TTGATAAATT AAGTTTTCGT GATCCCATTG CTCGAGGAAT AGCTACTGCT TCCAGTGCTC ATGGACTGGG AACTGCAGCA TTGTCAGCCA AGGAACCTGA GGCACTTCCA TTTTGTGCCA TTGCTTATGC TCTCACTGGT ATATTTGGTT CATTGTTTTG TTCAGTTCCT GCAGTTAGGC AAAGCTTACT TGCAATAATT GGCTGA |
| Populus tremula Plgg1 (Potra 000595g04516) | 39 | ATGGCTACTC CTTTAGTCGC TCTTTCCGTT CAACTCTGTC ATCACCACTC AAAACAATAT TCTTTCAAAT CACAATCACG TGTCAATAGG GATTTCCGTA CGAAAACACT ACTTGGTGTT TACAATGGAT TCCAAAATGT ATATAACCAA TCTTATTTTC ATAAGCCTTG GGCACCCATT AGAGTTCTTG AGCCTAATTC AAGGTTCTTG CAAATGGGTC CTCAAGAAAC CTGCTCTAGT CGAGGAATTT CCAAGAAATC TATGAGCTCA GAAGGCAGTA CCAGTACTAG CTCTTCATCT ATTTCTCAAC AGGTGATTGG GATCTTGCAT TTGCTTGTTT CACTTGGGAT TATCCTTGCA ATGGATAAGT TGTTGAAAAA GGCATTGTG GCTGCTGCTA TCAAGTTTCC AAGTGCTCTG TTTGGCATGT TCTGCATATT CTCGGTTTTA GTGATTCTTG ATATAACTAT TCCGGCTGCT GCAACAAGCT TAATGAACTT CTTTGAGCCA GCACTGTTAT TCATTCAGAG ATGGCTTCCG TTGTTCTACG TTCCATCATT GGTTGTTTTG CCTCTCTCTG TTAAAGATAT CCCTGCTGCA TCAGGTGTCA AGATCTGCTT CATCACAGCT GGAGGGTGGC TGGCGTCACT TTGCGTGGCG GGTTTCACAG CTATTGCTGT GAGAAAATTG GTGAAGACAG AAATGACTGA CGCTGAGCCT ATGGCGAAAC CCTCTCCTTT TTCTCCATTG GAAATGTGGG CTTGGAGTGG GGTCTTCCTT GTATCATTTG TTGTCGCATT ATTATATAGA ACGGCATTGG GGACTGCAGC CAGAACATGC CTTCCTTTCC TACTAGCGTC CACCGTGCTA GGCTATATGG TTGGTTCTGG GTTACCATCT GGTGTTAAGA AGGTTTTCCA TCCCATTATT GCTGTGCAC TATCTGCAGA TTTGGCAGCG TTGGCCTTTG GGTACCTTTC CCAATCTGGA CTTGATCCCG TTCTAGGATA TTACCTTACA AAAGTTTCAT CTAATCCTGG AGCTGGTGAT GTGTTAATGG GATTCTTGGG ACCTGTCATT CTTTCTTTTG CCTTCTCAAT GTTCAAGCAG CGAAAGCTTG TTAAGAGACA TGCAGCTGAG ATTTTCACGT CGGTCATTGT TTCAACACTA TTTTCATTGT ATTCAACGGC TCTCGTGGGA CGTCTAGTTG GGTTAGAACC AACGTTGACT GTATCCATTA TTCCCAGATG TATAACCGTG GCATTAGCCC TCAGCATTGT GTCATTCTTT GAAGGTGCCA ATTCATCTCT CACAGCTGCT GTAGTTGTTG TAACTGGTCT CATTGGAGCA AATTTTGTAC AAGCAGTGCT CGATAAATTA AATTTTCGTG ATCCCATTGC TCGAGGAATA GCAACTGCTT CCAGTGCTCA TGGACTGGGA ACTGCAGCAT TGTCAGCCAA GGAACCTGAG GCACTTCCAT TTTGTGCCAT TGCTTATGCT CTCACTGGTA TATTTGGTTC ATTGTTTTGT TCAGTTCCTG CAGTTAGGCA AGCTTACTT GCAATAATTG GCTGA |
| Populus euphratica Plgg1 (XM 011029786.1) | 40 | ATGGCTACTC CTTTAGTCGC TCATTCCGTT CTACTCTGTC ATCACCACTC AAAACAATAT CCTTTCAAAT CGCAATCACG TGTCGATAGG GATTTCCGTA CGAAAACACT ACTTGGTGTT TACAATGGAT TCCAAAATGT ATATAACCAA TCTTATTTTC ATAAGCCTTG GGCACCCATT AGAGTTCTTG AGCCTAATTT AAGGTTCTTG CAAATGGGTC CTCAAGAAAC CTGCTCTAGT CGACGAATTT CCAAGAAATC TATGAGCTCA GAAGGCAGTA CCAGTAGTAC TAGCTCTTCA TCTATTTCTC AACAGGTGAT TGGGATCTTG CATTTGCTTG TTTCACTTGG GATTATCCTT GCAATGGATA AGTTGTTGAA AAAGGCATTT GTGGCTGCTG CTATTAAGTT TCCAAGTGCT CTATTTGGCA TGTTCTGCAT ATTCTCAGTT TTAGTCATTC TTGATATAAC TATTCCGGCT GCTGCAACAA GCTTAATGAA CTTCTTTGAG CCAGCACTGT TATTCATTCA GAGATGGCTT CCATTGTTCT ACGTTCCATC ATTGGTTGTT TGCCTCTCT CTATTAAAGA TATCCCTGCT GCATCAGGTG TCAAGATTTG CTTCATCACA GCTGGAGGGT GGTTGGCGTC ACTTTGTGTG GCGGGTTTTA CAGCTATTGC TGTGAGAAAA ATGGTGAAGA CAGAAATGAC TGATGCTGAG CCTATGGCGA AACCCTCTCC TTTTCTCCA TTGGAAATGT GGGCTTGGAG TGGGGTCTTC CTTGTATCAT TTGTTGTCGC CTTATTATAT AGAACGGCAT TGGGGACTGC AGCCAGAACA TGCCTTCCTT TCCTACTAGC ATCCACCGTG CTAGGCTATA TGGTTGGTTC TGGGTTACCA TCTGGTGTTA GAAGGTTTT CCATCCCATT ATTTGTTGTG CACTATCTGC AGATTTGGCA GCGTTGGCCT TTGGGTTCCT TTCCAATCC GGACTTGATC CCGTTCTAGG ATATTACCTT ACAAAAGTTT CATCCAATCC |

TABLE 9-continued

Plqq1 Sequences & Other Exemplary Sequences

| Source | SEQ ID NO: | SEQUENCE (5' to 3') |
|---|---|---|
| | | TGGAGCTGGT GATGTGTTAA TGGGATTCTT GGGATCTGTC ATTCTTTCTT TTGCTTTCTC AATGTTCAAG CAGAGAAAGC TTGTTAAGAG ACATGCAGCT GAGATTTTCA CGTCAGTCAT TGTTTCAACA CTATTTTCAT TGTATTCAAC GGCTCTCGTG GGACGCCTAG TTGAGTTAGA ACCAACATTG ACTGTATCCA TTATTCCCAG ATGTATAACC GTGGCATTAG CCCTCAGCAT TGTGTCATTC TTTGAAGGTG CCAATTCATC TCTCACAGCT GCTGTAGTTG TTGTAACTGG TCTCATTGGA GCAAATTTTG TACAAGCAGT GCTCGATAAA TTAAATTTTC TTGATCCCAT TGCTCGAGGA ATAGCAACTG CTTCCAGTGC TCATGGACTG GGAACTGCAG CATTGTCAGC CAAGGAACCT GAGGCACTTC CATTTTGTGC CATTGCTTAT GCTCTCACTG GTATATTTGG TTCATTGTTT TGTTCAGTTC CTGCAGTTAG GCAAAGCTTA CTTGCAATAA TTGGCTGA |
| Picea abies Plqq1 (MA_92186g0010) | 41 | ATGGCCCTGG AAGTTAAACC TGCTAAAAAT AGTAAATTGC CAAAATTGCC AGAAAACTAT TTTGAGCCAG TCGGAAAAGG TGGGTGGCCA CTGATATCCT CTTGGATCAA ACGGCATGCT GCAGAGATCT TCTCAGCTGT GGTGGCTTCA ACAATTTTTT CTCTGTACTC AACAACAGTT GTAGGTCGAA TGATTGGAAT GGAACCAACC TTAACTGTTT GCATTTTGCC AAGATGTATT ACTGTTGCAT TAGCACTGAG CATTGTCTCA CTTTTTGATG CTGCAAATCC TTCCCTTACA GTAGCTGTCA TGGTTTTAAC GGGATTGGTT GGGGAAAATT TTGCACAAAT ATTTCTCGAA AAGCTTGGTT TGGATGATTC TATTGCACGA GGAATGGCTA TAGCCTTCAG TGCTCATGGA TTGGGAACGA CAGCATTGTC AGCAAAAGAA CCAGAAGCAT TGCCTTTCTG TGCAATTTCC TATGCATTAA CTGCGGAGGC CATGGCTGGA GATGGTGGAT CGGAGCGCCT TGACGAAGCG GGAGTCGCTG GGTTAGGCGA GCAACAAGAT CTGCAAGAAT TGTACATATT TCCACATCGA TTACCTATTG CTGCTCTGAC GGAGCCTCTC GTCCTACTCA ACAGGACCTA CAGCAACAGG GAGGTTCTCG GGATCATGAC GGTGCTAACC ATTGTTATCG TGTTTCTCAC GAGCATTGGG TCGTTACTCA TCTCGGTGCT TATGGTCGGA TTGGGTATCG TTTGTGTCCA TGGTGCATTT AGGGTTTCCG AAGATCTGTT TTTGGACGAG CAGGAGCAGG CGGTCAGATT CTTGTCCTTC CTCGGTGGCG GTGGATCCCA TCCCCCTGTT GCTATCCATG TTTGA |
| Populus trichocarpa Malate Synthase (Potri.015G092000) | 42 | GAAACACTCT CATACACGTT AAAAACCATA CAACAAAGAA GAGTGGCATT GCTTAAAAAA CAGTCAGATC AATAATGGGA CCTGCAACTT ATGAGAATCA CTATCCACCG CCCAATATGA AGAAGTTTGG CTATGATGCT CCTGAAGGAG TTGAAATTAG AGGCAGATAT GACGGAGAGT TTGCAGTGAT CCTTACCAAG GATGCTTTGC AATTTGTTGC TGATTTGCAG AGAGAGTTTA GGAACCGCAT CAAGTATGCA ATGGAGTGTC GCAAGGAAGC CAAAAGGAGG TACAGTGAGG GGGCTTTACC AGGGTTTGAT CCAGCTACAA GGTACATAAG GGAGGGGGAG TGGACATGTG CACCTGTCCC TCCAGCTGTT GCTGATAGGA AGGTGGAGAT TACAGGTCCA GTGGAGAGGA AAATGATCAT CAATGCACTC AATTCTGGAG CTAAAGTTTT CATGGCTGAC TTTGAAGATG CACTGTCACC AAGTTGGGAG AACCTTATGA GAGGACAAGT TAACCTGAAG GACGCTGTCG CTGGGACTAT TACCTTTCAC GACAAGGTCA GGAACAGGGT TTATAAGCTG AATAACCAGA CAGCCAAGTT GTTTGTCCGC CCACGAGGTT GGCATCTACC TGAGGCGCAC ATTCTCATTG ATGGAGAACC AGCAACTGGT TGCCTTGTGG ACTTTGGCCT TTACTTTTAC CACAACTATG CAGCATTCCG TCGGATTCAG GGTGCAGGGT TCGGGCCTTT CTTCTATCTC CCTAAGATGG AGAATTCAAG GGAGGCTAAG ATATGGAACT GTGTGTTCGA GAAAGCAGAG AAGATGGCAG GAATTGAAAG GGGAAGCATC AGGGCCACTG TCCTAATCGA AACACTTCCA GCTGTTTTCC AAATGAATGA AATCCTCTAC GAACTAAGGG ATCACTCTGT TGGCTTGAAC TGCGGAAGAT GGGATTACAT CTTCAGCTAT GTCAAGCAT TCCAGGCTCA CCCAGATCGC CTGCTACCAG ACAGGGTTCA AGTTGGCATG ACTCAGCACT TCATGAAGAG TTACTCTGAT CTCCTCATCT GGACATGCCA TAGGCGTGGT GTCCATGCGA TGGGCGGCAT GGCAGCTCAG ATTCCAATCA GAGACGATCC AGAGGCGAAT AATGAAGGAC TAGAACTCGT GCGAAAGGAC AAGCTAAGAG AGGTTCGAGC AGGACATGAT GGAACATGGG CAGCCCACCC TGGACTTATC CCAGCTTGCA TGGAAGTCTT CTCAAACAAC ATGGGAAACA CGCCAAACCA AATCCAGTCC ATGAAGCGCG AAGATGCATC AACCATTACA GAGGAAGACC TCTTACAGAG GCCAAGAGGG TCCCGTTCGT TGGAAGGTCT CCGCCTAAAC ACCCGTGTAG GAATCCAGTA CTTAGCAGCA TGGCTAACTG |

TABLE 9-continued

Plqq1 Sequences & Other Exemplary Sequences

| Source | SEQ ID NO: | SEQUENCE (5' to 3') |
|---|---|---|
| | | GAACTGGCTC AGTCCCTCTT TACAACCTCA TGGAAGACGC TGCCACTGCA GAAATCAGCA GAGTTCAGAA CTGGCAATGG CTTAAATATG GAGTGGAACT TGACGGAGAT GGCCTTGGAG TGAAAGTTAA CAATGATCTG TTCGGGAAAG TGGTGGAAGA GGAAATGGCT AGGATTGAAA GGGAAGTTGG GAAAGAGAAA TTCAAGAGGG GAATGTACAA GGAGGCCTGC AAGATTTTCG CAAGGCAATG CACAGCACCT ACACTGGATG ATTTTCTTAC CCTGAATGCT TATGATAATA TCGTCATCCA TCACCCTATG GGATCATCAT CCCGCCTCTA AGTCATGAGT TTCATCGCTT GTTTTTAATT TCCTGGGATT GATGTGTGCC CTCGTGTTCT ACTCTACTAC TACAACTTGA ATAAAATCCT TTCTATCTGT TTGAACTTAA GTTCCACCCA TTA |
| Populus tremula Malate Synthase (Potra 001425g12048) | 43 | GTTTAATCAA ATCTTACGCA CATAAAGCCA TAACGATAAT GCTCCTTGTA CCTATCCACT TGCCTCCACT CTCCCTTTAT ATATTTCTAC TCTTGAGCTT ACCCTTGAAA CACTCTCATA CACGTTAAAA ACCATACAGT AAAGAAGAAT CGCGTTGCTA AAAAAACAGT GAGATCAATA ATGAGACCTG CAACTAATGG GAATCCGGAT GCACCGCCCG ATATGAAGAA GTTTGGCTAT GATTCTCCTG AAGGAGTTGA AGTTAGAGGC AGATATGACG GCGAGTTTGC AGTGATCCTT ACCAAGGATG CTTTGCAATT TGTTGCTGAT TTGCAGAGAG AGTTTAGGAA CCGCATCAAG TATGCAATGG AGTGTCGCAA GGAAGCCAAA AGGAGGTACA GTGAGGGGGC TCTACCAGGG TTTGATCCAG CTACAAGGTG CATAAGGGAG GAGGAGTGGA CATGTGCACC TGCCCCTCCA GCTGTTGATG ATAGGAAGGT GGAGATTACA GGTCCAGTGG AGAGGAAAAT GATCATCAAT GCCCTCAATT CTGGAGCGAA AGTTTTCATG GCTGACTTTG AAGATGCGCT CTCACCAAGC TGGGAGAACC TTATGAGAGG ACAAGTTAAC CTGAAGGATG CTGTTGATGG GACTATTACC TTTCACGACA AGGTCAGGAA CAGGGTTTAT AAGCTGAATA ATCAGACAGC CAAGTTGTTT GTCCGCCCAC GAGGTTGGCA TCTACCTGAG GCGCACATTC TCATTGATGG AGAACCTGCA ACTGGTTGCC TTGTGGACTT TGGCCTTTAC TTTTACCACA ACCATGCAGC ATTCCGTCGG AATCAGGGTG CAGGGTTCGG GCCTTTCTTC TATCTCCCTA AGATGGAGAA TTCAAGGGAG GCTAAGATAT GGAACTGTGT GTTTGAGAAA GCAGAGAAGG TGGCAGGAAT TGAAAGGGGA AGCATCAGGG CCACTGTCCT TATCGAAACA CTTCCAGCTG TCTTCCAAAT GAATGAAATC CTCCACGAAC TAAGGGATCA CTCTGTTGGG TTGAACTGCG GAAGATGGGA TTACATCTTC AGCTATGTCA AGACATTCCA GGCTCACCCA GATCGCCTGC TACCAGACAG AGTTCAAGTT GGCATGACTC AGCACTTCAC GAAGAGCTAC TCCGATCTCC TCATCTGGAC ATGCCATAGG CGTGGTGTGC ACGCGATGGG CGGCATGGCA GCTCAGATTC CTATCAGAGA CGATCCAGAG GCGAATAAGG AAGCACTGGA GCTCGTGCGA AAGGACAAGC TAAGAGAGGT TCGAGCAGGA CATGACGGAA CATGGGCAGC CCACCCTGGA CTTATCCCAG CTTGCATGGA AGTCTTCTCA GACAACATGG GAAACACGCC AAACCAGATC CAAACCATGA AGCGCGAAGA TGCATCAACC ATAACAGAGG AAGACCTCTT ACAGAGACCA AGAGGGTCCC GTTCATTGGA AGGTCTCCGC CTAAACACCC GTGTGGGAAT CCAGTACCTA GCAGCATGGC TAACTGGAAC TGGATCGGTC CCTCTTTACA ACCTCATGGA AGATGCCGCC ACCGCAGAAA TCAGCAGAGT TCAGAACTGG CAATGGCTTA AATATGGAGT GGAACTTGAC GGAGATGGCC TTGGAGTGAG AGTTAACAAT GATCTGTTCG GGAAAGTGGT GGAGGAGGAG ATGGCTAGGA TTGAAAGGGA GGTCGGGAAA GAGAAGTTCA AGAGGGGAAG GTACAAGGAG GCCTGCAAGA TTTTCGCAAG GCAATGCACA GCACCTACAC TAGATGATTT TCTTACACTG AATGCTTATG AAAATATCGT CAGCCATCAC CCTATGGGAT CATCACCCCG CCTCTAAGTC ACGAGTTTCA TCGCTTGTTT TTAATTTCCA GGGATTGATG TGTGCCCTCG TGTTCCACTC TACTACTACA AGTTATCTAC AACTTGAATA AAATCTTTTC TACCTGTTTG AACTTAAGTT CCACCCTTTA CTTGCACTTA TTTTATTT |
| Eucalyptus grandis Malate Synthase (XM_010039145) | 44 | ATGATGGAT CTCGGGTCGT TCACGTACCA AGCACCAGCA ACCAACAAGG CCAACCCCGC GTCCGGCTAC GACGTCCCCG AGGGAGTGGA CATCAGAGGG CGTTACGATG CCCAGTTCGC CAGGATCCTC NACCGGGACG CCTTGCAGTT CGTCGCCGAT CTGCAGAGGG AGTTCAGGGG CCACATCAAG TACGCCATGG AGTGTCGCCG CAACGCCAAG CAGCGCTACA ACGCCGGCGC GCTGCCTGGG TTCGACCCCG CTACGAGGTA CGTGAGGGAA GGCGAGTGGA CGTGCTCGCT GGTCCCACCA GCCGTGGCCG |

TABLE 9-continued

Plqq1 Sequences & Other Exemplary Sequences

| Source | SEQ ID NO: | SEQUENCE (5' to 3') |
|---|---|---|
| | | ACCGGAGGGT GGAGATCACT GGCCCTGTCG AGCGCAAGAT GATCATCAAC GCGCTCAACT CTGGCGCCAA AGTTTTCATG GCAGATTTCG AAGATGCGCT ATCCCCGAGC TGGGAGAACC TGATGAGAGG GCAAGTGAAC CTGAAGGATG CGGTGGATGG GACCATAACC TTCCACGACA AGGCCCGAAA CAGGGTCTAC AAGCTCAATG ACCAGATTGC CAAGCTCTTT GTCCGGCCCC GAGGTTGGCA CTTGCCTGAG TCTCACATCC TCATTGACGG TGAGCCTGCA ACCGGTTGCC TCTTCGACTT TGGCCTCTAC TTCTTCCACA ACTACGCTTC ATTCAGGAAA ATGCAGGGTG AGGGGTTCGG GCCCTTCTTC TATCTCCCTA AGATGGAGCA TTCCAGGGAA GCGAAGATAT GGAACAGCGT CTTTGAGAGG GCAGAGAAAA TGGCGGGCAT CGAGAGAGGG AGCATAAGGG CAACGGTATT GATAGAGACA CTACCTGCAG TGTTCCAGAT GGATGAGATA CTGTACGAGC TGAGGGATCA CTCGGTCGGA TTGAACTGCG GAAGATGGGA CTACATCTTC AGCTATGTCA AGACCTTCCA GGCTCATCCC GATCGCCTAC TGCCTGACAG GTTTCAGGTC GGGATGACCC AGCACTTCAT GAGGTCTTAC TCTGATCTCC TCATCCGGAC TTGCCATCGG CGCGGTGTTC ATGCCATGGG AGGCATGGCG GCTCAAATCC CGATCAGAGA TGATCCGGTG GCCAATGAGG CGGCGCTGGA ACTAGTAAGG AAAGACAAGC TCAGAGAAGT CAGGGCCGGG CATGACGGGA CATGGGCTGC TCACCCGGGG TTAATCCCGG CTTGTATGGA AGTCTTCACG AATCACATGG GCAATGCGCC ACACCAGATC CAATCAGTCA AGAGAGAGGA CGCAGCCAAC ATAACCGAGG AAGACCTCCT CCAGAGGCCG AGAGGGGCCC GAACTTTGGA AGGCCTCCGG CTCAACACTC GGGTTGGGAT CCAATACCTG GCAGCCTGGC TCACAGGGAC AGGGTCGGTC CCACTCTACA ATCTCATGGA GGATGCGGCA ACTGCCGAGA TCAGCCGAGT CCAGAACTGG CAGTGGCTGA AGTATGGTGT GGAGCTGGAC GGTGATGGGG TTGGAGTGAG AGTGAGCTTG GATCTATTCG CGAGGGTGGT GGAGGAAGAG GTGGCCAGGA TTGAGNNAGA GGTTGGGAAG GACAAGTTCA AGAAGGGGAT GTACAAGGAG GCTGGCAAGA TGTTCACGAG ACAATGCACG GCGCCAGTGT TGGACGATTT CCTGACGCTC GATGCCTACA ATCACATCGT CGTGCATCAT CCTAGGGGGT CTTCCAAGCT CTGA |
| Eucalyptus grandis Malate Synthase (XM_010039145) | 45 | MMDLGSFTYQ APATNKANPA SGYDVPEGVD IRGRYDAQFA RILRDALQFV ADLQREFRGH IKYAMECRRN AKQRYNAGAL PGFDPATRYV REGEWTCSLV PPAVADRRVE ITGPVERKMI INALNSGAKV FMADFEDALS PSWENLMRGQ VNLKDAVDGT ITFHDKARNR VYKLNDQIAK LFVRPRGWHL PESHILIDGE PATGCLFDFG LYFFHNYASF RKMQGEGFGP FFYLPKMEHS REAKIWNSVF ERAEKMAGIE RGSIRATVLI ETLPAVFQMD EILYELRDHS VGLNCGRWDY IFSYVKTFQA HPDRLLPDRF QVGMTQHFMR SYSDLLIRTC HRRGVHAMGG MAAQIPIRDD PVANEAALEL VRKDKLREVR AGHDGTWAAH PGLIPACMEV FTNHMGNAPH QIQSVKREDA ANITEEDLLQ RPRGARTLEG LRLNTRVGIQ YLAAWLTGTG SVPLYNLMED AATAEISRVQ NWQWLKYGVE LDGDGVGVRV SLDLFARVVE EEVARIEEVG KDKFKKGMYK EAGKMFTRQC TAPVLDDFLT LDAYNHIVVH HPRGSSKL |
| Chlamydomonas reinhardtii Glycolate dehydrogenase (DQ647436) | 46 | ATGCCACGCG GCCAGGGCAA GCGCCTGGCT CAGCTCCTTG GAGCTCAGCT GAAGCAGTAC GCAGCGGAGG TGCGTGGCAT CAGCACAGCT GGTGGCGCTT CTCGCGGTGG AGCTCGAGGA CCTGCATCCC CTAGCTCGCT AGAGCAGCAG ACGCGCCAGG TCGCTCAGGT TGCTGTTCAG CAGTCGACTC AGCAGGCAGT GAAGGTCGTT GTGCCGGCCA TCAAAGTAGA CCTGGTTGGT GCGGTCAGCT CGGTGTCTGA GAGCGACAAG GTGGAGCCGG GTGTGTTCAA GAACGTGGAT GGCCACCGCT TCGAGGACGG TCGCTATGCC GCTTTTGTTG AGGAGATTAC AAAGTTTATC CCCAAGGAGC GCCAGTACTC GGACCCCGTG CGCACATTCG CGTATGGCAC GGATGCCTCC TTCTACCGGC TTAACCCGAA GCTGGTAGTG AAGGTGCACA AGGAGGACGG GGTCCGCCGC ATCATGCCCA TCGCGGAGCG GCTGCAGGTC CCTATCACCT TCCGCGCGGC CGGCACGTCG CTGTCTGGGC AGGCAATTAC CGACTCGGTG CTCATTAAGC TGAGCCACAC GGGCAAGAAC TTCGCAACT TACCGTGCA CGGCGACGGT AGCGTGATCA CGGTGGAGCC GGGCCTCATT GGCGGCGAGG TGAACCGCAT CCTGGCGGCA CACCAGAAGA AGAACAAGCT GCCCATCCAG TACAAGATCG ACCCGACCC TCCTCCATC GACAGCTGCA TGATCGGCGG CATCGTGTCC AACAACAGCA GCGGCATGTG TTGCGGCGTG AGCCAGAACA CCTACCACAC GCTGAAGGAC ATGCGGGTGG TGTTCGTAGA CGGAACGGTG CTGGACACGG CCGACCCCAA CTCGTGCACC GCCTTCATGA GAGCCACCG |

TABLE 9-continued

Plqq1 Sequences & Other Exemplary Sequences

| Source | SEQ ID NO: | SEQUENCE (5' to 3') |
|---|---|---|
| | | CTCGCTGGTG GATGGCGTCG TGAGCCTGGC GCGCCGCGTG<br>CAGGCCGACA AGGAGCTGAC GGCGCTCATC CGCCGCAAGT<br>TCGCCATCAA GTGCACCACC GGCTACTCCC TGAACGCGCT<br>GGTGGACTTC CCGGTGGACA ACCCCATTGA GATCATCAAG<br>CACCTCATCA TCGGCAGCGA GGGCACGCTG GGCTTCGTCA<br>GCCGCGCCAC CTACAACACC GTGCCCGAGT GGCCCAACAA<br>GGCCTCGGCC TTCATCGTGT TCCCGGACGT GCGCGCCGCC<br>TGCACCGGCG CCTCGGTGCT GCGCAACGAG ACGTCCGTGG<br>ACGCGGTGGA GCTGTTTGAC CGCGCCAGCC TGCGCGAGTG<br>CGAGAACAAC GAGGACATGA TGCGCCTGGT GCCCGACATC<br>AAGGGCTGCG ACCCCATGGC GGCAGCGCTG CTGATCGAGT<br>GCCGCGGCCA GGACGAGGCC GCACTGCAGA GCCGCATTGA<br>GGAGGTGGTG CGCGTGCTGA CGGCGGCGGG CCTGCCCTTC<br>GGCGCCAAGG CCGCGCAGCC CATGGCCATC GACGCCTACC<br>CCTTCCACCA CGACCAGAAG AACGCCAAGG TCTTCTGGGA<br>CGTGCGCAGG GGCCTGATCC CCATTGTGGG CGCGGCGCGC<br>GAGCCCGGCA CATCCATGCT GATCGAGGAC GTGGCCTGCC<br>CCGTGGACAA GCTGGCCGAC ATGATGATCG ACCTGATCGA<br>CATGTTCCAG CGCCACGGCT ACCACGACGC CTCCTGCATC<br>GGCCACGCGC TCGAGGGCAA CCTTCACTTG GTGTTCTCGC<br>AGGGCTTCCG CAACAAGGAG GAGGTGCAGC GCTTCAGCGA<br>CATGATGGAG GAGATGTGCC ACCTGGTGGC CACCAAGCAC<br>TCGGGCAGCC TCAAGGGCGA GCACGGCACG GGCCGCAACG<br>TGGCGCCGTT CGTGGAGATG GAGTGGGGCA ACAAGGCGTA<br>CGAGCTGATG TGGGAGCTCA AGGCGCTGTT CGACCCCAGC<br>CACACCCTCA ACCCGGGCGT CATCCTCAAC CGCGATCAGG<br>ACGCGCACAT CAAGTTCCTG AAGCCCTCGC CCGCGGCCTC<br>GCCCATCGTC AACCGCTGCA TCGAGTGCGG CTTTTGCGAG<br>TCCAACTGCC CCTCGCGCGA CATCACGCTC ACGCCGCGCC<br>AGCGCATCTC CGTGTACCGC GAGATGTACC GCCTCAAGCA<br>GCTGGGCCCG GGCGCCAGCC AGGAGGAGAA GAAGCAGCTG<br>GCGGCCATGA GCAGCTCGTA CGCCTACGAC GGCGAGCAGA<br>CGTGCGCGGC GGACGGCATG TGCCAGGAGA AGTGCCCCGT<br>CAAGATCAAC ACGGGAGACC TGATCAAGTC GATGCGTGCC<br>GAGCACATGA AGGAGGAGAA GACCGCCAGC GGCATGGCAG<br>ACTGGCTGGC CGCCAACTTC GGCGTCATCA ACTCCAACGT<br>GCCGCGCTTC CTCAACATCG TCAACGCCAT GTACAGCGTG<br>GTGGGCTCGG CGCCTCTGTC CGCGATCAGG CGCGCGCTCA<br>ACGCCGCCAC CAACCACTTC GTGCCGGTGT GGAACCCCTA<br>CATGCCCAAG GGCGCGGCGC CGCTCAAGGT GCCCGCCCCG<br>CCGGCGCCGG CAGCTGCTGA GGCCTCGGGC ATCCCGCGCA<br>AGGTGGTGTA CATGTCCAGC TGCGTGACGC GCATGATGGG<br>CCCCGCCGCC TCCGACACCG AGACGGCGGC GGTGCACGAG<br>AAGGTGATGA GCCTGTTCGG CAAGGCCGGC TACGAGGTGA<br>TCATCCCCGA GGGCGTGGCC AGCCAGTGCT GCGGCATGAT<br>GTTCAACAGC CGCGGCTTCA AGGACGCCGC CGCCAGCAAG<br>GGCGCGGAGC TGGAGGCGGC GCTGCTCAAG GCCTCGGACA<br>ATGGCAAGAT GCCCATCGTC ATCGACACCT CGCCCTGCCT<br>GGCGCAGGTG AAGAGCCAGA TCAGCGAGCC GTCGCTGCGC<br>TTCGCGCTGT ACGAGCCGGT TGAGTTCATC CGGCACTTCC<br>TGGTGGACAA GCTGGAGTGG AAGAAGGTGC GCGACCAGGT<br>GGCCATCCAC GTGCCCTGCT CCTCCAAGAA GATGGGCATC<br>GAGGAGTCCT TCGCGAAGCT GGCGGGCCTG TGCGCCAACG<br>AGGTGGTGCC CTCGGGCATT CCTTGCTGCG GCATGGCGGG<br>CGACCGCGGC ATGCGCTTCC CCGAGCTGAC CGGCGCCTCG<br>CTGCAGCACC TCAACCTGCC CAAGACCTGC AAGGACGGCT<br>ACTCCACCAG CCGCACCTGC GAGATGTCGC TCAGCAACCA<br>CGCCGGCATC AACTTCAGGG GCCTGGTGTA CCTGGTGGAT<br>GAGGCCACGG CGCCTAAGAA GCAGGCCGCC GCTGCCAAGA<br>CCGCGTAA |
| Chlamy-<br>domonas<br>reinhardtii<br>Glycolate<br>dehydrogenase<br>(DQ647436) | 47 | MPRGQGKRLA QLLGAQLKQY AAEVRGISTA GGASRGGARG<br>PASPSSLEQQ TRQVAQVAVQ QSTQQAVKVV VPAIKVDLVG<br>AVSSVSESDK VEPGVFKNVD GHRFEDGRYA AFVEEITKFI<br>PKERQYSDPV RTFAYGTDAS FYRLNPKLVV KVHNEDEVRR<br>IMPIAERLQV PITFRAAGTS LSGQAITDSV LIKLSHTGKN<br>FRNFTVHGDG SVITVEPGLI GGEVNRILAA HQKKNKLPIQ<br>YKIGPDPSSI DSCMIGGIVS NNSSGMCCGV SQNTYHTLKD<br>MRVVFVDGTV LDTADPNSCT AFMKSHRSLV DGVVSLARRV<br>QADKELTALI RRKFAIKCTT GYSLNALVDF PVDNPIEIIK<br>HLIIGSEGTL GFVSRATYNT VPEWPNKASA FIVFPDVRAA<br>CTGASVLRNE TSVDAVELFD RASLRECENN EDMMRLVPDI<br>KGCDPMAAAL LIECRGQDEA ALQSRIEEVV RVLTAAGLPF<br>GAKAAQPMAI DAYPFHHDQK NAKVFWDVRR GLIPIVGAAR<br>EPGTSMLIED VACPVDKLAD MMIDLIDMFQ RHGYHDASCI |

TABLE 9-continued

Plqq1 Sequences & Other Exemplary Sequences

| Source | SEQ ID NO: | SEQUENCE (5' to 3') |
|---|---|---|
| | | GHALEGNLHL VFSQGFRNKE EVQRFSDMME EMCHLVATKH SGSLKGEHGT GRNVAPFVEM EWGNKAYELM WELKALFDPS HTLNPGVILN RDQDAHIKFL KPSPAASPIV NRCIECGFCE SNCPSRDITL TPRQRISVYR EMYRLKQLGP GASEEEKKQL AAMSSSYAYD GEQTCAADGM CQEKCPVKIN TGDLIKSMRA EHMKEEKTAS GMADWLAANF GVINSNVPRF LNIVNAMYSV VGSAPLSAIS RALNAATNHF VPVWNPYMPK GAAPLKVPAP PAPAAAEASG IPRKVVYMSS CVTRMMGPAA SDTETAAVHE KVMSLFGKAG YEVIIPEGVA SQCCGMMFNS RGFKDAAASK GAELEAALLK ASDNGKIPIV IDTSPCLAQV KSQISEPSLR FALYEPVEFI RHFLVDKLEW KKVRDQVAIH VPCSSKKMGI EESFAKLAGL CANEVVPSGI PCCGMAGDRG MRFPELTGAS LQHLNLPKTC KDGYSTSRTC EMSLSNHAGI NFRGLVYLVD EATAPKKQAA AAKTA |
| Volvox carteri f. nagariensis Glycolate dehydrogenase (XM_002946413) | 48 | ATGACAGCTA TGCAGGCCAA CGGCGGCAGC GGCATTAGCG ATGTTACTGC CACCGCCGCG ACCACGGGGG AGACCTCAGG TGGGGAAGCG GGGCCAGTGG GACGGCTGGA GGCGGCCACG GCGCCAACGG ACGCGGCGGC GCTGGCCTAC TCAGATGCGG GTGCCACCGG CGTAGACGCG CTAGATGAGA CGCGCAAGTT TGTGTTCGCG GAGGAATGGG GCTTTTCGCG CGTGGGAGGT GACCTGCCGG ATGGCACCAC GCCCGCCACG TTTGCCGACA TGTTTCCCGA GCGTTTCTTC GCCTTCAACC CCCTGCGCGC GGTAACGGCG GTGGCGCTAC CACTGGTCGC TATGGCCGTT GGCTACGGCT GGCTGTGGTA CATGCACTCA ATCTGCCCCG CCTGGCAGCA GCTCGCGTGC GCAGCCCTTA TCGGCACCGC TTACACGGGC CTCTTTAAAG TCGCCCACGA GTGTGCGCGC TTCAGCTTTC TGCCTGAAGC TCCTCGCCTC CAAGATGCGC TAGGGCTTGT CCTCATGCTG CCGTCGTTGT ACCCCTTCAC CTCCTGGCGC CTCCATTACA TCCACCATAT GGCGCACCTC AACATGCTGT GGGAGGATAC CTTTGGCTGG CACCCGTACA CGAAGCTGCA GCTGGCCACG GAGCTCCTCT GTGGGCAGCA CTGGCTCCTG GCACTGCGGC GCCTGGCGCT GACCACACCG CTAAAGCTGT TTGCGTCCGT GGGCCACTGG CTTCGCTCCT TTGACGGGCT GGACTTGAAG CGCTTCCACA AAGACACCTA CTGGGCTGTG CTGGCGGGCT GGTCGGGCC CATCCTGTTT TTGGGTTTCG GCATCCCGGC TATCATTAAG ATGTTTGGCT TGTCAGTCCG TCTAGCCGAC CGGGCTTGGG GGGGCTTAGT AAGCGGCTAC CTGCTTCCCT GGCTGGTCTT CCACTTCTGG CTGTCCACTC TATCGCTCCT GCAGCACACC GCACCGCATA TTCCATTCCG CGCCGAGGAC GCGGGCTACG ACTCCGGCCG CGCGGCCATC TGCGGCACCG TGACGGTGCG GCTGCCACGG CCTCTGGAGC TGCTGCTTAA CGACGCCAAC TACTCCCTAC CGCAGCTGGT GGCCCCTGGG ATGCCAGTGT TCACGCGCGC GGAGGCGTAT GAGTACATGC GGGAGCGGTT GCTGCCGTAC CTGACGGAGG CGACGCTTAG CGTAAAACTA CTGACCAACC ATATTACCAA GTGGCAGGTT TATGATGCGG AAAAGGAGAC GTACCTTCCT CTGGATGAGG TCATGCAGGA GCTCGAACGC GACATTGCCA CTCTTATGGA GGAGGCTGAG CAGGCGGAGG AGGAGGAGAA AGTTTCAGGG GGGCCAAGTG GCGGAGCGGT AGAGGGGCAG GGCAAGCGCC TGGCGCAGCT GTTGGGTGCG CAGCTTAAGC AATACATTTC GGAGGTTCGC AGCATCAGCA GCTCAAATGC TGCTGGTCGG GGAGCGTTGG GCAGCGGCCA CACGCCTACG ACGCAGGTCG TCACTGGCCA GCAAACACGC TCTCATGCCC AGGTCGCAGT CCAGCAGGCT ACACAGCAGC ACTTGAAAGT TGTGGTGCCG GCCATCAGGA CCGATCTGGT CGGGAGCGGTG TCTATGGTGT CTGATGGCGA GAAAGTGGAG CCAGGCGTCT TCAAGAACAT TGACGGACAC CGCTTCGACG ACGGTCGCTA CCAGGCTTTT ATTGAGGAAA TCACAAAATT TATCCCCAAG GAGCGGCAGT ACACCGACCC TGTCCGCACG TTCGCGTATG GCATCGACGC GAGTTTCTAC CGCCTTAACC CAAAGCTGGT CGTTAAGGTC CACAATGAAG AAGAAGTTCG GAAGATTTTG CCCATCGCGG AGCGGCTCAA GGTGCCGGTC ACCTTCCGTG CTGCGGGTAC ATCCCTCTCG GGCCAGGCTA TCACCGACTC GGTGCTGATT AAGCTCAGCC ACACCGGCAA GAATTTCCGG AACTACACCG TGCACGGCGA CGGCAGCAGC ATCACAGTGG AGCCGGGCCT CATCGGTGGC GAGGTTAACC GCATCCTGGC GGCGTATCAG AAGAAGCACA AGCTGCCCAT TCAGTACAAG ATAGGCCCAG ACCCGTCTTC CATCGACTCT TGCATGATCG GCGGCATCGT GGCCAACAAC AGCAGCGGCA TGTGCTGCGG TGTCAGCCAA AACACATATC ACACGCTCAA GGATATGCGG GTGTTGTTTG TGGACGGCAC GGTACTGGAT ACGGCAGATC CGGACAGCTG CGCGGCCTTC CTCAAGAGCC ATAAGGCCCT GGTGGACGGC GTCGTGGACC TGGCGCGGCG TGTGCAGGCT GACAGGGAGC TGACGGCTCT TATCCGTCGC |

TABLE 9-continued

Plqq1 Sequences & Other Exemplary Sequences

| Source | SEQ ID NO: | SEQUENCE (5' to 3') |
|---|---|---|
| | | AAGTTTGCCA TCAAATGCAC CACCGGCTAT TCGCTGAATG<br>CGCTGGTGGA TTTCCCGCTG GACAACCCCA TTGAGATTAT<br>CAAGCACGTC ATCATTGGCA GCGAGGGCAC TCTGGGCTTC<br>GTGTCGCGGG CCACCTACAA CACTGTGCCC GAGTGGCCCA<br>ACAAGGCCTC GGCCTTCATC GTCTTCCCGG ACGTGCGGGC<br>GGCATGCATG GGTGCCTCCG TGCTCCGAAA TGAGACCTCT<br>GTGGACGCAG TAGAGCTGTT TGACAGGGCT TCCCTACGCG<br>AGTGCGAGAA CAATGAGGAC ATGATGCGGC TGGTGCCAGA<br>CATCAAGGGC TGCGACCCCA TGGCTGCCGC GGTGCTGATT<br>GAGTGCCGTG GCCAGGACGA GGCGGCGCTG CAGGGTCGTA<br>TTGAGGAGGT GGTCCGTGCT CTTACCTCGG CGGGCCTGCC<br>GGTGGGAGCG AAGGCGGCTG AACCCCGCCC CATCACCGCC<br>TATCCCTTCC ACCACGATGC CAAGAACTCG AAAGTCTTCT<br>GGGACGTGCG CAGGGGTCTG ATTCCGATCG TGGGTGCCGC<br>CCGTGAGCCG GGTACCTCCA TGCTTATTGA GGACGTCGCT<br>TGCCCCGTGG ACAAGCTGGC GGACATGATG ATTGACCTGA<br>TTGACATGTT CCAGCGCTAT GGCTACAACG ACGCTTCGTG<br>CTTCGGCCAC GCGCTGGAGG CAACCTGCA CCTGGTCTTC<br>TCTCAGGGCT TCCGTACCAA GGAGGAGGTA CAGCGATTTG<br>CGGACATGAT GGAGGAGATG TGCTACATCG TGGCCACTAA<br>ACACAGCGGC AGCCTGAAGG GCGAGCATGG CACAGGCCGC<br>AACGTGGCTC CCTTCGTTGA GATGGAATGG GGCAGCAAGG<br>CGTATGAGCT GATGTGGGAG CTCAAGGAGC TGTTTGACCC<br>CAAGTACACG CTCAACCCCG GCGTCATTCT CAACCGGGAC<br>CCCGATGCGC ACATCAAATT CCTCAAGCCT TCGCCTGCTG<br>CTTCGCCAAT CGTTAATCGC TGCATCGAGT GCGGCTTCTG<br>CGAGTCCAAC TGCCCCTCCC GGGACATCAC GCTCACGCCC<br>CGCCAGCGCA TCGCCGTGTA CCGTGAGATG TACCGCCTGA<br>AGCAGCTGGG CCCGGCCGCC AGCGAGGAAG AGAAGCAGCA<br>GTTGGCAGCC ATTACAAGCT CCTATGCTTA CGATGGCGAG<br>CAGACGTGCG CCGCCGACGG CATGTGCCAG GAGAAGTGCC<br>CCGTCAAGAT AAACACAGGC GACATGATCA AGGCTCTCCG<br>CGCCGAGCAC ATGAAGGAGG CCAAGTCCGC CAGTGGTGCT<br>GCCATGTGGA TGGCTAACAA CTTCGGAGTC CTCAACGCCA<br>CAGTGCCGCG CTTCCTGAAC CTCGTTAATT TGGCGCACAG<br>TATCCTGGGC CCCAAGCCGC TTGAGGCCAT CTCCCGGGCG<br>CTGAACGCTG CCACCAATCA CCTGGTGCCC GTCTGGAACC<br>CCTACATGCC CAAGGGCGCC GCGCCGCTGA AGGTGCCCGC<br>TCCGTTCCCT GCACCCGCGG CGTCCTCTGG CGGCATCCCC<br>CGCCGAGTGG TGTACATGCC CTCTTGCGTG ACCCGCATGA<br>TGGGCCCCGC GGCGAGCGAC AAGGAGACGG CCCTCTGTGC A<br>TGAAAGATT TTGAGCCTCT TCAACAAGGC CGGCTACGAG<br>GTCATTGTTC CAGAGGGTGT CAGCAGCCAA TGTTGCGGCA<br>TGATGTTCAA CAGCCGTGGC TTCAAGGACG CCGCTGCCGC<br>CAAGGGTGCC GATCTGGAAG CGGCGCTGCT CAAGGCATCC<br>GATAACGGCA AGATCCCCAT CGTTATGGAC ACTTCGCCAT<br>GCCTGGCGCA GGTTAAGAGC CAAATCTCGG AGCCAGCGCT<br>ACGCTTCGCG CTGTACGAAC CGGTTGAGTT CATCAGGCAC<br>TTCCTGGTTG ACAAACTTGA GTGGCGCAAG GTGCGGGAGC<br>AGGTGGCCAT CCATGTGCCC TGCTCATCCA AGAAGATGGG<br>CATCGAGGAG TCCTTCGCCA AGCTGGCAGG ATTGTGTGCG<br>CACGAGGTTG TCCCGTCGGG CATTCCCTGC TGCGGTATGG<br>CTGGCGACCG TGGAATGCGC TACCCGGAGC TGACTGGCTC<br>CTCACTGCAG CACCTAAACC TGCCCAAGAG CTGCAGCGAT<br>GGCTACTCCA CCAGTCGCAC CTGCGAGATG TCGTTGTCCA<br>ACCACTCGGG CATCAACTTC AGGGGCTGG TCTACTTGGT<br>GGACGAGGCG ACTAGCCCCA AGAAGGCGG AACCGCATGA |
| Volvox<br>carteri<br>f. nagariensis<br>Glycolate<br>dehydrogenase<br>(XM_002946413) | 49 | MTAMQANGGS GISDVTATAA TTGETSGGEA GPVGRLEAAT<br>APTDAAALAY SDAGATGVDG LDETRKFVFA EEWGFSRVGG<br>DLPDGTTPAT FADMFPERFF AFNPLRAVTA VALPLVAMAV<br>GYGWLWYMHS ICPAWQQLAC AALIGTAYTG LFKVAHECAR<br>FSFLPEAPRL QDALGLVLML PSLYPFTSWR LHYIHHMAHL<br>NMLWEDTFGW HPYTKLQLAT ELLCGQHWLL ALRRLALTTP<br>LKLFASVGHW LRSFDGLDLK RFHKDTYWAV LAGWSGPILF<br>LGFGIPAIIK MFGLSVRLAD RAWGGLVSGY LLPWLVPHFW<br>LSTLSLLQHT APHIPFRAED AGYDSGRAAI CGTVTVRLPR<br>PLELLLNDAN YSLPQLVAPG MPVFHAREAY EYMRERLLPY<br>LTEATLSVKL LTNHITKWQV YDAEKETYLP LDEVMQELER<br>DIATLMEEAE QAEEEEKVSG GPSGGAVEGQ GKRLAQLLGA<br>QLKQYISEVR SISSSNAAGR GALGSGHTPT TQVVTGQQTR<br>SHAQVAVQQA TQQHLKVVVP AIRTDLVGAV SMVSDGEKVE<br>PGVFKNIDGH RFDDGRYQAF IEEITKFIPK ERQYTDPVRT<br>FAYGIDASFY RLNPKLVVKV HNEEEVRKIL PIAERLKVPV<br>TFRAAGTSLS GQAITDSVLI KLSHTGKNFR NYTVHGDGSS |

TABLE 9-continued

Plqq1 Sequences & Other Exemplary Sequences

| Source | SEQ ID NO: | SEQUENCE (5' to 3') |
|---|---|---|
| | | ITVEPGLIGG EVNRILAAYQ KKHKLPIQYK IGPDPSSIDS CMIGGIVANN SSGMCCGVSQ NTYHTLKDMR VLFVDGTVLD TADPDSCAAF LKSHKALVDG VVDLARRVQA DRELTALIRR KFAIKCTTGY SLNALVDFPL DNPIEIIKHV IIGSEGTLGF VSRATYNTVP EWPNKASAFI VFPDVRAACM GASVLRNETS VDAVELFDRA SLRECENNED MMRLVPDIKG CDPMAAALLI ECRGQDEAAL QGRIEEVVRA LTSAGLPVGA KAAEPRPITA YPFHHDAKNS KVFWDVRRGL IPIVGAAREP GTSMLIEDVA CPVDKLADMM IDLIDMFQRY GYNDASCFGH ALEGNLHLVF SQGFRTKEEV QRFADMMEEM CYIVATKHSG SLKGEHGTGR NVAPPVEMEW GSKAYELMWE LKELFDPKYT LNPGVILNRD PDAHIKFLKP SPAASPIVNR CIECGFCESN CPSRDITLTP RQRIAVYREM YRLKQLGPAA SEEEKQQLAA ITSSYAYDGE QTCAADGMCQ EKCPVKINTG DMIKALRAEH MKEAKSASGA AMWMANNFGV LNATVPRFLN LVNLAHSILG PKPLEAISRA LNAATNHLVP VWNPYMPKGA APLKVPAPFP APAASSGGIP RRVVYMPSCV TRMMGPAASD KETASVHEKI LSLFNKAGYE VIVPEGVSSQ CCGMMFNSRG FKDAAAAKGA DLEAALLKAS DNGKIPIVMD TSPCLAQVKS QISEPALRFA LYEPVEFIRH FLVDKLEWRK VREQVAIHVP CSSKKMGIEE SFAKLAGLCA HEVVPSGIPC CGMAGDRGMR YPELTGSSLQ HLNLPKSCSD GYSTSRTCEM SLSNHSGINF RGLVYLVDEA TSPKKAATA |

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A transgenic tree plant cell comprising:
    endogenous glycolate transporter Plgg1 and
    one or more heterologous polynucleotides comprising:
        a first promoter operably linked to a polynucleotide sequence encoding a glycolate dehydrogenase;
        a second promoter operably linked to a polynucleotide sequence encoding a malate synthase; and
        an RNAi polynucleotide targeting the endogenous glycolate transporter Plgg1, wherein the RNAi polynucleotide comprises a sense strand comprising at least 21 contiguous nucleotides of the endogenous glycolate transporter Plgg1 and an antisense strand that is fully complementary to the at least 21 contiguous nucleotides of the sense strand, wherein the sense strand and the antisense strand form a dsRNA, wherein expression of the endogenous glycolate transporter Plgg1 in the transgenic tree plant cell is about 20% to 80% of expression of endogenous glycolate transporter Plgg1 in a tree plant cell that is not transformed with the RNAi polynucleotide targeting the endogenous glycolate transporter Plgg1, and wherein the transgenic tree plant cell is from a tree selected from *Populus, Pinus taeda*, and *Picea abies*.

2. The transgenic tree plant cell of claim 1, wherein expression of the endogenous glycolate transporter Plgg1 is about 30% to 70% of expression of endogenous glycolate transporter Plgg1 in a tree plant cell that is not transformed with the RNAi polynucleotide targeting an endogenous glycolate transporter Plgg1.

3. The transgenic tree plant cell of claim 1, wherein the glycolate dehydrogenase is from an algae of the species *Chlamydomonas reinhardtii*.

4. The transgenic tree plant cell of claim 1, wherein the malate synthase is from a plant of the genus *Cucurbita*.

5. The transgenic tree plant cell of claim 1, wherein the RNAi polynucleotide comprises a glycolate transporter Plgg1 polynucleotide sequence from a tree of the genus *Populus*.

6. The transgenic tree plant cell of claim 5, wherein the RNAi polynucleotide comprises a glycolate transporter Plgg1 from a tree of the species *Populus trichocarpa, Populus tremula, Populus alba, Populus alba* x *Populus grandidentata, Populus alba* x *Populus tremula* var. *glandulosa, Populus alba* x *Populus tremuloides, Populus balsamifera, Populus balsamifera* subsp. *trichocarpa, Populus balsamifera* subsp. *trichocarpa* x *Populus deltoides, Populus ciliata, Populus deltoides, Populus euphratica, Populus euramericana, Populus kitakamiensis, Populus lasiocarpa, Populus laurifolia, Populus maximowiczii, Populus maximowiczii* x *Populus balsamifera* subsp. *trichocarpa, Populus nigra, Populus sieboldii* x *Populus grandidentata, Populus suaveolens, Populus szechuanica, Populus tomentosa, Populus tremula* x *Populus tremuloides, Populus wilsonii, Populus canadensis, Populus yunnanensis*, or *Populus tremula* x *alba*.

7. The transgenic tree plant cell of claim 1, wherein the sense strand comprises 21-400 contiguous nucleotides of the glycolate transporter Plgg1.

8. The transgenic tree plant cell of claim 1, wherein the sense strand comprises at least 21 contiguous nucleotides of SEQ ID NO:6.

9. A transgenic tree comprising the transgenic tree plant cell of claim 1.

10. The transgenic tree of claim 9, wherein the transgenic tree comprises at least 10% more biomass accumulation compared to a non-transgenic tree of the same species.

11. The transgenic tree of claim 9, wherein the tree is of the genus *Populus*, or the species *Pinus taeda* or *Picea abies*.

12. The transgenic tree of claim 11, wherein the tree is of the genus *Populus*.

13. The transgenic tree of claim 12, wherein the tree is a hybrid of *Populus tremula* x *Populus alba*.

14. A method for increasing biomass productivity in a tree, said method comprising:
    transforming a tree plant cell comprising endogenous glycolate transporter Plgg1 with one or more heterologous polynucleotides comprising:
        a first promoter operably linked to a polynucleotide sequence encoding a glycolate dehydrogenase;
        a second promoter operably linked to a polynucleotide sequence encoding a malate synthase; and
        an RNAi polynucleotide targeting the endogenous glycolate transporter Plgg1, wherein the RNAi polynucleotide comprises a sense strand comprising at least 21 contiguous nucleotides of the endogenous glycolate transporter Plgg1 and an antisense strand that is fully complementary to the at least 21 contiguous nucleotides of the sense strand, wherein the sense strand and the antisense strand form a dsRNA, wherein expression of the endogenous glycolate transporter Plgg1 in the transformed tree plant cell is about 20% to 80% of expression of endogenous glycolate transporter Plgg1 in a tree plant cell that is not transformed with the RNAi polynucleotide targeting an endogenous glycolate transporter Plgg1, wherein the transgenic tree plant cell is from a tree selected from *Populus, Pinus taeda*, and *Picea abies*, and wherein said transforming increases biomass productivity of the tree.

15. The method of claim 14, wherein the inhibitory polynucleotide targets a glycolate transporter Plg1 from a plant of the genus *Populus*, or the species *Pinus taeda* or *Picea abies*.

16. The method of claim 14, wherein the RNAi polynucleotide targets glycolate transporter Plgg1 from a tree of the species *Populus trichocarpa, Populus tremula, Populus alba, Populus alba* x *Populus grandidentata, Populus alba* x *Populus tremula* var. *glandulosa, Populus alba* x *Populus tremuloides, Populus balsamifera, Populus balsamifera* subsp. *trichocarpa, Populus balsamifera* subsp. *trichocarpa* x *Populus deltoides, Populus ciliata, Populus deltoides, Populus euphratica, Populus euramericana, Populus kitakamiensis, Populus lasiocarpa, Populus laurifolia, Populus maximowiczii, Populus maximowiczii* x *Populus balsamifera* subsp. *trichocarpa, Populus nigra, Populus sieboldii* x *Populus grandidentata, Populus suaveolens, Populus szechuanica, Populus tomentosa, Populus tremula* x *Populus tremuloides, Populus tremuloides, Populus wilsonii, Populus canadensis, Populus yunnanensis*, or *Populus tremula* x *alba*.

17. The method of claim 14, wherein the sense strand comprises 21-400 contiguous nucleotides of the glycolate transporter Plgg1.

18. The method of claim 14, wherein the sense strand comprises at least 21 contiguous nucleotides of SEQ ID NO:6.

19. The method of claim 14, wherein the RNAi polynucleotide further comprises an intron polynucleotide.

20. The method of claim 14, wherein said transforming is carried out by introducing the one or more polynucleotides into the tree plant cell by *Agrobacterium tumefaciens* infection, electroporation, particle bombardment, or protoplast transfection to obtain transgenic tree plant cells.

21. The method of claim 14 further comprising:
regenerating a transgenic tree from the transgenic tree plant cell.

22. The method of claim 21, wherein the transgenic tree shows enhanced biomass productivity compared to a non-transgenic tree of the same species.

23. A method for increasing photosynthetic activity and stomatal conductance under drought conditions in a tree, said method comprising:
transforming a tree plant cell comprising endogenous glycolate transporter Plgg1 with one or more heterologous polynucleotides comprising:
a first promoter operably linked to a polynucleotide sequence encoding a glycolate dehydrogenase;
a second promoter operably linked to a polynucleotide sequence encoding a malate synthase; and
an RNAi polynucleotide targeting the endogenous glycolate transporter Plgg1, wherein the RNAi polynucleotide comprises a sense strand comprising at least 21 contiguous nucleotides of the endogenous glycolate transporter Plgg1 and an antisense strand that is fully complementary to the at least 21 contiguous nucleotides of the sense strand, wherein the sense strand and the antisense strand form a dsRNA, wherein expression of the endogenous glycolate transporter Plgg1 in the transgenic tree plant cell is about 20% to 80% of expression of endogenous glycolate transporter Plgg1 in a tree plant cell that is not transformed with the inhibitory polynucleotide targeting an endogenous glycolate transporter Plgg1, and wherein the transgenic tree plant cell is from a tree selected from *Populus*, *Pinus taeda*, and *Picea abies*;
regenerating a tree from the transformed tree plant cell; and
subjecting the tree to drought conditions, wherein said transforming increases photosynthetic activity and stomatal conductance under drought conditions in the regenerated tree.

24. A polynucleotide construct comprising:
an RNAi polynucleotide comprising a polynucleotide sequence that targets an endogenous glycolate transporter Plgg1 present in a tree plant cell, wherein the RNAi polynucleotide comprises a sense strand comprising at least 21 contiguous nucleotides of the endogenous glycolate transporter Plgg1 and an antisense strand that is fully complementary to the at least 21 contiguous nucleotides of the sense strand, wherein the sense strand and the antisense strand form a dsRNA, wherein when expressed in the tree plant cell, the RNAi polynucleotide reduces expression of the endogenous glycolate transporter Plgg1 by about 20% to 80% of expression of endogenous glycolate transporter Plgg1 in a tree plant cell where the RNAi polynucleotide is not present, and wherein the tree plant cell is from a tree selected from *Populus*, *Pinus taeda*, and *Picea abies*.

25. The polynucleotide construct according to claim 24 further comprising:
a first polynucleotide sequence encoding a glycolate dehydrogenase; and
a first promoter operably linked to the first polynucleotide sequence.

26. The polynucleotide construct according to claim 24 further comprising:
a second polynucleotide sequence encoding a malate synthase; and
a second promoter operably linked to the second polynucleotide sequence.

* * * * *

SEQUENCE LISTING

```
Sequence total quantity: 49
SEQ ID NO: 1            moltype = DNA   length = 3288
FEATURE                 Location/Qualifiers
source                  1..3288
                        mol_type = unassigned DNA
                        organism = Chlamydomonas reinhardtii
misc_feature            1..3288
                        note = glycolate dehydrogenase
SEQUENCE: 1
atgccacgcg gccagggcaa gcgcctggct cagctccttg gagctcagct gaagcagtac    60
gcagcggagg tgcgtggcat cagcacagct ggtggcgctt ctcgcggtgg agctcgagga   120
cctgcatccc ctagctcgct agagcagcag acgcgccagg tcgctcaggt tgctgttcag   180
cagtcgactc agcaggcagt gaaggtcgtt gtgccggcca tcaaagtaga cctggttggt   240
gcggtcagct cggtgtctga gagcgacaag gtggagcggg gtgtgttcaa gaacgtgcag   300
ggccaccgct tcgaggacgg tcgctatgcc gctttttgttg aggagattac aaagtttatc   360
cccaaggagc gccagtactc ggaccccgtg cgcacattcg cgtatggcac ggatgcctcc   420
ttctaccggc ttaacccgaa gctggtagtg aaggtgcaca acgaggacga ggtccgccgc   480
atcatgccca tcgcggagcg gctgcaggtc cctatcacct tccgcgccgc cggcacgtcg   540
ctgtctgggc aggcaattac cgactcggtg ctcattaagc tgagccacac gggcaagaac   600
ttccgcaact taccgtgca cggcgacggt agcgtgatca cggtggagcc gggcctcatt   660
ggcggcgagg tgaaccgcat cctggcggca caccagaaga gaacaagct gcccatccag   720
tacaagatcg gacccgaccc ctcctccatc gacagctgca tgatcggcgg catcgtgtcc   780
aacaacagca gcggcatgtg ctgcggcgtg agccagaaca cctaccacac gctgaaggac   840
atgcgggtgg tgttcgtaga cggaacggtg ctggacacgg ccgaccccaa ctcgtgcacc   900
gccttcatga agagccaccg ctcgctggtg gatggcgtcg tgagcctggc gcgccgcgtg   960
caggccgaca aggagctgac ggcgctcatc cgccgcaagt tcgccatcaa gtgcaccacc  1020
ggctactccc tgaacgcgct ggtggacttc ccggtggaca acccattga gatcatcaag  1080
cacctcatca tcggcagcga gggcacgctg gcttcgtca gccgcgccac ctacaacacc  1140
gtgcccgagt ggcccaacaa ggcctcggcc ttcatcgtgt tcccggacgt gcgcgccgcc  1200
tgcaccggcg cctcggtgct gcgcaacgag acgtccgtgg acgcggtgga gctgtttgac  1260
cgcgccgcc tgcgcgagtg cgagaacaac gaggacatga tgcgcctggt gcccgacatc  1320
aagggctgcg accccatggc ggcagcgctg ctgatcgagt gccgcggcca ggacgaggcc  1380
gcactgcaga gccgcattga ggaggtgtg cgcgtgctga cggcggcggg cctgcccttc  1440
ggcgccaagg ccgcgcagcc catggccatc gacgcctacc ccttccacca cgaccagaag  1500
aacgccaagg tcttctggga cgtgcgcagg ggcctgatcc ccattgtgg cgcggcgcgc  1560
gagcccggca catccatgct gatcgaggac gtggcctgcc ccgtggacaa gctggccgac  1620
atgatgatcg acctgatcga catgttccag cgccacggct accacgacgc ctcctgcttc  1680
ggccacgcgc tcgagggcaa ccttcacttg gtgttctcgc agggcttccg caacaaggag  1740
gaggtgcagc gcttcagcga catgatggag gagatgtgcc acctggtggc caccaagcac  1800
tcgggcagcc tcaagggcga gcacggcacg ggccgcaacg tggcgccgtt cgtggagatg  1860
```

```
gagtggggca acaaggcgta cgagctgatg tgggagctca aggcgctgtt cgacccagc    1920
cacaccctca acccgggcgt catcctcaac cgcgaccagg acgcgcacat caagttcctg    1980
aagccctcgc cgcggcctc gcccatcgtc aaccgctgca tcgagtgcgg cttctgcgag    2040
tccaactgcc cctcgcgcga catcacgctc acgccgcgcc agcgcatctc cgtgtaccgc    2100
gagatgtacc gcctcaagca gctgggcccg ggcgccagca aggaggagaa gaagcagcta    2160
gcggccatga gcagctcgta cgcctacgac ggcgagcaga cgtgcgcggc ggacggcatg    2220
tgccaggaga agtgccccgt caagatcaac acgggagacc tgatcaagtc gatgcgtgcc    2280
gagcacatga aggaggagaa gaccgccagc ggcatggcag actggctggc cgccaacttc    2340
ggcgtcatca actccaacgt gccgcgcttc ctcaacatcg tcaacgccat gcacagcgtg    2400
gtgggctcgg cgcctctgtc cgccatcagc cgcgcgctca acgccgccac caaccacttc    2460
gtgccggtgt ggaaccccta catgcccaag ggcgcggcgc cgctcaaggt gccgcccccg    2520
ccggcgccgg cagctgctga ggcctcgggc atcccgcgca aggtggtgta catgcccagc    2580
tgcgtgacgc gcatgatggg ccccgccgcc tccgacaccg acggcggc ggtgcacgag    2640
aaggtgatga gcctgttcgg caaggccggc tacgaggtga tcatccccga gggcgtgcc    2700
agccagtgct gcggcatgat gttcaacagc cgcggcttca aggaccccgc cgccagcaag    2760
ggcgcggagc tggaggcggc gctgctcaag gcctcggaca atggcaagat ccccatcgtc    2820
atcgacacct cgccctgcct ggcgcaggtg aagagccaga tcagcgagcc gtcgctgcgc    2880
ttcgcgctgt acgagccggt tgagttcatc cggcacttcc tggtgacaa gctggagtgg    2940
aagaaggtgc gcgaccaggt ggccatccac gtgccctgct cctccaagaa gatgggcatc    3000
gaggagtcct tcgcgaagct ggcgggcctg tgcgccaacg aggtggtgcc ctcgggcatt    3060
ccttgctgcg gcatggcggg cgaccgcggc atgcgcttcc ccgagctgac cggcgcctcg    3120
ctgcagcacc tcaacctgcc caagacctgc aaggacgagc actccaccag ccgcacctgc    3180
gagatgtcgc tcagcaacca cgccggcatc aacttcaggg gcctggtgta cctggtggat    3240
gaggccacgg cgcctaagaa gcaggccgcc gctgccaaga ccgcgtaa                  3288

SEQ ID NO: 2          moltype = AA   length = 1095
FEATURE               Location/Qualifiers
source                1..1095
                      mol_type = protein
                      organism = Chlamydomonas reinhardtii
REGION                1..1095
                      note = glycolate dehydrogenase
SEQUENCE: 2
MPRGQGKRLA QLLGAQLKQY AAEVRGISTA GGASRGGARG PASPSSLEQQ TRQVAQVAVQ     60
QSTQQAVKVV VPAIKVDLVG AVSSVSESDK VEPGVFKNVD GHRFEDGRYA AFVEEITKFI    120
PKERQYSDPV RTFAYGTDAS FYRLNPKLVV KVHNEDEVRR IMPIAERLQV PITFRAAGTS    180
LSGQAITDSV LIKLSHTGKN FRNFTVHGDG SVITVEPGLI GGEVNRILAA HQKKNKLPIQ    240
YKIGPDPSSI DSCMIGGIVS NNSSGMCCGV SQNTYHTLKD MRVVFVDGTV LDTADPNSCT    300
AFMKSHRSLV DGVVSLARRV QADKELTALI RRKFAIKCTT GYSLNALVDF PVDNPIEIIK    360
HLIIGSEGTL GFVSRATYNT VPEWPNKASA FIVPPDVRAA CTGASVLRNE TSVDAVELFD    420
RASLRECENN EDMMRLVPDI KGCDPMAAAL LIECRGQDEA ALQSRIEEVV RVLTAAGLPF    480
GAKAAQPMAI DAYPFHHDQK NAKVFWDVRR GLIPIVGAAR EPGTSMLIED VACPVDKLAD    540
MMIDLIDMFQ RHGYHDASCF GHALEGNLHL VFSQGFRNKE EVQRFSDMME EMCHLVATKH    600
SGSLKGEHGT GRNVAPFVEM EWGNKAYELM WELKALFDPS HTLNPGVILN RDQDAHIKFL    660
KPSPAASPIV NRCIECGFCE SNCPSRDITL TPRQRISVYR EMYRLKQLGP GASEEEKKQL    720
AAMSSSYAYD GEQTCAADGM CQEKCPVKIN TGDLIKSMRA EHMKEEKTAS GMADWLAANF    780
GVINSNVPRF LNIVNAMHSV VGSAPLSAIS RALNAATNHF VPVWNPYMPK GAAPLKVPAP    840
PAPAAAEASG IPRKVVYMPS CVTRMMGPAA SDTETAAVHE KVMSLFGKAG YEVIIPEGVA    900
SQCCGMMFNS RGFKDAAASK GAELEAALLK ASDNGKIPIV IDTSPCLAQV KSQISEPSLR    960
FALYEPVEFI RHFLVDKLEW KKVRDQVAIH VPCSSKKMGI EESFAKLAGL CANEVVPSGI   1020
PCCGMAGDRG MRFPELTGAS LQHLNLPKTC KDGYSTSRTC EMSLSNHAGI NFRGLVYLVD   1080
EATAPKKQAA AAKTA                                                     1095

SEQ ID NO: 3          moltype = DNA  length = 1701
FEATURE               Location/Qualifiers
source                1..1701
                      mol_type = unassigned DNA
                      organism = Cucurbita hybrida
misc_feature          1..1701
                      note = malate synthase
SEQUENCE: 3
atgggatcgc tggaatgta ttctgaatcg gcagtaagga agaaaagtag ccgaggctac      60
gatgttccag agggagtgga cattcgggga cgttatgatg aagaatttgc caggattctc    120
aacaaggaag ccttgctgtt tgtggctgat tacacaagga cttttcagaa ccacataagg    180
tattcgatgg aatgccgcag agaagccaaa aggaggtaca tgaaggggc ggtgccgggg    240
tttgatccgg cgaccaagta tataaggaa tctgagtgga catgtgcatc agtccccccg    300
gcagttgcta atcggagagt ggagatcacc ggacctgtgg agcggaagat gatcatcaac    360
gcactcaatt ctggagctaa agttttcatg gcggactttg aagtgcact atcaccaaac    420
tgggagaatt tgatgagggg gcaaattaat ctgaaggatg cagttgatg gactataagc    480
ttccatgaca aagctagaaa caaggttat aaactgaacg atcagacagc caagctcttt    540
gttcgccctc gaggttggca cttcgctgag gctcatatct tcatcgacgg cgagcctgcc    600
accggctgtc ttgtggactt cgggctctac ttttttcaca accatgccaa tttcggcgc    660
tctcaaggtc aaggttctgg cccttttctt taccttccca aatgggagca ctccaggaa    720
gcaaaaatat ggaacagtgt atttgagaga cagagaaga tggcagggat agagagggg    780
agcatcaggg ccactgtgct gattgaaaca cttccagcag tgtttcaaat ggatgaaata    840
ctctatgagc tgagggatca ttctgtggga ttgaactgtg gtagatggga ttacatattc    900
agctatgtca agaccttcca ggctcaccta gatcgcctgt acccgaccg agtccaagtc    960
ggtatggcac acatttcat gaggagttat tctgatctcc ttatcaggac ttgtcacacg   1020
gtggtgtgcc acgtgggagg catggctgct caaattccaa ttagagacga cccgaaggca   1080
```

-continued

```
aatgagatgg cacttgagct agtgaggaag gacaaattga gagaggcaaa ggcaggacat   1140
gatggaacat gggcagcaca tccaggatta atcccagcat gtatggaagt cttcaccaac   1200
agcatgggaa atgcccccaa tcagatccga tctgcaagac gagacgatgc tgcaaaccta   1260
actgaagacg acctcttgca gcaaccgagg ggtgttcgta cattggaagg gctccggttg   1320
aacacccgag tcggaattca gtacctagca gcatggctaa ccgggacagg ctctgtgcct   1380
ctctacaacc ttatggaaga tgcagccaca gctgaaatca gcagggttca aaactggcaa   1440
tggctgaagt atggagtgga attggatgga gatgggcttg gagtgagagt gaacaaggaa   1500
ctgttcgcaa gagtggtgga agaagaaatg gaaaggattg aaagagaagt ggggaaggag   1560
aaattcagga agggaatgta caaagaggct tgcaagatgt tcacaaggca atgcacagcg   1620
ccaaccttgg atgattttct gaccttggat gcgtacaacc acatagtcat acatcatccc   1680
agggagctgt ccaggctctg a                                             1701

SEQ ID NO: 4           moltype = AA  length = 566
FEATURE                Location/Qualifiers
source                 1..566
                       mol_type = protein
                       organism = Cucurbita hybrida
REGION                 1..566
                       note = malate synthase
SEQUENCE: 4
MGSLGMYSES AVRKKSSRGY DVPEGVDIRG RYDEEFARIL NKEALLFVAD LQRTFRNHIR    60
YSMECRREAK RRYNEGAVPG FDPATKYIRE SEWTCASVPP AVADRRVEIT GPVERKMIIN   120
ALNSGAKVFM ADFEDALSPN WENLMRGQIN LKDAVDGTIS FHDKARNKVY KLNDQTAKLF   180
VRPRGWHFAE AHIFIDGEPA TGCLVDFGLY FFHNHANFRR SQGQGSGPFF YLPKMEHSRE   240
AKIWNSVFER AEKMAGIERG SIRATVLIET LPAVFQMDEI LYELRDHSVG LNCGRWDYIF   300
SYVKTFQAHL DRLLPDRVQV GMAQHFMRSY SDLLIRTCHT VVCHVGGMAA QIPIRDDPKA   360
NEMALELVRK DKLREAKAGH DGTWAAHPGL IPACMEVFTN SMGNAPNQIR SARRDDAANL   420
TEDDLLQQPR GVRTLEGLRL NTRVGIQYLA AWLTGTGSVP LYNLMEDAAT AEISRVQNWQ   480
WLKYGVELDG DGLGVRVNKE LFARVVEEEM ERIEREVGKE KFRKGMYKEA CKMFTRQCTA   540
PTLDDFLTLD AYNHIVIHHP RELSRL                                       566

SEQ ID NO: 5           moltype = DNA  length = 6210
FEATURE                Location/Qualifiers
source                 1..6210
                       mol_type = genomic DNA
                       organism = Populus trichocarpa
misc_feature           1..6210
                       note = glycolate transporter Plgg1
SEQUENCE: 5
atggctactc ctttagtcgc tcattccgtt cagctctgtc atcaccactc aaaacaatat     60
tctttcaaat cacaatcacg tgtcaatagg gatatcggta caaaaacact acttggtgtt   120
tacaatggat tccacaatgt atataaccaa tcttattttc ataagccttg ggcacccatt   180
agagttcttg agcctaattc aaggttcttg caaatggttc ctcaagaaac ctgctctcagt   240
cgaggaattt ccaagaaatc tatgagctca gaaggcagta ccagtactag ctcttcatct   300
attttctcaac aggttagtat aaaggtttta ctgttttttct ttttttgcact cctttttatt   360
tttttttatg ctttcctgtt ttgtatgatt tctactaatt ggtattgagt tgttgcattt   420
aattaagctg attcaactat ttgatttacc tccttttat attgattgca taaggtgatt   480
gggatcttgc atttgcttgt ttcacttggg attatccttg caatggataa gttgttgaaa   540
aaggcatttg tggctgctgc tatcaagttt ccaagtgctc tgtttggcat gttctgcata   600
ttctcagttt tagtcattct tgatataact attccggctg ctgcaacaag cttaatgaac   660
ttctttcagc cagcactgtt attcattcag agatggcttc cgttgttcta cgttccatca   720
ttggttgttt tgcctctctc tgttaaagat atccctgctg catcaggtgt caagatttgc   780
ttcatcacag gtaaaacgaa gcttttttgtt gattcattgc ttttcactct ctaaatcttt   840
aatatagttg gcttgatgaa taaaatgtca ctatgaattt gtgataatca cacataatta   900
atgttatcta ttgaaatcac agaaaattact gcaagctcaa aagccaagat aacatagcat   960
ctccttcatt ctccttatgt ttcaagtttt ttgctgacca tttcattatt catatctccg  1020
attccaatgg ccaccatttt ttttctcact ttggtcatta ttcatatacc atccagtcag  1080
cattcccatg tttacttcca ttttggtggg actatttttc aagttgtgtt ttgcaattgt  1140
aataaaataat aataaatg atgataccaaa tgctttctaa taactgcaag tggagggtgg  1200
ttggcgtcac tttgtgtggc gggttttaca gctattgctg tgagaaaaat ggtgaagaca  1260
gaaatgactg atgctgagcc tatggcgaaa ccctctcctt tttctccatt ggaaatatgg  1320
gcttggagtg gggtcttcct tgtatcattt gttgtcgcat tattatatag aacggcatta  1380
gggactgcag ccagaacatg ccttcctttc ctactagcgt ccaccgtgct aggctatatg  1440
gttggttctg ggtaaaatct cagtttcctc agattagcaa cctctgctt gacaattgtt  1500
ttccagacca aattgacgag gaatggaatt gttgcacaca ttcattataa ttgtagccca  1560
gttaaaaaat catggcttta ctctctctggt tttcaggtta ccatctgtg ttaagaaggt  1620
tttccatccc attatttgtt gtgcactatc tgcagatttg gcagcgttgg cctttgggtt  1680
cctttcccaa tctggactcg atcccgttct aggtaccact tttcaaagtg tttgctgtct  1740
tcatttagtt cactcatttt ctgatgtgga gcaacaacaa atgacaacaa ttgttactac  1800
aaaatgcctg tattattttg ttccacaagc catctcttgc ttttcctttc tatcatatgt  1860
gttagtttcc attatgtatt atgtttcctt ctgatacatg tagtgttagt agagaacaaa  1920
acctggaggg gccatttcag gcagtttcca ttgacaaact taggtagtgt ttggtattcc  1980
gaacaaagat ggaccggata tgacaatatt ttttgtgaag ttgttttgtg tacttttgaa  2040
tagtacaaaa atcaattttt atcttgtcca aagctgttct agtagagaaa attgtctcat  2100
tagaagggggt agaacaacct tgtctagttc cttgcgaaag agttaactta ggttgatccg  2160
aatcagcata aaataaaaat agttattgtt ataattatag tttaaacttg gactagagag  2220
ttgactcagg gcaagtttg ggttacggat taggttgact attgactcaa gtcaatgtaa  2280
ggataaaaat gtttattatc gtagttttaa aacttgactt agggtcgaac cggggcaaag  2340
ccccgatcac gggtcgggtt gactattgat ctaggtcaat gtaaggataa aattattgtt  2400
```

```
atcatagctt taaaacctga ctaggggtt gacccgggtc acgggttggt tgaccattga    2460
gccgagtcaa cgtaaagata aaaatgatta ttatcacagt tttaaaacct gatttaggag    2520
ttgacctggg ataagaccta agtcacaggt tgagatgatt attgaacaag gtcaatgtaa    2580
agataaaagt gtttattatt atagtttaa agtctaacta ggaggtcaac tcgggtaaag    2640
tccctgtcac aggtttggtt aaccattgac ccaggtcaat ataaagataa aagtagcttg    2700
agttacaagt cggggttgacc attgatctga gttaatgtaa ggataaaaat agttattatc    2760
atagtattaa aactcgacta ggagatcgac ctgaggtaag acccatgtca cgggtcgaga    2820
tggtcaactt gttttgaccc aagataacgt aagagtaaga ataattatta tcaaaatttt    2880
aaaatccgac tcgaggttca gcttgagtca tgggttggga gggttaacgt aagaataaaa    2940
atgattatta ttataatttt aaaactcaat ttaaaggtcg atccggggca aggcctgagt    3000
tatgggttga gatggtcagc ttgggttgac ttaggtcaat atatagataa aaatagttat    3060
tatcataatt ttaaaaccta acttgggggt cgacctgggg caaggtttga gtcttaagat    3120
gagagggtca acctaagttg acaaaatatt ttgtttttta aaaaaatcaa aacaatttg    3180
ttttataaaa aaaaatdaaa aagtcaaaa ggatttctta gccttgtttt atcttgggtc    3240
gcaagtcgac ctgattttttt aaccgagtag ggtcggatca attgtttctt tatttttttct    3300
caaacttaga ttagtccaat tcttgtgtca gtcgggctc atccggtatc taccaaacac    3360
gaaataaaat aaattgtcta gttcaattca aagcacacta aatacaaaa caaaacaatt    3420
atttgtcgag tccaattaat attgctagc ataccaaaca ctaccctacc actcatagcc    3480
tttgtgcaaa atgttgaggg acctcgaacg ttttatttat tgcatcactt gtgctaaatac    3540
tgttttgtca atgataaaaa agatggttat ttatgatcta atgatgaaca cttctataat    3600
tcaaaactga agttaactga tatatagttt tacaaatatt ttggacaaca ttttttaaat    3660
ttcagggatg aaaatcttaa agttcaaaag ccgtttgat ctagtttctg ttggaattca    3720
aatcacatac catgtgaact ccctctttttt tcctccatcc ttctctatgg tcacatttttt    3780
ttcattaagt ttttttcatat ctatttttaa gctcatttttc tgtacttcct cattgtagtt    3840
atggtaattt tcttccaatg cacacaggat attacttac aaaagtttca tctaatcctg    3900
gagctgtgta tgtgttaatg ggatcttga gacctgtcat tcttttctttt gccttctcaa    3960
tgttcaagca gcgaaggta acttcttttc tcacaatcca tgccaacagg tcggggttcat    4020
tttgtattaa gtggatatgt ttcatctgtg ctgttactca ggaaggacta gcggttcctt    4080
ttatttaatt gtaactattt ggtgttgcca accaaactat ctggtgttgc caaccaaact    4140
atctgctata cattatttttt tttcatttgg taatggaaga gatgcgtttt gaaattcaga    4200
gtagagaata agcaatgaaa aacctcaaaa tatttagacc ttgcaagaat ctaggaatct    4260
agaatattgc atctacctt atatgaattt atcctcagta gtattctatg tatgctttgt    4320
cattacatgg tttgttgtcc tcgattcaga ataataaaaaa tttgtcatca gatgatgctc    4380
ttaacttact ggtccttttg tcatggcaat gtgagtttat atactctggt gtttctgcag    4440
cttgttaaga gacatgcagc tgagattttc acgtccgtca ttgttgcaac actatttttta    4500
ttgtattcaa cggctctcgt gggacgtcta gttgggttag aaccaacgtt gactgtatcc    4560
attattccca gatgtataac cgtggcatta gccctcagca ttgtgtcatt cttttgaaggt    4620
atagtaatgt tcagaagcca gctggaagca gggaattcca taaatgggca tccactagtg    4680
atgctaaaat taatttttga catatcaaac accgttattc tgagatgaat tcatttccaa    4740
tttacttaac gactttggtc agttagaaca caatgtactg cagatgattg gtgtgactca    4800
ttaccatttt taatcgaatt aattttacat attggttgta ggtgccaatt catctctcac    4860
agctgctgta gttgttgtaa ctggtctcat tggagcaaat tttgtacaag cagtgctcga    4920
taaattaaat tttcgtgatc ccattgctcg aggaatagca actgcttcca ggtttgtggt    4980
ttaccaaaga caaatcagta cgaactcaag cactaaacaa tctttgcaag catagaccct    5040
tccctttctt tagtaaatat aatgatgtgt catatcagct acaagcaact atctttctca    5100
tagctcacct gtatagtttt ctttcagggg actgcaacaa aaatgcatct gggaccaata    5160
ctttgtacta acaaaatgct tgctgttggc cagaaactgg aaactgaatc tcctggggaa    5220
cttaaaactg gttaataatt aagctatttta atatgtagaa aattctgaat gtcactgaga    5280
ttcttattgc tgaatcttat aaaaatcaaa atcattttag aattggacta gtcaatgaaa    5340
ggagatctgt gttttctgt tttggttgaa tattttagtc attttggtta tagcatataa    5400
aaacaaaacc gtggattgaa aataagaaga aagatagatt gctcgaactt tgctcactga    5460
attggacttg atgcacaatc ttgagttatg ctttaaaaac cttacccaag tttgtttgtg    5520
acttcggtta tagtcgcagc ttgtgatgct cagataagct cagttacct gttctgttca    5580
agagtgtaca acctgacatg ctcagtcctg agtattatat tcatatccta ctttagtttt    5640
cctgtgtgaa gattttgcaa agttttgtag gaactgtgc ccattactgc atttatgctt    5700
atccttctta attgtttcag tgctcatgga ctgggaactg cagcattgtc agccaaggaa    5760
cctgaggcac ttcatttttg tgccattgct tatgctctca ctggtatatt tggttcattg    5820
ttttgttcag ttcctgcagt taggcaaagc ttacttgcaa taattggctg aaagattggg    5880
cagcttttgg ttattggtgg ccagacacac ttttgattga ttatccttgt ccacccacag    5940
catgattttt agcaagtaca cagtgctaat agccaacctt gtattattga ttacagtcaa    6000
ttatgtatag aagttgacat catccttctg caaaaactcc tcacctcctt taaattcctt    6060
taaattatga atagtgaact gattgtcttc ttgttagaag cggtcagct ggctgaaaag    6120
caaaagctaa aggtcaaagg taaattatct attctacacc ttgagagggt ggaaaatcca    6180
gtggatacca agaagccac tgttgctcag                                       6210
```

SEQ ID NO: 6           moltype = DNA   length = 1575
FEATURE                Location/Qualifiers
source                 1..1575
                       mol_type = unassigned DNA
                       organism = Populus trichocarpa
misc_feature           1..1575
                       note = PtPlgg1
SEQUENCE: 6
```
atggctactc ctttagtcgc tcattccgtt cagctctgtc atcaccactc aaaacaatat      60
tctttcaaat cacaatcacg tgtcaatagg gatatcggta caaaaacact acttggtgtt     120
tacaatggat tccacaatgt atataaccaa tcttatttc ataagcctg ggcacccatt      180
agagttcttg agcctaattc aaggttcttg caaatgggtc ctcaagaaac ctgctctagt     240
cgaggaattt ccaagaaatc tatgagctca gaaggcagta ccagtactag ctcttcatct     300
atttctcaac aggtgattgg gatcttgcat ttgcttgttt cacttgggat tatccttgca     360
```

```
atggataagt tgttgaaaaa ggcattgtg gctgctgcta tcaagttccc aagtgctctg    420
tttggcatgt tctgcatatt ctcagtttta gtcattcttg atataactat tccggctgct    480
gcaacaagct taatgaactt ctttcagcca gcactgttat tcattcagag atggcttccg    540
ttgttctacg ttccatcatt ggttgttttg cctctctctg ttaaagatat ccctgctgca    600
tcaggtgtca agatttgctt catcacagct ggagggtgct tggcgtcact ttgtgtggcg    660
ggttttacag ctattgctgt gagaaaaatg gtgaagacag aaatgactga tgctgagcct    720
atggcgaaac cctctccttt ttctccattg gaaatatggg cttggagtgg gtcttccttt    780
gtatcatttg ttgtcgcatt attatataga acggcattag ggactgcagc cagaacatgc    840
cttcctttcc tactagcgtc caccgtgcta ggctatatgt tggttctgg gttaccatct    900
ggtgttaaga aggttttcca tcccattatt tgttgtgcac tatctgcaga tttggcagcg    960
ttggcctttg ggttccttc ccaatctgga ctcgatcccg ttctaggata ttaccttaca   1020
aaagtttcat ctaatcctgg agctggtgat gtgttaatgg gattcttggg acctgtcatt   1080
ctttcttttg ccttctcaat gttcaagcag cgaaagcttg ttaagagaca tgcagctgag   1140
attttcacgt ccgtcattgt tgcaacacta ttttcattgt attcaacggc tctcgtgaca   1200
cgtctagttg ggttagaacc aacgttgact gtatccatta ttcccagatg tataaccgtg   1260
gcattagccc tcagcattgt gtcattcttt gaaggtgcca attcatctct cacagctgct   1320
gtagttgttg taactggtct cattggagca aattttgtac aagcagtgct cgataaatta   1380
aattttcgtg atcccattgc tcgaggaata gcaactgcct ccagtgctca tggactggga   1440
actgcagcat tgtcagccaa ggaacctgag gcacttccat tttgtgccat tgcttatgct   1500
ctcactggta tatttggttc attgttttgt tcagttcctg cagtaggca aagcttactt   1560
gcaataattg gctga                                                   1575

SEQ ID NO: 7            moltype = AA   length = 524
FEATURE                 Location/Qualifiers
source                  1..524
                        mol_type = protein
                        organism = Populus trichocarpa
REGION                  1..524
                        note = PtPlgg1
SEQUENCE: 7
MATPLVAHSV QLCHHHSKQY SFKSQSRVNR DIGTKTLLGV YNGFHNVYNQ SYFHKPWAPI    60
RVLEPNSRFL QMGPQETCSS RGISKKSMSS EGSTSTSSSS ISQQVIGILH LLVSLGIILA   120
MDKLLKKAFV AAAIKFPSAL FGMFCIFSVL VILDITIPAA ATSLMNFFQP ALLFIQRWLP   180
LFYVPSLVVL PLSVKDIPAA SGVKICFITA GGWLASLCVA GFTAIAVRKM VKTEMTDAEP   240
MAKPSPFSPL EIWAWSGVFL VSFVVALLYR TALGTAARTC LPFLLASTVL GYMVGSGLPS   300
GVKKVFHPII CCALSADLAA LAFGFLSQSG LDPVLGYYLT KVSSNPGAGD VLMGFLGPVI   360
LSFAFSMFKQ RKLVKRHAAE IFTSVIVATL FSLYSTALVG RLVGLEPTLT VSIIPRCITV   420
ALALSIVSFF EGANSSLTAA VVVVTGLIGA NFVQAVLDKL NFRDPIARGI ATASSAHGLG   480
TAALSAKEPE ALPFCAIAYA LTGIFGSLFC SVPAVRQSLL AIIG                    524

SEQ ID NO: 8            moltype = DNA   length = 257
FEATURE                 Location/Qualifiers
source                  1..257
                        mol_type = other DNA
                        organism = synthetic construct
misc_feature            1..257
                        note = PtPlgg1 sense direction
SEQUENCE: 8
ggaaatatgg gcttggagtg ggtcttcct tgtatcattt gttgtcgcat tattatatag     60
aacggcatta gggactgcag ccagaacatg ccttcctttc ctactagcgt ccaccgtgct   120
aggctatatg ttggttctg gttaccatc tggtgttaag aaggttttcc atcccattat    180
ttgttgtgca ctatctgcag atttggcagc gttggccttt gggttccttt cccaatctgg   240
actcgatccc gttctag                                                  257

SEQ ID NO: 9            moltype = DNA   length = 257
FEATURE                 Location/Qualifiers
source                  1..257
                        mol_type = other DNA
                        organism = synthetic construct
misc_feature            1..257
                        note = PtPlgg1 antisense direction
SEQUENCE: 9
ctagaacggg atcgagtcca gattgggaaa ggaacccaaa ggccaacgct gccaaatctg     60
cagatagtgc acaacaaata atgggatgga aaaccttctt aacaccagat ggtaacccag   120
aaccaaccat atagcctagc acggtggacg ctagtaggaa aggaaggcat gttctggctg   180
cagtccctaa tgccgttcta tataataatg cgacaacaaa tgatacaagg aagacccac   240
tccaagccca tatttcc                                                  257

SEQ ID NO: 10           moltype = DNA   length = 23
FEATURE                 Location/Qualifiers
source                  1..23
                        mol_type = other DNA
                        organism = synthetic construct
misc_feature            1..23
                        note = Plgg1 primer
SEQUENCE: 10
caggtgtcaa gatttgcttc atc                                           23
```

```
SEQ ID NO: 11              moltype = DNA   length = 19
FEATURE                    Location/Qualifiers
source                     1..19
                           mol_type = other DNA
                           organism = synthetic construct
misc_feature               1..19
                           note = Plgg1 primer
SEQUENCE: 11
actccaagcc cacatttcc                                                        19

SEQ ID NO: 12              moltype = DNA   length = 21
FEATURE                    Location/Qualifiers
source                     1..21
                           mol_type = other DNA
                           organism = synthetic construct
misc_feature               1..21
                           note = PtACT2 primer
SEQUENCE: 12
actcacacca tcaccagaat c                                                     21

SEQ ID NO: 13              moltype = DNA   length = 22
FEATURE                    Location/Qualifiers
source                     1..22
                           mol_type = other DNA
                           organism = synthetic construct
misc_feature               1..22
                           note = PtACT2 primer
SEQUENCE: 13
ctcaaccta aggctaacag ag                                                     22

SEQ ID NO: 14              moltype = DNA   length = 25
FEATURE                    Location/Qualifiers
source                     1..25
                           mol_type = other DNA
                           organism = synthetic construct
misc_feature               1..25
                           note = ChMS primer
SEQUENCE: 14
ccacataagg tattcgatgg aatgc                                                 25

SEQ ID NO: 15              moltype = DNA   length = 21
FEATURE                    Location/Qualifiers
source                     1..21
                           mol_type = other DNA
                           organism = synthetic construct
misc_feature               1..21
                           note = ChMS primer
SEQUENCE: 15
gactgatgca catgtccact c                                                     21

SEQ ID NO: 16              moltype = DNA   length = 23
FEATURE                    Location/Qualifiers
source                     1..23
                           mol_type = other DNA
                           organism = synthetic construct
misc_feature               1..23
                           note = CrGDH primer
SEQUENCE: 16
cacatcaagt tcctgaagcc ctc                                                   23

SEQ ID NO: 17              moltype = DNA   length = 21
FEATURE                    Location/Qualifiers
source                     1..21
                           mol_type = other DNA
                           organism = synthetic construct
misc_feature               1..21
                           note = CrGDH primer
SEQUENCE: 17
atctcgcggt acacggagat g                                                     21

SEQ ID NO: 18              moltype = DNA   length = 21
FEATURE                    Location/Qualifiers
source                     1..21
                           mol_type = other DNA
                           organism = synthetic construct
misc_feature               1..21
                           note = nptII primer
SEQUENCE: 18
cctgccgaga aagtatccat c                                                     21
```

```
SEQ ID NO: 19           moltype = DNA   length = 20
FEATURE                 Location/Qualifiers
source                  1..20
                        mol_type = other DNA
                        organism = synthetic construct
misc_feature            1..20
                        note = nptII primer
SEQUENCE: 19
catcctgatc gacaagaccg                                                  20

SEQ ID NO: 20           moltype = DNA   length = 23
FEATURE                 Location/Qualifiers
source                  1..23
                        mol_type = other DNA
                        organism = synthetic construct
misc_feature            1..23
                        note = Plgg1 primer
SEQUENCE: 20
caggtgtcaa gatttgcttc atc                                              23

SEQ ID NO: 21           moltype = DNA   length = 22
FEATURE                 Location/Qualifiers
source                  1..22
                        mol_type = other DNA
                        organism = synthetic construct
misc_feature            1..22
                        note = Plgg1 probe
SEQUENCE: 21
ctttgcgtgg cgggtttcac ag                                               22

SEQ ID NO: 22           moltype = DNA   length = 21
FEATURE                 Location/Qualifiers
source                  1..21
                        mol_type = other DNA
                        organism = synthetic construct
misc_feature            1..21
                        note = Plgg1 primer
SEQUENCE: 22
agcgtcagtc atttctgtct t                                                21

SEQ ID NO: 23           moltype = DNA   length = 21
FEATURE                 Location/Qualifiers
source                  1..21
                        mol_type = other DNA
                        organism = synthetic construct
misc_feature            1..21
                        note = PtACT2 primer
SEQUENCE: 23
ctgcaatgta tgttgccatc c                                                21

SEQ ID NO: 24           moltype = DNA   length = 24
FEATURE                 Location/Qualifiers
source                  1..24
                        mol_type = other DNA
                        organism = synthetic construct
misc_feature            1..24
                        note = PtACT2 probe
SEQUENCE: 24
actggcatac agggaaagga cagc                                             24

SEQ ID NO: 25           moltype = DNA   length = 20
FEATURE                 Location/Qualifiers
source                  1..20
                        mol_type = other DNA
                        organism = synthetic construct
misc_feature            1..20
                        note = PtACT2 primer
SEQUENCE: 25
cacaccatca ccagaatcca                                                  20

SEQ ID NO: 26           moltype = DNA   length = 21
FEATURE                 Location/Qualifiers
source                  1..21
                        mol_type = other DNA
                        organism = synthetic construct
misc_feature            1..21
                        note = PtEF1B-1 primer
SEQUENCE: 26
catcactacc actccacaca a                                                21
```

```
SEQ ID NO: 27           moltype = DNA   length = 30
FEATURE                 Location/Qualifiers
source                  1..30
                        mol_type = other DNA
                        organism = synthetic construct
misc_feature            1..30
                        note = PtEF1B-1 probe
SEQUENCE: 27
tcctctttca atcacactgt ttatcgctct                                          30

SEQ ID NO: 28           moltype = DNA   length = 25
FEATURE                 Location/Qualifiers
source                  1..25
                        mol_type = other DNA
                        organism = synthetic construct
misc_feature            1..25
                        note = PtEF1B-1 primer
SEQUENCE: 28
tttcaattac ttggaagatg ggatg                                               25

SEQ ID NO: 29           moltype = DNA   length = 18
FEATURE                 Location/Qualifiers
source                  1..18
                        mol_type = other DNA
                        organism = synthetic construct
misc_feature            1..18
                        note = CrGDH primer
SEQUENCE: 29
aaggcgtacg agctgatg                                                       18

SEQ ID NO: 30           moltype = DNA   length = 20
FEATURE                 Location/Qualifiers
source                  1..20
                        mol_type = other DNA
                        organism = synthetic construct
misc_feature            1..20
                        note = CrGDH probe
SEQUENCE: 30
aacccgggcg tcatcctcaa                                                     20

SEQ ID NO: 31           moltype = DNA   length = 20
FEATURE                 Location/Qualifiers
source                  1..20
                        mol_type = other DNA
                        organism = synthetic construct
misc_feature            1..20
                        note = CrGDH primer
SEQUENCE: 31
gagggcttca ggaacttgat                                                     20

SEQ ID NO: 32           moltype = DNA   length = 19
FEATURE                 Location/Qualifiers
source                  1..19
                        mol_type = other DNA
                        organism = synthetic construct
misc_feature            1..19
                        note = ChMS primer
SEQUENCE: 32
atggaatgcc gcagagaag                                                      19

SEQ ID NO: 33           moltype = DNA   length = 24
FEATURE                 Location/Qualifiers
source                  1..24
                        mol_type = other DNA
                        organism = synthetic construct
misc_feature            1..24
                        note = ChMS probe
SEQUENCE: 33
atacttggtc gccggatcaa accc                                                24

SEQ ID NO: 34           moltype = DNA   length = 21
FEATURE                 Location/Qualifiers
source                  1..21
                        mol_type = other DNA
                        organism = synthetic construct
misc_feature            1..21
                        note = ChMS primer
SEQUENCE: 34
gatgcacatg tccactcaga t                                                   21
```

-continued

```
SEQ ID NO: 35          moltype = DNA   length = 1344
FEATURE                Location/Qualifiers
source                 1..1344
                       mol_type = unassigned DNA
                       organism = Pinus taeda
misc_feature           1..1344
                       note = Plgg1
SEQUENCE: 35
atggcttcat cccaccaatt ccaaacttca tggctgctca cacggagacc gttgggagac   60
gcctctttgc gtttatatca attacccogc acgaccacaa aagagcagag gaaaaattat  120
gacaattgca gctgttgggc gcagaggaga agagaggcag ctgtcgctgc agcaatcaga  180
attaatggtg agcgtaagtt catgttcacg gggtttggca ggcaaaggcc aaggcgaagt  240
catgaaataa taatggtgaa agcctttgaa aaggatgcca gaggcctccc ggatggctcc  300
ctcaaggtgg gtcgtgtggc gcatttggtg gtttcgttgg gcataattct ggccatcgac  360
aaggccttga aaaggctctt cacggctgcc atgataaagt tccctagcgc attgtttgga  420
atgttctgca tattttccgt gctgtcaatc tcgacgtca tcagaccggc agcggcaacg  480
gctctactga acttttttga gccggcaaca acgttcatac agagatggct tccgctcttc  540
tacgtgccgt cgctggtagt gttgcccta gctgtgaagg gaatccctgc ttcttccgga  600
atgaagattg gcgcaattct tgttggaggc tgggcagcat cactctatgt tgcagggtac  660
acagccattg ccgtaagaaa gatggtcaga acaaaaatga tagcagcaga gcccatgcca  720
aagccttctc cgttttcaac aatagagatt tggttctgga ctattatctt gtcagtttca  780
tttatattga ctgttctttc accttcttgca tttggaactt atgctcgaac atgccttcca  840
tgtcttttag cggcaactgc gttaggattc atccttggat ctggatttcc acctactgcc  900
aagaagctac tacatccaat tattacttgt gccctatctg cggatttggc agcctttgct  960
tgtgggatct ccacaggatt gggctttgaa tccacgctag gggcctattt aactaaaagt 1020
gcaaccaatc ctggtgctgg tgatatcttg atgggatttc ttggatctgt gattctttca 1080
ttcgctttct caatgttccg tcagagaaag cttgtcaaac ggcatgctgc ggagatcttc 1140
tcagctgtgg tggtttcaac aatttttttct ctgtactcaa cagcagctat gggccgaatg 1200
attggactga aaccaacctt aactgttccc attttgccaa gatgtattac tgttgcacta 1260
gcattgagca ttgtctcgct ttttgatggg caatataact ctcgggcgga ttgtccttca 1320
gggtctaggg atgaaagaaa atga                                        1344

SEQ ID NO: 36          moltype = DNA   length = 255
FEATURE                Location/Qualifiers
source                 1..255
                       mol_type = other DNA
                       organism = synthetic construct
misc_feature           1..255
                       note = Plgg1 for RNAi
SEQUENCE: 36
atggcttcat cccaccaatt ccaaacttca tggctgctca cacggagacc gttgggagac   60
gcctctttgc gtttatatca attacccogc acgaccacaa aagagcagag gaaaaattat  120
gacaattgca gctgttgggc gcagaggaga agagaggcag ctgtcgctgc agcaatcaga  180
attaatggtg agcgtaagtt catgttcacg gggtttggca ggcaaaggcc aaggcgaagt  240
catgaaataa taatg                                                   255

SEQ ID NO: 37          moltype = DNA   length = 255
FEATURE                Location/Qualifiers
source                 1..255
                       mol_type = other DNA
                       organism = synthetic construct
misc_feature           1..255
                       note = Plgg1 for RNAi
SEQUENCE: 37
cattattatt tcatgacttc gccttggcct ttgcctgcca aacccgtga acatgaactt   60
acgctcacca ttaattctga ttgctgcagc gacagctgcc tctcttctcc tctgcgccca  120
acagctgcaa ttgtcataat ttttcctctg ctcttttgtg gtcgtgcggg gtaattgata  180
taaacgcaaa gaggcgtctc ccaacggtct ccgtgtgagc agccatgaag tttggaattg  240
gtgggatgaa gccat                                                   255

SEQ ID NO: 38          moltype = DNA   length = 1581
FEATURE                Location/Qualifiers
source                 1..1581
                       mol_type = unassigned DNA
                       organism = Populus alba
misc_feature           1..1581
                       note = Plgg1
SEQUENCE: 38
atggctactc ctttagtcgc tctttccgtt caactctgtc atccactc aaaacaatat     60
tctttcaaat cacaatcaca atcacgtgtg aataggatt tccgtacaaa aacactactt  120
ggtgtttaca atggattcca aaatgtatat aaccaatctt attttcataa gccttgggca  180
cccattagag ttcttgagcc taattcaagg ttcttgcaaa tgggtcctca agaaacctgc  240
tctagtcgag gaatttccaa gaaatctatg agctcagaag gcagtaccag tactagctct  300
tcatcatttt ctcaacaggt gattgggatc ttgcatttgc ttgtttcact tgggattatc  360
cttgcaatgg ataagttgtt gaaaaggca tttgtggctg ctgctatcaa gtttccaagt  420
gctctgtttg gcatgttctg catattctca gtttagtga ttcttgatat aactattccg  480
gctgctgcaa caagcttaat gaacttcttt gagccagcac tgtattcat tcagagatgg  540
cttccgttgt tctacgttcc atcattggtt gttttgcctc tctctgttaa agatatccct  600
gctgcatcag gtgtcaagat ttgcttcatc acagctggag ggtggctggc gtcactttgt  660
```

```
gtggcgggtt tcacagctat tgctgtgaga aaaatggtga agacagaaat gactgacgct    720
gagcctatgg cgaaaccctc tccttttcct ccattggaaa tgtgggcttg gagtggggtc    780
ttccttgtat catttgttgt cgcattatta tatagaacgg cattgggac tgcagccaga     840
acatgccttc ctttcctact agcgtccacc gtgctaggct atatggttgg ttctgggtta    900
ccatctggtg ttaagaaggt tttccatccc attatttgtt gtgcactatc tgcagatttg    960
gcagcgttgg cctttgggta cctttcccaa tctggacttg atcccgttct aggatattac   1020
cttacaaaag tttcatctaa tcctggagct ggtgatgtgt taatgggatt cttgggacct   1080
gtcattcttt cttttgcctt ctcaatgttc aagcagcgaa agcttgttaa gagacatgca   1140
gctgagattt tcacgtcggt cattgtttca acactatttt cattgtattc aacggctctc   1200
gtgggacgtc tagttgggtt agaaccaacg ttgactgtat ccattattcc cagatgtata   1260
accgtggcat tagcccctcag cattgtgtca ttctttgaag gtgccaattc atctctcaca   1320
gctgctgtag ttgttgtaac tggtctcatt ggagcaaatt ttgtacaagc agtgcttgat   1380
aaattaagtt ttcgtgatcc cattgctcga ggaatagcta ctgcttccag tgctcatgga   1440
ctgggaactg cagcattgtc agccaaggaa cctgaggcac ttccattttg tgccattgct   1500
tatgctctca ctggtatatt tggttcattg ttttgttcag ttcctgcagt taggcaaagc   1560
ttacttgcaa taattggctg a                                             1581

SEQ ID NO: 39         moltype = DNA   length = 1575
FEATURE               Location/Qualifiers
source                1..1575
                      mol_type = unassigned DNA
                      organism = Populus tremula
misc_feature          1..1575
                      note = Plgg1
SEQUENCE: 39
atggctactc ctttagtcgc tctttccgtt caactctgtc atcaccactc aaaacaatat     60
tctttcaaat cacatcacg tgtcaatagg gatttccgta cgaaaacact acttggtgtt    120
tacaatggat tccaaaatgt atataaccaa tcttattttc ataagccttg ggcacccatt    180
agagttcttg agcctaattc aaggttcttg caaatgggtc ctcaagaaac ctgctctagt    240
cgaggaattt ccaagaaatc tatgagctca gaaggccagta ccagtactag ctcttcatct    300
atttctcaac aggtgattgg gatcttgcat ttgcttgttt cacttgggat tatccttgca    360
atggataagt tgttgaaaaa ggcatttgtg gctgctgcta tcaagtttcc aagtgctctg    420
tttggcatgt tctgcatatt ctcggtttta gtgattcttg ataactat tccggctgct      480
gcaacaagct taatgaactt cttttgagcca gcactgtca tcattcagag atggcttccg    540
ttgttctacg ttccatcatt ggttgttttg cctctctctg ttaaagatat ccctgctgca    600
tcaggtgtca agatctgctt catcacagct ggagggtggc tggcgtcact ttgcgtggcg    660
ggtttcacag ctattgctgt gagaaaattg gtgaagacag aaatgactga cgctgagcct    720
atggcgaaac cctctccttt ttctccattg gaaatgtggg cttggagtgg ggtcttcctt    780
gtatcatttg ttgtcgcatt attatataga acggcattgg gactgcagcc agaacatgc    840
cttcctttcc tactagcgtc caccgtgcta ggctatatgg ttggttctgg gttaccatct    900
ggtgttaaga aggttttcca tcccattatt tgctgtgcac tatctgcaga tttggcagcg    960
ttggcctttg gtaccttttc ccaatctgga cttgatcccg ttctaggata ttaccttaca   1020
aaagtttcat ctaatcctgg agctggtgat gtgttaatgg gattcttggg acctgtcatt   1080
cttttctttg ccttctcaat gttcaagcag cgaaagcttg ttaagagaca tgcagctgag   1140
attttcacgt cggtcattgt ttcaacacta ttttcattgt attcaacggc tctcgtggga   1200
cgtctagttg ggttagaacc aacgttgact gtatccatta ttccccagatg tataaccgtg   1260
gcattagccc tcagcattgt gtcattcttt gaaggtgcca attcatctct cacagctgct   1320
gtagttgttg taactggtct cattggagca aattttgtac aagcagtgct cgataaatta   1380
aattttcgtg atcccattgc tcgaggaata gcaactgctt ccagtgctca tggactggga   1440
actgcagcat tgtcagccaa ggaacctgag gcacttccat tttgtgccat tgcttatgct   1500
ctcactggta tatttggttc attgttttgt tcagttcctg cagttaggca aagcttactt   1560
gcaataattg gctga                                                    1575

SEQ ID NO: 40         moltype = DNA   length = 1578
FEATURE               Location/Qualifiers
source                1..1578
                      mol_type = unassigned DNA
                      organism = Populus euphratica
misc_feature          1..1578
                      note = Plgg1
SEQUENCE: 40
atggctactc ctttagtcgc tcattccgtt ctactctgtc atcaccactc aaaacaatat     60
cctttcaaat cgcaatcacg tgtcgatagg gatttccgta cgaaaacact acttggtgtt    120
tacaatggat tccaaaatgt atataaccaa tcttattttc ataagccttg ggcacccatt    180
agagttcttg agcctaattt aaggttcttg caaatgggtc ctcaagaaac ctgctctagt    240
cgacgaattt ccaagaaatc tatgagctca gaaggcagta ccagtagtac tagctcttca    300
tctatttctc aacaggtgat tgggatcttg catttgcttg tttcacttgg gattatcctt    360
gcaatggata agttgttgaa aaaggcattt gtggctgctg ctattaagtt tccaagtgct    420
ctatttggca tgttctgcat attctcagtt ttagtcattg tgattctcct attccgctgct   480
gctgcaacaa gcttaatgaa cttctttgag ccagcactgt tattcattca gagatggctt    540
ccattgttct acgttccatc attggttgtt tgcctctctc tattaaaga tatccctgct    600
gcatcaggtg tcaagatttg cttcatcaca gctggagggt ggtggcgtc actttgtgtg    660
gcgggtttta cagctattgc tgtgagaaaa atggtgaaga cagaaatgac tgatgctgag    720
cctatggcga aaccctctcc tttttctcca ttggaaatgt ggcttggagt ggggtcttc    780
cttgtatcat tgttgtcgc cttattatat agaacggcat tggggactgc agccagaaca    840
tgccttcctt tcctactagc atccaccgtg ctaggctata tggttggttc tgggttacca    900
tctggtgtta agaaggtttt ccatcccatt atttgttgtg cactatctgc agatttggca   960
gcgttggcct ttgggttcct ttcccaatcc ggacttgatc cgttctagg atattacctt    1020
acaaaagttt catccaatcc tggagctggt gatgtgttaa tgggattctt gggatctgtc   1080
```

```
attctttctt ttgctttctc aatgttcaag cagagaaagc ttgttaagag acatgcagct   1140
gagatttttca cgtcagtcat tgtttcaaca ctatttttcat tgtattcaac ggctctcgtg  1200
ggacgcctag ttgagttaga accaacattg actgtatcca ttattcccag atgtataacc   1260
gtggcattag ccctcagcat tgtgtcattc tttgaaggtg ccaattcatc tctcacagct   1320
gctgtagtta ttgtaactgg tctcattgga gcaaattttg tacaagcagt gctcgataaa   1380
ttaaattttc ttgatcccat tgctcgagga atagcaactc cttccagtgc tcatggactg   1440
ggaactgcag cattgtcagc caaggaacct gaggcacttc cattttgtgc cattgcttat   1500
gctctcactg gtatatttgg ttcattgttt tgttcagttc ctgcagttag gcaaagctta   1560
cttgcaataa ttggctga                                                 1578

SEQ ID NO: 41         moltype = DNA   length = 885
FEATURE               Location/Qualifiers
source                1..885
                      mol_type = unassigned DNA
                      organism = Picea abies
misc_feature          1..885
                      note = Plgg1
SEQUENCE: 41
atggccctgg aagttaaacc tgctaaaaat agtaaattgc caaaattgcc agaaaactat   60
tttgagccag tcgaaaaagg tgggtggcca ctgatatcct cttggatcaa acggcatgct  120
gcagagatct tctcagctgt ggtggcttca acaattttt ctctgtactc aacaacagtt   180
gtaggtcgaa tgattggaat ggaaccaacc ttaactgttc gcattttgcc aagatgtatt   240
actgttgcat tagcactgag cattgtctca ctttttgatg ctgcaaatcc ttcccttaca   300
gtagctgtca tggttttaac gggattggtt ggggaaaatt ttgcacaaat atttctcgac   360
aagcttggtt tggatgattc tattgcacga ggaatggcta tagccttcag tgctcatgga   420
ttgggaacga cagcattgtc agcaaaagaa ccagaagcat tgccttctg tgcaatttcc   480
tatgcattaa ctgcggaggc catggctgga gatggtggat cggagcgcct tgacgaagcg   540
ggagtcgctg ggttaggcga gcaacaagat ctgcaagaat tgtacatatt tccacatcga   600
ttacctattg ctgctctgac ggagcctctc gtcctactca acaggaccta cagcaacagg   660
gaggttctcg ggatcatgac ggtgctaacc attgttatcg tgtttctcac gagcattggg   720
tcgttactca tctcggtgct tatggtcgga ttgggtatcg tttgtgtcca tggtgcattt   780
aggttttccg aagatctgtt tttggacgag caggagcagg cggtcagatt cttgtccttc   840
ctcggtggcg gtggatccca tccccctgtt gctatccatg tttga                  885

SEQ ID NO: 42         moltype = DNA   length = 1903
FEATURE               Location/Qualifiers
source                1..1903
                      mol_type = unassigned DNA
                      organism = Populus trichocarpa
misc_feature          1..1903
                      note = malate synthase
SEQUENCE: 42
gaaacactct catacacgtt aaaaaaccata caacaaagaa gagtggcatt gcttaaaaaa   60
cagtcagatc aataatggga cctgcaactt atgagaatca ctatccaccg cccaatatga   120
agaagtttgg ctatgatgct cctgaaggag ttgaaattag aggcagatat gacggagagt   180
ttgcagtgat cctttaccaag gatgctttgc aatttgttgc tgatttgcag agagagttta   240
ggaaccgcat caagtatgca atggagtgtc gcaaggaagc caaaaggagg tacagtgagg   300
gggctttacc aggttttgat ccagctacaa ggtacataag ggaggggggag ttggacatgtg   360
cacctgtccc tccagctgtt gctgatagga aggtggagat tacaggttcca gtggagagga   420
aaatgatcat caatgcactc aattctggag ctaaagtttt catggctgac tttgaagatg   480
cactgtcacc aagttgggag aaccttatga gaggacaagt taacctgaag gacgctgtcg   540
ctgggactat taccttttcac gacaaggtca ggaacagggt ttataagctg aataaccaga   600
cagccaagtt gtttgtccgc ccacgaggtt ggcatctacc tgaggcgcac attctcattg   660
atggagaacc agcaactggt tgccttgtgg acttttggcct ttactttttac cacaactatg   720
cagcattccg tcggattcag ggtgcagggt tcgggccttt cttctatctc cctaagatgg   780
agaattcaag ggaggctaag atatggaact gtgtgttcga gaaagcagag aagatggcag   840
gaattgaaag gggaagcatc agggccactg tcctaatcga aacacttcca gctgtttttcc   900
aaatgaatga aatcctctac gaactaaggg atcactctgt tggcttgaac tgcggaagat   960
gggattacat cttcagctat gtcaagacat tccaggctca cccagatcgc tgctaccag  1020
acagggttca agttggcatg actcagcact tcatgaagag ttactctgat ctcctcatct  1080
ggacatgcca taggcgtggt gtccatgcga tgggcggcat ggcagctcag attccaatca  1140
gagacgatcc agaggcgaat aatgaagcac tagaactcgt gcgaaaggac aagctaagag  1200
aggttcgagc aggacatgat ggaacatggg cagcccaccc tggaacttatc ccagcttgca  1260
tggaagtctt ctcaaacaac atgggaaaca cgccaaacca aatccagtcc atgaagcgcg  1320
aagatgcatc aaccattaca gaggaagacc tcttacagag gccaagaggg tcccgttcgt  1380
tggaaggtct ccgcctaaac acccgtgtag gaatccagta cttagcagca tggctaactg  1440
gaactggctc agtccctctt tacaacctca tggaagacgc tgccactgca gaaatcagca  1500
gagttcagaa ctggcaatgg cttaaatatg gagtggaact tgacggagat ggccttggag  1560
tgaaagttaa caatgatctg ttcgggaaag tggtggaaga ggaaatggct aggattgaaa  1620
gggaagttgg gaaagagaaa ttcaagaggg gaatgtacaa ggaggcctgc aagattttcg  1680
caaggcaatg cacagcacct acactggatg attttcttac cctgaatgct tatgataata  1740
tcgtcatcca tcaccctatg ggatcatcat cccgcctcta agtcatgagt ttcatcgctt  1800
gttttttaatt tcctgggatt gatgtgtgcc ctcgtgttct actctactac tacaacttga  1860
ataaaatcct ttctatctgt ttgaacttaa gttccaccca tta                    1903
```

| SEQ ID NO: 43 | moltype = DNA length = 2038 |
|---|---|
| FEATURE | Location/Qualifiers |
| source | 1..2038 |
| | mol_type = unassigned DNA |
| | organism = Populus tremula |
| misc_feature | 1..2038 |
| | note = malate synthase |
| SEQUENCE: 43 | |

```
gtttaatcaa atcttacgca cataaagcca taacgataat gctccttgta cctatccact    60
tgcctccact ctcccttat atatttctac tcttgagctt acccttgaaa cactctcata   120
cacgttaaaa accatacagt aaagaagaat cgcgttgcta aaaaaacagt gagatcaata   180
atgagacctg caactaatgg gaatccggat gcaccgcccg atatgaagaa gtttggctat   240
gattctcctg aaggagttga agttagaggc agatatgacg gcgagtttgc agtgatcctt   300
accaaggatg ctttgcaatt tgttgctgat ttgcagagag agtttaggaa ccgcatcaag   360
tatgcaatgg agtgtcgcaa ggaagccaaa aggaggtaca gtgagggggc tctaccaggg   420
tttgatccag ctacaaggtg cataaggag gaggagtgga catgtgcacc tgcccctcca   480
gctgttgatg ataggaaggt ggagattaca ggtccagtgg agaggaaaat gatcatcaat   540
gccctcaatt ctggagcgaa agttttcatg gctgactttg aagatgcgct ctcaccaagc   600
tgggagaacc ttatgagagg acaagttaac ctgaaggatg ctgttgatgg gactattacc   660
tttcacgaca aggtcaggaa cagggtttat aagctgaata atcagacagc caagttgttt   720
gtccgcccac gaggttggca tctacctgag gcgcacattc tcattgatgg agaacctgca   780
actgttgcc ttgtgactt tggcctttac ttttaccaca acatgg attccgtcgg   840
aatcagggtg caggcttcgg gcctttcttc tatctcccta agatggagaa ttcaaggga   900
gctaagatat ggaactgtgt gttttgagaaa cagagaagg tggcaggaat tgaaagggga   960
agcatcaggg ccactgtcct tatcgaaaca cttccagctg tcttccaaat gaatgaaatc  1020
ctccacgaac taagggatca ctctgttggg ttgaactgcg gaagatggga ttacatcttc  1080
agctatgtca agacattcca ggctcaccca gatcgcctgc taccagacag agttcaagtt  1140
ggcatgactc agcacttcac gaagagctac tccgatctcc tcatctggac atgccatagg  1200
cgtggtgtgc acgcgatggg cggcatggca gctcagattc ctatcagaga cgatccagag  1260
gcgaataagg aagcactgga gctcgtcga aaggacaagc taagagagtt tcgagcagga  1320
catgacggaa catgggcagc ccaccctgga cttatcccag cttgcatgga agtcttctca  1380
gacaacatgg gaaacacgcc aaaccagatc caaaccatga agcgcgaaga tgcatcaacc  1440
ataacgagg aagacctctt acagagacca agagggtccc gttcattgga aggtctccgc  1500
ctaaacaccc gtgtgggaat ccagtaccta gcagcatggc taactggaac tggatcggtc  1560
cctctttaca acctcatgga agatgccgcc accgcagaaa tcagcagagt tcagaactgg  1620
caatggctta aatatggagt ggaacttgac ggagatggcc ttggagtgag agtaacaat  1680
gatctgttcg ggaaagtggt ggaggaggag atggctagga ttgaaaggga ggtcgggaaa  1740
gagaagttca agaggggaag gtacaaggag gcctgcaaga ttttcgcaag gcaatgcaca  1800
gcacctacac tagatgattt tcttacactg aatgcttatg aaaatatcgt cagccatcac  1860
cctatgggat catcaccccg cctctaagtc acgagtttca tcgcttgttt taatttccaa  1920
gggattgatg tgtgccctcg tgttccactc tactactaca agttatctac aacttgaata  1980
aaatctttc tacctgtttg aacttaagtt ccacccttta cttgcactta ttttattt    2038
```

| SEQ ID NO: 44 | moltype = DNA length = 1713 |
|---|---|
| FEATURE | Location/Qualifiers |
| source | 1..1713 |
| | mol_type = unassigned DNA |
| | organism = Eucalyptus grandis |
| misc_feature | 1..1713 |
| | note = Malate Synthase |
| SEQUENCE: 44 | |

```
atgatggatc tcgggtcgtt cacgtaccaa gcaccagcaa ccaacaaggc caaccccgcg    60
tccggctacg acgtcccga gggagtggga atcagagggc gttacgatgc ccagttcgcc   120
aggatcctcn accgggacgc cttgcagttc gtcgccgatc tgcagaggga gttcaggggc   180
cacatcaagt acgccatgga gtgtcgccgc aacgccaagc agcgctacaa cgccggcgcg   240
ctgcctgggt cgaccccgc tacgaggtac gtgagggaag gcgagtggac gtgctcgctg   300
gtcccaccag ccgtggccga ccggagggtg gagatcactg ccctgtcga gcgcaagatg   360
atcatcaacg cgctcaactc tggcgccaaa gttttcatgg cagatttcga agatgcgcta   420
tccccgagct gggagaacct gatgagaggg caagtgaacc tgaaggatgc ggtggatggg   480
accataacct tccacgacaa ggcccgaaac agggtctaca agctcaatga ccagattgcc   540
aagctctttg tccggccccg aggttggcac ttgcctgagt ctcacatcct cattgacggt   600
gagcctgcaa ccgttgcct cttcgacttt ggcctctact cttccacaa ctacgcttca   660
ttcaggaaaa tgcagggtga ggggttcggg cccttcttct atctcccctaa gatggagcat   720
tccagggaag cgaagatatg gaacagcgtc tttgagaggg cagagaaaat ggcgggcatc   780
gagagaggga gcataaggc aacggtattg atagagacac tacctgcagt gttccagatg   840
gatgagatac tgtacgagct gagggatcac tcggtcggat tgaactgcgg aagatgggac   900
tacatcttca gctatgtcaa gaccttccag gctcatccca atcgcctact gcctgacagg   960
tttcaggtcg gatgaccca gcacttcatg gtcttact ctgatctcct catccggact  1020
tgccatcggc gcggtgttca tgccatggga ggcatggcgg ctcaaatccc gatcagagat  1080
gatccggtgg ccaatgaggc ggcgctgaa ctagtaagga agacaagct cagagaagtc  1140
agggccgggc atgacgggac atgggctgct cacccgggtt aatcccggc ttgtatgaa  1200
gtcttcacga atcacatggg caatgcgcca caccagatcc aatcagtcaa gagagaggac  1260
gcagccaaca taaccgagga agacctcctc cagaggccga agggacaagct aacttttgaa  1320
ggcctccgac tcaacactcg ggttgggatc caataccctgg cagcctggct cacagggaca  1380
gggtcggtcc cactctacaa tctcatggag gatcgcgcaa ctgccgagat cagccgagtc  1440
cagaactggc agtggctgaa gtatggtgtg gagctggacg tgatgggt tggagtgaga  1500
gtgagcttgg atctattcgc gagggtggtg gaggaagagg tggccaggat tgagnnagag  1560
gttgggaagg acaagttcaa gaggggatg tacaaggagg ctggcaagat gttcacgaga  1620
```

```
caatgcacgg cgccagtgtt ggacgatttc ctgacgctcg atgcctacaa tcacatcgtc    1680
gtgcatcatc ctaggggtc ttccaagctc tga                                   1713
```

| SEQ ID NO: 45 | moltype = AA    length = 568 |
|---|---|
| FEATURE | Location/Qualifiers |
| source | 1..568 |
|  | mol_type = protein |
|  | organism = Eucalyptus grandis |
| REGION | 1..568 |
|  | note = Malate Synthase |

SEQUENCE: 45
```
MMDLGSFTYQ APATNKANPA SGYDVPEGVD IRGRYDAQFA RILRDALQFV ADLQREFRGH    60
IKYAMECRRN AKQRYNAGAL PGFDPATRYV REGEWTCSLV PPAVADRRVE ITGPVERKMI   120
INALNSGAKV FMADFEDALS PSWENLMRGQ VNLKDAVDGT ITFHDKARNR VYKLNDQIAK   180
LFVRPRGWHL PESHILIDGE PATGCLFDFG LYFFHNYASF RKMQGEGFGP FFYLPKMEHS   240
REAKIWNSVF ERAEKMAGIE RGSIRATVLI ETLPAVFQMD EILYELRDHS VGLNCGRWDY   300
IFSYVKTFQA HPDRLLPDRF QVGMTQHFMR SYSDLLIRTC HRRGVHAMGG MAAQIPIRDD   360
PVANEAALEL VRKDKLREVR AGHDGTWAAH PGLIPACMEV FTNHMGNAPH QIQSVKREDA   420
ANITEEDLLQ RPRGARTLEG LRLNTRVGIQ YLAAWLTGTG SVPLYNLMED AATAEISRVQ   480
NWQWLKYGVE LDGDGVGVRV SLDLFARVVE EEVARIEEVG KDKFKKGMYK EAGKMFTRQC   540
TAPVLDDFLT LDAYNHIVVH HPRGSSKL                                      568
```

| SEQ ID NO: 46 | moltype = DNA    length = 3288 |
|---|---|
| FEATURE | Location/Qualifiers |
| source | 1..3288 |
|  | mol_type = unassigned DNA |
|  | organism = Chlamydomonas reinhardtii |
| misc_feature | 1..3288 |
|  | note = Glycolate Dehydrogenase |

SEQUENCE: 46
```
atgccacgcg gccagggcaa gcgcctggct cagctccttg gagctcagct gaagcagtac     60
gcagcggagg tgcgtggcat cagcacagct ggtggcgctt ctcgcggtgg agctcgagga    120
cctgcatccc ctagctcgct agagcagcag acgcgccagg tcgctcaggt tgctgttcag    180
cagtcgactc agcaggcagt gaaggtcgtt gtgccggcca tcaaagtaga cctggttggt    240
gcggtcagct cggtgtctga gagcgacaag gtggagccgg gtgtgttcaa gaacgtggat    300
ggccaccgct tcgaggacgg tcgctatgcc gcttttgttg aggagattac aaagtttatc    360
cccaaggagc gccagtactc ggaccccgtg cgcacattcg cgtatggcac ggatgcctcc    420
ttctaccggc ttaacccgaa gctggtagtg aaggtgcaca acgaggacga ggtccgcgcg    480
atcatgccca tcgcggagcg gctgcaggtc cctatcacct tccgcgcggc cggcacgtcg    540
ctgtctgggc aggcaattac cgactcggtg ctcattaagc tgagccacac gggcaagaac    600
ttccgcaact ttaccgtgca cggcgacggt agcgtgatca cggtggagcc gggcctcatt    660
ggcggcgagg tgaaccgcat cctggcggca caccagaaga gaacaagct gcccatccag    720
tacaagatcg acccgaccc ctcctccatc gacagctcgg tgatcggcgg catcgtgtcg    780
aacaacagca gcggcatgtg ttgcggcgtg agccagaaca cctaccacac gctgaaggac    840
atgcgggtgg tgttcgtaga cggaacggtg ctggacacgg ccgaccccaa ctcgtgcacc    900
gccttcatga agagccaccg ctcgctggtg gatggcgtcg tgagcctggc gcgccgcgtg    960
caggccgaca aggagctgac ggcgctcatc cgcgccgagt tcgccatcaa gtgcaccacc   1020
ggctactccc tgaacgcgct ggtggacttc ccggtggaca accccattga gatcatcaag   1080
cacctcatca tcggcagcga gggcacgctg gcttcgtca gccgcgccac ctacaacacc   1140
gtgcccgagt ggcccaacaa ggcctcggcc ttcatcgtgt cccggacgt gcgcgccgcc   1200
tgcaccggcg cctcggtgct gcaaacgag acgtccgtga acgcggtgga gctgtttgac   1260
cgcgccagcc tgcgcgagtg cgagaacaac gaggacatga tgcgcctggt gcccgacatc   1320
aagggctgcg accccatggc ggcagcgctg ctgatcgagt gccgcggcca ggacgaggcc   1380
gcactgcaga gccgcattga ggaggtggtg cgcgtgctga cggcggcggg cctgcccttc   1440
ggcgccaagg ccgcgcagcc catgccatc gacgcctacc ccttccacca cgaccagaag   1500
aacgccaagg tcttctggga cgtgcgcagg ggcctgatcc ccattgtggg cgcggcgcgc   1560
gagcccggca catccatgct gatcgaggac gtggcctgcc ccgtgacaa gctggccgac   1620
atgatgatcg acctgatcga catgttccag cgccacggct accacgacgc ctcctgcatc   1680
ggccacgcgc tcgagggcaa ccttcacttg gtgttctcgc agggcttccg caacaaggag   1740
gaggtgcagc gcttcagcga catgatggag gatgtcgc acctggtggc caccaagcac   1800
tcggcagcc tcaagggcga gcacggcacg ggccgcaacg tggcgccgtt cgtggagatg   1860
gagtggggca acaaggcgta cgagctgatg tgggagctca aggcgctgtt cgaccccagc   1920
cacacccctca acccgggcgt catcctcaac cgcgatcagg acgcgcacat caagttcctg   1980
aagcccctcgc ccgcggcctc gcccatcgtc aaccgctgcg tcgagtgcgg ctttttgcag   2040
tccaactgcc cctcgcgcga catcacgctc acgccgcgcc agcgcatctc cgtgtaccgc   2100
gagatgtacc gcctcaagca gctgggcccg gcgccagcg aggaggagaa gaagcagctg   2160
gcggccatga gcagctcgta cgcctacgac ggcgagcaga cgtgcgcggc ggacggcatg   2220
tgccaggaga agtgcccccgt caagatcaac acgggagacc tgatcaagtc gatgcgtgcc   2280
gagcacatga aggaggagaa gaccgccagc ggcatggcag actggctgac cgccaacttc   2340
ggcgtcatca actccaacgt gccgcgcttc ctcaacatcg tcaacgccat gtacagcgtg   2400
gtgggctcgg cgcctctgtc cgccatcagc cgcgcgctca acgccgccac caaccacttc   2460
gtgccggtgt ggaaccccta catgcccaag ggcgcggcgc cgctcaaggt gcccgccccg   2520
ccggcgccgc cagctgctga ggcctcgggc atcccgcgca aggtggtgta catgtccagc   2580
tgcgtgacgc gcatgatggg cccccgctgc tccgacaccg aggcggccgg ggtgcacgag   2640
aaggtgatga gcctgttcgg caaggccggc tacgagctga tcatcccga gggcgtggcc   2700
agccagtgct gcgcatgat gttcaacagc gccggcttca aggacgccgc cgccagcaag   2760
ggcgcggagc tggaggcggc gctgctcaag gcctcggaca atggcaagat ccccatcgtc   2820
atcgacacct cgccctgcct ggcgcaggtg aagagccaga tcagcgagcc gtcgctcgc   2880
ttcgcgctgt acgagccggt tgagttcatc cggcacttcc tggtggacaa gctggagtgg   2940
```

```
aagaaggtgc gcgaccaggt ggccatccac gtgccctgct cctccaagaa gatgggcatc 3000
gaggagtcct tcgcgaagct ggcgggcctg tgcgccaacg aggtggtgcc ctcgggcatt 3060
ccttgctgcg gcatggcggg cgaccgcggc atgcgcttcc ccgagctgac cggcgcctcg 3120
ctgcagcacc tcaacctgcc caagacctgc aaggacggct actccaccag ccgcacctgc 3180
gagatgtcgc tcagcaacca cgccggcatc aacttcaggg gctggtgta cctggtggat 3240
gaggccacgg cgcctaagaa gcaggccgcc gctgccaaga ccgcgtaa          3288
```

SEQ ID NO: 47        moltype = AA  length = 1095
FEATURE             Location/Qualifiers
source              1..1095
                      mol_type = protein
                      organism = Chlamydomonas reinhardtii
REGION              1..1095
                      note = Glycolate Dehydrogenase
SEQUENCE: 47

```
MPRGQGKRLA QLLGAQLKQY AAEVRGISTA GGASRGGARG PASPSSLEQQ TRQVAQVAVQ   60
QSTQQAVKVV VPAIKVDLVG AVSSVSESDK VEPGVFKNVD GHRFEDGRYA AFVEEITKFI  120
PKERQYSDPV RTFAYGTDAS FYRLNPKLVV KVHNEDEVRR IMPIAERLQV PITFRAAGTS  180
LSGQAITDSV LIKLSHTGKN FRNFTVHGDG SVITVEPGLI GGEVNRILAA HQKKNKLPIQ  240
YKIGPDPSSI DSCMIGGIVS NNSSGMCCGV SQNTYHTLKD MRVVFVDGTV LDTADPNSCT  300
AFMKSHRSLV DGVVSLARRV QADKELTALI RRKFAIKCTT GYSLNALVDF PVDNPIEIIK  360
HLIIGSEGTL GFVSRATYNT VPEWPNKASA FIVPPDVRAA CTGASVLRNE TSVDAVELFD  420
RASLRECENN EDMMRLVPDI KGCDPMAAAL LIECRGQDEA ALQSRIEEVV RVLTAAGLPF  480
GAKAAQPMAI DAYPFHHDQK NAKVFWDVRR GLIPIVGAAR EPGTSMLIED VACPVDKLAD  540
MMIDLIDMFQ RHGYHDASCI GHALEGNLHL VFSQGFRNKE EVQRFSDMME EMCHLVATKH  600
SGSLKGEHGT GRNVAPFVEM EWGNKAYELM WELKALFDPS HTLNPGVILN RDQDAHIKFL  660
KPSPAASPIV NRCIECGFCE SNCPSRDITL TPRQRISVYR EMYRLKQLGP GASEEEKKQL  720
AAMSSSYAYD GEQTCAADGM CQEKCPVKIN TGDLIKSMRA EHMKEEKTAS GMADWLAANF  780
GVINSNVPRF LNIVNAMYSV VGSAPLSAIS RALNAATNHF VPVWNPYMPK GAAPLKVPAP  840
PAPAAAEASG IPRKVVYMSS CVTRMMGPAA SDTETAAVHE KVMSLFGKAG YEVIIPEGVA  900
SQCCGMMFNS RGFKDAAASK GAELEAALLK ASDNGKIPIV IDTSPCLAQV KSQISEPSLR  960
FALYEPVEFI RHFLVDKLEW KKVRDQVAIH VPCSSKKMGI EESFAKLAGL CANEVVPSGI 1020
PCCGMAGDRG MRFPELTGAS LQHLNLPKTC KDGYSTSRTC EMSLSNHAGI NFRGLVYLVD 1080
EATAPKKQAA AAKTA                                                 1095
```

SEQ ID NO: 48        moltype = DNA  length = 4680
FEATURE             Location/Qualifiers
source              1..4680
                      mol_type = unassigned DNA
                      organism = Volvox carteri
misc_feature      1..4680
                      note = Glycolate Dehydrogenase
SEQUENCE: 48

```
atgacagcta tgcaggccaa cggcggcagc ggcattagcg atgttactgc caccgccgcg   60
accacggggg agacctcagg tggggaagcg gggccagtgg gacggctgga ggcggccacg  120
gcgccaacga acgcggcggc gctggcctac tcagatgcgc gtgccaccgg cgtagacggc  180
ctagatgaga cgcgcaagtt tgtgttcgcg gaggaatggg gcttttcgcg gtgggaggt   240
gacctgccgg atgcaccac gcccgccacg tttgccgaca tgtttcccga gcgtttcttc  300
gccttcaaac ccctgcgcgc ggtaacgcg gtggcgctac cactggtcgc tatggccgtt   360
ggctacggct ggctgtggta catgcactca atctgccccg cctggcagca gctcgcgtgc  420
gcagccctta tcggcaccgc ttacacgggc ctctttaagg tcgcccacga gtgtgcgcga  480
ttcagcttc tgcctgaagc tcctcgcctc caagatgcgc tagggcttgt cctcatgctg  540
ccgtcgttgt acccttcac ctccggcgc ctccattaca tccaccatat ggcgcacctc  600
aacatgctgt gggaggatac ctttggctgg cacccgtaca cgaagctgca gctggccacg  660
gagctcctct gtgggcagca ctggctcctg gcactgcggc gcctggccgc gaccacaccg  720
ctaaagctgt ttgcgtccgt gggcactgga cttcgctcct ttgacgggct ggacttgaag  780
cgcttccaca agacaccta ctgggctgtg ctggcgggct ggtctgggcc catcctgttt  840
ttgggtttcg gcatcccggc tatcattaag atgtttggct tgtcagtccg tctagccgac  900
cgggcttggg ggggcttagt aagcggctac ctgctccct ggctggttct ccacttctgg  960
ctgtccactc tatcgctcct gcagcacacc gcaccgcata ttccattccg cgccgaggac 1020
gcgggctacg actccggccg cgcgccatc tgcggcaccg tgacggtcgg gctgccacgg 1080
cctctgagc tgctgcttaa cgacgccaac tactccctac cgcagctggt ggcccctggg 1140
atgccagtgt tcacgcgcg ggaggcgtat gagtacatgc gggagcggtt gctgccgtac 1200
ctgacggagg cgacgcttag cgtaaaacta ctgaccaacc atattaccaa gtggcaggtt 1260
tatgatgcgg aaaaggagac gtaccttcct ctggatgagg tcatgcagga gctcgaacgc 1320
gacattgcca ctcttatgga ggaggctgag caggcggagg aggaggagaa agtttcaggg 1380
gggccaagtg gcggagcggt agaggggcag ggcaagcgcc tggcgcagct gttgggtgcg 1440
cagcttaagc aatacatttc ggaggttcgc agcatcagca gctcaaatgc tgctggtcgg 1500
ggagcgttgg gcagcggcca cacgcctacg acgcaccgtcg tcactggcca gcaaacaggt 1560
tctcatgccc aggtcgcagt ccagcaggct acacagcagc acttgaaagt tgtggtgccg 1620
gccatcagga ccgatctggt cggagcggtg tctatggtgt ctgatggcga aaagtggag 1680
ccaggcgtct tcaagaacat tgacggacac cgcttcgacg acggtcgcta ccaggctttt 1740
attgaggaaa tcacaaaatt tatcccccaag gagcggcagt acaccgaccc tgtccgcacg 1800
ttcgcgtatg gcacagacgc gagtttctac gccttaacc caaagctggt cgttaaggtc 1860
cacaatgaag aagaagttcg gaagattttg cccatcgcgg agcggctcaa gtgccggtc 1920
accttccgtg ctgcgggtac atccctctcg gccaggcta tcaccgactc ggtgctgatt 1980
aagctcagcc acaccggcaa gaattccccg aactacaccg tgcacggcga cggcagcagc 2040
atcacagtgg agcggggcct catcgtggc gaggttaacc gcatcctggc ggcgtatcag 2100
aagaagcaca agctgcccat tcagtacaag ataggcccag accgtcttc catcgactct 2160
```

```
tgcatgatcg gcggcatcgt ggccaacaac agcagcggca tgtgctgcgg tgtcagccaa   2220
aacacatatc acacgctcaa ggatatgcgc gtgttgtttg tggacggcac ggtactggat   2280
acggcagatc cggacagctg cgcggccttc ctcaagagcc ataaggccct ggtgacggc    2340
gtcgtggacc tggcgcggcg tgtgcaggct gacaggagc tgacggctct tatccgtcgc   2400
aagtttgcca tcaaatgcac caccggctat tcgctgaatg cgctggtgga tttcccgctg   2460
gacaacccca ttgagattat caagcacgtc atcattggca gcgagggcac tctgggcttc   2520
gtgtcgcggg ccacctacaa cactgtgccc gagtggccca acaaggcctc ggccttcatc   2580
gtcttcccgg acgtgcgggc ggcatgcatg ggtgcctccg tgctccgaaa tgagacctct   2640
gtggacgcag tagagctgtt tgacagggct tccctacgcg agtgcgagaa caatgaggac   2700
atgatgcggc tggtgccaga catcaagggc tgcgacccca tggctgccgc gctgctgatt   2760
gagtgccgtg gccaggacga ggcggcgctg cagggtcgta ttgaggaggt ggtccgtgct   2820
cttacctcgg cgggcctgcc ggtgggagcg aaggcggctg aaccccgccc catcaccgcc   2880
tatccctcc accacgatgc caagaactcg aaagtcttct gggacgtgcg caggggtctg   2940
attccgatcg tgggtgccgc ccgtgagccg ggtacctcca tgcttattga ggacgtccgt   3000
tgccccgtgg acaagctggc ggacatgatg attgacctga ttgacatgtt ccagcgctat   3060
ggctacaacg acgcttcgtg cttcggccac gcgctgaggg caacctgca cctggtcttc   3120
tctcagggct tccgtaccaa ggaggaggta cagcgatttg cggacatgat ggaggagatg   3180
tgctcatcg tggccactaa acacagcggc agcctgaagg gcgagcatgg cacaggccgg   3240
aacgtggctc ccttcgttga tgtgaatgg ggcagcaagg cgtatgagct gatgtgggag   3300
ctcaaggagc tgtttgaccc caagtacacg ctcaaccccg gcgtcattct caaccgggac   3360
cccgatgcgc acatcaaatt cctcaagcct tcgcctgctg cttcgccaat cgttaatcgc   3420
tgcatcgagt gcggcttctg cgagtccaac tgccctcccc gagacatcac gctcacgccc   3480
cgccagcgca tcgccgtgta ccgtgagatg taccgcctga gcagctggg ccccgccgcc   3540
agcgaggaag agaagcagca gttggcagcc attacaagct cctatgctta cgatggcgag   3600
cagacgtgcg ccgccgacgg catgtgccag agaagtgcc ccgtcaagat aaacacaggc   3660
gacatgatca aggctctccg cgccgagcac atgaaggagg ccaagtccgc cagtggtgct   3720
gccatgtgga tggctaacaa cttcggagtc ctcaacgcca cagtgccgcg cttcctgaac   3780
ctcgttaatt tggcgcacag tatcctgggc cccaagccgc ttgaggccat ctcccgggcg   3840
ctgaacgctg ccaccaatca cctggtgccc gtctggaacc cctacatgcc caagggcgcc   3900
gcgccgctga aggtgcccgc tccgttccct gcacccgccg cgtcctctgg cggcatcccc   3960
cgccgagtgg tgtacatgcc ctcttgcgtg acccgcatga tgggcccgc ggcgagcgac   4020
aaggagacgg cctctgtgca tgagaagatt ttgagcctct caacaaggc cggctacgag   4080
gtcattgttc cagagggtgt cagcagccaa tgttgcggca tgatgttcaa cagccgtggc   4140
ttcaaggacg ccgctgccgc caagggtgcc gatctggaag cggcgctgct caaggcatcc   4200
gataacggca agatcccat cgttatggac acttcgccat gcctggcgca ggttaagagc   4260
caaatctcgg agccagcgct acgcttcgcg ctgtacgaac cggttgagtt catcaggcac   4320
ttcctggttg acaaacttga gtggcgcaag gtgcgggagc aggtggccat ccatgtgccc   4380
tgctcatcca agaagatggg catcgaggag tccttgccca gctggcagg attgtgtgcg   4440
cacgaggttg tcccgtcggg cattccctgc tgcggtatgg ctggcgaccg tggaatgcgc   4500
tacccggagc tgactggctc ctcactgcag cacctaaacc tgcccaagag ctgcagcgat   4560
ggctactcca ccagtcgcac ctgcgagatg tcgttgtcca accactcggg catcaacttc   4620
aggggcctgg tctacttggt ggacgaggcg actagcccca agaaggcggc aaccgcatga   4680
```

```
SEQ ID NO: 49          moltype = AA   length = 1559
FEATURE                Location/Qualifiers
source                 1..1559
                       mol_type = protein
                       organism = Volvox carteri
REGION                 1..1559
                       note = Glycolate Dehydrogenase
SEQUENCE: 49
MTAMQANGGS GISDVTATAA TTGETSGGEA GPVGRLEAAT APTDAAALAY SDAGATGVDG     60
LDETRKFVFA EEWGFSRVGG DLPDGTTPAT FADMFPERFF AFNPLRAVTA VALPLVAMAV    120
GYGWLWYMHS ICPAWQQLAC AALIGTAYTG LFKVAHECAR FSFLPEAPRL QDALGLVLML    180
PSLYPFTSWR LHYIHHMAHL NMLWEDTFGW HPYTKLQLAT ELLCGQHWLL ALRRLALTTP    240
LKLFASVGHW LRSFDGLDLK RFHKDTYWAV LAGWSGPILF LGFGIPAIIK MFGLSVRLAD    300
RAWGGLVSGY LLPWLVFHFW LSTLSLLQHT APHIPFRAED AGYDSGRAAI CGTVTVRLPR    360
PLELLLNDAN YSLPQLVAPG MPVFHAREAY EYMRERLLPY LTEATLSVKL LTNHITKWQV    420
YDAEKETYLP LDEVMQELER DIATLMEEAE QAEEEEKVSG GPSGGAVEGQ GKRLAQLLGA    480
QLKQYISEVR SISSSNAAGR GALGSGHTPT TQVVTGQQTR SHAQVAVQQA TQQHLKVVVP    540
AIRTDLVGAV SMVSDGEKVE PGVFKNIDGH RFDDGRYQAF IEEITKFIPK ERQYTDPVRT    600
FAYGIDASFY RLNPKLVKV HNEEEVRKIL PIAERLKPV TFRAAGTSLS GQAITDSVLI    660
KLSHTGKNFR NYTVHGDGSS ITVEPGLIGG EVNRILAAYQ KKHKLPIQYK IGPDPSSIDS    720
CMIGGIVANN SSGMCCGVSQ NTYHTLKDMR VLFVDGTVLD TADPDSCAAF LKSHKALVDG    780
VVDLARRVQA DRELTALIRR KFAIKCTTGY SLNALVDFPL DNPIEIIKHV IIGSEGTLGF    840
VSRATYNTVP EWPNKASAFI VFPDVRAACM GASVLRNETS VDAVELFDRA SLRECENNED    900
MMRLVPDIKG CDPMAAALLI ECRGQDEAAL QGRIEEVVRA LTSAGLPVGA KAAEPRPITA    960
YPFHHDAKNS KVFWDVRRGL IPIVGAAREP GTSMLIEDVA CPVDKLADMM IDLIDMFQRY   1020
GYNDASCFGH ALEGNLHLVF SQGFRTKEEV QRFADMMEEM CYIVATKHSG SLKGEHGTGR   1080
NVAPFVEMEW GSKAYELMWE LKELFDPKYT LNPGVILNRD PDAHIKFLKP SPAASPIVNR   1140
CIECGFCESN CPSRDITLTP RQRIAVYREM YRLKQLGPAA SEEEKQQLAA ITSSYAYDGE   1200
QTCAADGMCQ EKCPVKINTG DMIKALRAEH MKEAKSASGA AMWMANNFGV LNATVPRFLN   1260
LVNLAHSILG PKPLEAISRA LNAATNHLVP VWNPYMPKGA APLKVPAPFP APAASSGGIP   1320
RRVVYMPSCV TRMMGPAASD KETASVHEKI LSLFNKAGYE VIVPEGVSSQ CCGMMFNSRG   1380
FKDAAAKGA DLEAALLKAS DNGKIPIVMD TSPCLAVKS QISEPALRFA LYEPVEFIRH   1440
FLVDKLEWRK VREQVAIHVP CSSKKMGIEE SFAKLAGLCA HEVVPSGIPC CGMAGDRGMR   1500
YPELTGSSLQ HLNLPKSCSD GYSTSRTCEM SLSNHSGINF RGLVYLVDEA TSPKKAATA   1559
```